United States Patent
Mitchell et al.

(10) Patent No.: US 7,799,531 B2
(45) Date of Patent: Sep. 21, 2010

(54) DETECTING FETAL CHROMOSOMAL ABNORMALITIES USING TANDEM SINGLE NUCLEOTIDE POLYMORPHISMS

(75) Inventors: Aoy Tomita Mitchell, Elm Grove, WI (US); Michael Mitchell, Elm Grove, WI (US)

(73) Assignee: University of Louisville Research Foundation, Louisville, KY (US)

( * ) Notice: Subject to any disclaimer, the term of this patent is extended or adjusted under 35 U.S.C. 154(b) by 0 days.

(21) Appl. No.: 11/713,069

(22) Filed: Feb. 28, 2007

(65) Prior Publication Data

US 2008/0020390 A1 Jan. 24, 2008

Related U.S. Application Data

(60) Provisional application No. 60/777,865, filed on Feb. 28, 2006.

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ........................ None
See application file for complete search history.

(56) References Cited

U.S. PATENT DOCUMENTS

| 6,979,541 | B1 | 12/2005 | Pont-Kingdon et al. | |
|---|---|---|---|---|
| 2001/0048756 | A1* | 12/2001 | Staub et al. | 382/129 |
| 2003/0082606 | A1 | 5/2003 | Lebo et al. | |
| 2003/0211522 | A1 | 11/2003 | Landes et al. | |
| 2004/0137452 | A1 | 7/2004 | Levett et al. | |
| 2004/0137470 | A1 | 7/2004 | Dhallan | |
| 2005/0049793 | A1 | 3/2005 | Paterlini-Brechot | |
| 2005/0164241 | A1 | 7/2005 | Hahn et al. | |
| 2006/0121452 | A1 | 6/2006 | Dhallan | |
| 2006/0160105 | A1 | 7/2006 | Dhallan | |
| 2007/0207466 | A1* | 9/2007 | Cantor et al. | 435/6 |
| 2008/0318235 | A1 | 12/2008 | Handyside | |

FOREIGN PATENT DOCUMENTS

| WO | WO0034652 A1 * | 6/2000 |
|---|---|---|
| WO | WO 02/068685 | 9/2002 |
| WO | WO 03/062441 | 7/2003 |
| WO | WO 2004/078999 | 9/2004 |
| WO | WO 2004/079011 | 9/2004 |
| WO | WO 2005/023091 A2 * | 3/2005 |
| WO | WO 2005/035725 | 4/2005 |
| WO | WO 2005/044086 | 5/2005 |
| WO | WO 2006/011738 | 2/2006 |

OTHER PUBLICATIONS

Illanes et al. Prenatal Diagnosis. 2006. 26: 1216-1218.*
Li et al. Journal of the Society for Gynecologic Investigation. 2003. 10: 503-508.*
Zhong et al. Annals NY Acad Sci. 2006, 945: 250-257.*
Human Chromosome 21 cSNP database, University of Geneva. Swiss Institute of Bioinformatics, HC21S00131, available via url: <csnp.unige.ch/cgi-bin/csnp_fetch?db=csnp&format=html&entry=HC21G00062>.*
The EMBL-EBI Database, EBI Dbfetch, Accession No. AF239726, Mar. 22, 2000.*
Human Chromosome 21 cSNP database, University of Geneva. Swiss Institute of Bioinformatics, HC21S00027, available via url: <csnp.unige.ch/cgi-bin/csnp_fetch?db=csnp&format=html&entry=HC21G00018>.*
HOWDY Database, Human Organized Whole Genome Database, Marker 5618, NM_003895, available via url: <howdy.jst.go.jp/HOWDYCL/HOWDY.pl?Cls=Marker&Key=UKEY&Val=5618>.*
Andre, P. et al., *Fidelity and Mutational Spectrum of Pfu DNA Polymerase on a Human Mitochondrial DNA Sequence*, Genome Res., 1997. 7: p. 843-852.
Adams, K. et al., *Microchimerism An investigative Frontier in Autoimmunity and Transplantation*. JAMA. 2004, 291(9): p. 1127-1131.
Andonova, S., et al., *Introduction of the QF-PCR analysis for the purposes of prenatal diagnosis in Bulgaria—estimation of applicability of 6 STR markers on chromosomes 21 and 18*. Prenat. Diagn., 2004. 24(3): p. 202-208.
BBC News, *Safer test for unborn babies hope*. BBC News 2005. Oct. 4. http://news.bbc.co.uk/2/hi/health/4307628.stm.
Birch, L., et al., *Accurate and Robust Quantification of Circulating Fetal and Total DNA in Maternal Plasma form 5 to 41 Weeks of Gestation*. Clin. Chem., 2005. 51(2): p. 312-320.
Chim, S.C., et al., Detection of the placental epigenetic signature of the maspin gene in maternal plasma, PNAS 2005, 102(41): p. 14753-14758.
Cline, J. et al., *PCR fidelity of Pfu polmerase and other thermostable DNA polymerases*, Nucleic Acids Res. 1996, 24(18): p. 3546-3551.
Dhallan, R., et al., *A non-invasive test for prenatal diagnosis based on fetal DNA present in maternal blood: a preliminary study*. www.thelancet.com 2007. DOI:10.1016/S0140-6736(07)60115-9.
Dhallan, R., et al., *Methods to Increase the Percentage of Free Fetal DNA Recovered From the Maternal Circulation*. JAMA, 2004. 291(9): p. 1114-1119.
Ding, C. et al., *MS Analysis of single nucleotide differences in circulating nucleic acids: Application to noninvasive prenatal diagnosis*. PNAS, 2004, 101(29): p. 10762-10767.
Khrapko, K., et al., *Constant denaturant capillary electrophoresis (CDCE): a high resolution approach to mutational analysis*. Nucleic Acids Res., 1994. 22(3): p. 364-369.
Lerman, L.S. et al., *Computational simulation of DNA melting and its application to denaturing gradient gel electrophoresis*. Methods Enzymol., 1987. 155: p. 482-501.
Li, Y. et al. *Detection of Paternally Inherited Fetal Point Mutations for β-Thalassemia Using Size Fractionated Cell-Free DNA in Maternal Plasma*. JAMA., 2005. 293(7): p. 843-9. Corr: Jama, 2005. 293(14): p. 1728.
Li, Y., et al., *Size Separation of Circulatory DNA in Maternal Plasma Permits Ready Detection of Fetal DNA Polymorphisms*. Clin. Chem., 2004. 50(6): p. 1002-1011.

(Continued)

*Primary Examiner*—Carla Myers
(74) *Attorney, Agent, or Firm*—McDermott Will & Emery LLP

(57) ABSTRACT

The invention provides tandem single nucleotide polymorphisms and methods for their use, for example, in diagnosing Down Syndrome.

46 Claims, 2 Drawing Sheets

OTHER PUBLICATIONS

Lim, E.I. et al., *Combination of Competitive Quantative PCR and Conatant Denaturant Capillary Electrophoresis for High-resolution Detection and Enumeration of Microbial Cells.* 2001. Appl. Environ. Microbiol. 67(9): p. 3897-3903.

Li-Sucholeiki, X.C. et al., *A sensitive scanning technology for low frequency nuclear point mutations in human genomic DNA.* Nucleic Acids Res., 2000. 28(9): p. E44. (8 pages).

Lo, Y.M. D., et al., *Quantitative Analysis of Fetal DNA in Maternal Plasma and Serum: Implications for Nnoninvasive prenatal Diagnosis.* Am. J. Hum. Genet., 1998. 62(4): p. 768-775.

Lo, Y.M.D. et al., *Free Fetal DNA in Maternal Circulation.* 2004. JAMA 292(23): p. 2835-2836.

Lo, Y.M.D., et al., *Increased Fetal DNA Concentrations in the Plasma of Pregnant Women Carrying Fetuses with Trisomy 21.* Clin. Chem., 1999. 45(10). p. 1747-1751.

Malone, F.D. et al., *First-trimester sonographic screening for Down syndrome.* Obstet. Gynecol., 2003. 102(5 Pt 1): p. 1066-1079.

Parsons, B. et al., *Genotypic selection methods for the direct analysis of point mutations.* Mutation Research, 1997. 387: p. 97-121.

Pertl, B, et al., *Detection of male and female fetal DNA in maternal plasma by multiplex fluorescent polymerase chain reaction amplification of short tandem repeats.* Hum. Genet., 2000. 106: p. 45-49.

Poon, L.M. et al., *Differential DNA Methylation between Fetus and Mother as a Strategy for Detecting Fetal DNA in Maternal Plasma.* Clin. Chem., 2002. 48(1): p. 35-41.

Samura, O. et al., *Diagnosis of Trisomy 21 in Fetal Nucleated Erythrocytes from Maternal Blood by Use of Short Tandem Repeat Sequences.* Clin. Chem., 2001. 47(9): p. 1622-1626.

Simpson, J.L. et al., *Cell-Free Fetal DNA in Maternal Blood: Evolving Clinical Applications.* JAMA, 2004. 291(9): p. 1135-1137.

The International HapMap Consortium, *The International HapMap Project.* Nature, 2003. 426. p. 789-796.

The International HapMap Consortium, *A haplotype map of the human genome.* Nature, 2005. 437. p. 1299-1320.

Thompson J.R, et al., *Heteroduplexes in mixed-template amplifications: formation consequence and elimination by 'reconditioning PCR'*, Nucleic Acids Res., 2002. 30(9): p. 2083-2088.

Thorisson, G. A. et al., *The International HapMap Project Web site.* Genome Res., 2005. 15: p. 1592-1593.

Wald, N.J., et al., *Antenatal screening for Down's syndrome with the quadruple test.* Lancet, 2003. 361(9360): p. 835-836.

Zheng, W. et al., *Origins of human mitochondrial point mutations as DNA polymerase γ-mediated errors,* Mutat. Res., 2006. 599(1-2): p. 11-20.

International Search Report for International Application No. PCT/US2007/005399 (2007).

Database SNP (Online) Retrieved from NCBI Database Accession No. rs2822654 Abstract (2004).

Antonarakis et al., "Analysis of DNA haplotypes suggests a genetic predisposition to trisomy 21 associated with DNA sequences on chromosome 21", *PNAS*, 82(10), 3360-3364 1985.

Nagy et al., "Rapid determination of trisomy 21 from amniotic fluid cells using single-nucleotide polymorphic loci", *Prenat Diagn.*, 25(12), 1138-1141 (2005).

Pont-Kingdon et al., "Direct molecular haplotyping by melting curve analysis of hybridization probes: beta 2-adrenergic receptor haplotypes as an example", *Nucleic Acids Res.*, 33(10), e89 (2005).

Puers, C., et al., *Identification of Repeat Sequence Heterogeneity at the Polymorphic Short Tandem Repeat Locus HUMTH01[AATG]$_n$ and Reassignment of Alleles in Population Analysis by Using a Locus-specific Allelic Ladder,* Am.J.Hum.Genet. 53:953-958, 1993.

* cited by examiner

DETECTING FETAL CHROMOSOMAL ABNORMALITIES USING TANDEM SINGLE NUCLEOTIDE POLYMORPHISMS

RELATED APPLICATION(S)

This patent document claims the benefit of priority of U.S. application Ser. No. 60/777,865, filed Feb. 28, 2006, which application is herein incorporated by reference.

BACKGROUND

About 6.4 million women become pregnant in the U.S. each year, and about 70% of those women have maternal serum screening and/or an ultrasound test in an attempt to determine risks for common birth defects, such as those resulting from trisomy 13, 18, and 21 (Down Syndrome). Both the sensitivity and specificity of these common non-invasive screening tools are extremely poor. The best current non-invasive tests lead to a false positive rate between 7 and 20%. This high false positive rate has two catastrophic consequences for American families and society. First, it creates a large market for the two invasive diagnostic tests, chorionic villus sampling (CVS) and amniocentesis, which each carry a fetal loss rate of 0.5%-1%. These invasive tests directly result in the loss of thousands of normal fetuses annually. Second, the high false positive rate heightens maternal anxiety and stress in the large and fixed proportion of pregnant American women who receive false positive results. However, prenatal diagnosis are critical in managing a pregnancy with chromosomal abnormalities and localized genetic abnormalities, as the diagnosis can allow for interventional care during delivery and can prevent devastating consequences for the neonate. Thus there is a tremendous need for the development of a sensitive and specific non-invasive prenatal diagnostic test for chromosomal abnormalities.

SUMMARY OF CERTAIN EMBODIMENTS OF THE INVENTION

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

BRIEF DESCRIPTION OF THE FIGURES

FIG. 3A depicts results from a sample from a maternal buccal swab. FIG. 3B depicts results from a sample from maternal serum. FIG. 3C depicts results from a sample from maternal serum.

DETAILED DESCRIPTION

Figure 1:
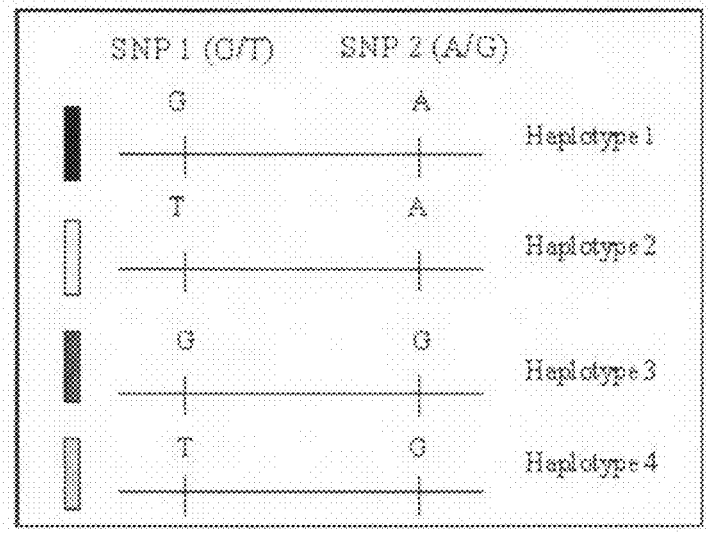
FIG. 1 depicts an example of a tandem SNP.

For years, it has been hoped that the use of fetal cells in maternal blood might be used to assess the genetic status of a developing embryo. Unfortunately, the extremely small amount of fetal cells in maternal blood (about 1 cell per ml) has proven a difficult obstacle to overcome when trying to isolate these cells for widespread clinical testing. However, cell-free fetal DNA is present in circulating maternal serum at higher percentages than fetal cells and has the potential to be assessed for chromosomal or gene defects. Cell-free fetal DNA can range from 1-47% of total DNA in maternal blood. However, a critical limitation that has yet to be successfully overcome is that maternal DNA contamination makes it difficult to differentiate fetal from maternal DNA.

As described herein, this limitation has been overcome by identifying tandem single nucleotide polymorphisms (SNPs) to detect chromosomes, e.g., to detect fetal chromosomal abnormalities. The tandem SNPs are combined with a sensitive DNA separation technology, e.g., high-fidelity PCR and constant denaturant capillary electrophoresis (CDCE), to detect fetal chromosomal abnormalities, e.g., through the simple sampling and comparison of maternal DNA to fetal DNA, e.g., from maternal serum and maternal buccal swabs. This approach substantially eliminates false positives and significantly reduces false negatives.

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

In certain embodiments of the invention, fetal DNA is obtained from maternal blood. In certain embodiments of the invention, fetal DNA is cell-free fetal DNA. In certain embodiments of the invention, maternal DNA is obtained from a biological sample, e.g., maternal blood. In certain embodiments of the invention, maternal DNA is obtained from a buccal swab. In certain embodiments of the invention, maternal DNA is obtained from a biological sample that does not comprise fetal DNA.

In certain embodiments of the invention, fetal DNA is obtained from maternal blood, maternal urine, maternal sweat, maternal cells, or cell free DNA from the mother.

In certain embodiments, the biological sample is biological fluid. In certain embodiments, the biological sample is a maternal biological sample. In certain embodiments, samples may be whole blood, bone marrow, blood spots, blood serum, blood plasma, buffy coat preparations, saliva, cerebrospinal fluid, buccal swabs, solid tissues such as skin and hair, body waste products, such as feces and urine. In other embodiments, samples may be lysates, homogenates, or partially purified samples of biological materials. In other instances, biological materials can include crude or partially purified mixtures of nucleic acids. In certain embodiments, the biological sample is serum, urine, sweat, cells, or cell free DNA.

In certain embodiments of the invention, the comparison step comprises using high-fidelity PCR and constant denaturant capillary electrophoresis to compare the fetal DNA to maternal DNA. In certain embodiments of the invention, the comparison step comprises using at least about 96 tandem single nucleotide polymorphisms.

In certain embodiments of the invention, the method further comprises the step of converting the nucleic acid molecules to a homoduplex state, as opposed to being in heteroduplex form. This can be accomplished, e.g., by using an excess of primers and can aid in the tandem SNP analysis.

In certain embodiments of the invention, methods such as mutation detection technologies can be used to analyze the tandem SNPs. In certain embodiments of the invention, methods such as denaturing HPLC, denaturing capillary electrophoresis, cycling temperature capillary electrophoresis, allele-specific PCRs, quantitative real time PCR approaches such as TaqMan® PCR system, polony PCR approaches, and microarray approaches can be used to analyze the tandem SNPs.

In certain embodiments of the invention, the single nucleotide polymorphisms in each tandem single nucleotide polymorphism are each at most about 250 basepairs apart. In certain embodiments of the invention, the single nucleotide polymorphisms in each tandem single nucleotide polymorphism are each at most about 200 basepairs apart. In certain embodiments of the invention, the single nucleotide polymorphisms in each tandem single nucleotide polymorphism are each at most about 150 basepairs apart. In certain embodiments of the invention, the single nucleotide polymorphisms in each tandem single nucleotide polymorphism are each at most about 100 basepairs apart. In certain embodiments of the invention, the single nucleotide polymorphisms in each tandem single nucleotide polymorphism are each at most about 50 basepairs apart.

In certain embodiments of the invention, at least one tandem single nucleotide polymorphism is located on the p arm of chromosome 21. In certain embodiments of the invention, at least one tandem single nucleotide polymorphism is located on the q arm of chromosome 21.

In certain embodiments of the invention, the chromosomal abnormality is chromosomal aneuploidy. In certain embodiments of the invention, the chromosomal abnormality is trisomy 13, 18 or 21. In certain embodiments of the invention, the chromosomal abnormality is trisomy 21.

In certain embodiments of the invention, the chromosomal abnormality is an insertion mutation (e.g., a large insertion ($\geq$3 megabasepair) or small insertion (<3 megabasepair). In certain embodiments of the invention, the chromosomal abnormality is a deletion mutation (e.g., a large deletion ($\geq$3 megabasepair) or small deletion (<3 megabasepair)). The deleted region could include a deleted gene.

In certain embodiments of the invention, the methods can be used to detect copy number polymorphisms and/or copy number variants in the genome. In certain embodiments of the invention, the methods can be used to detect chromosome 22q11 deletion syndrome, which is associated with cardiac defects.

Chromosomal abnormalities include deletions associated with genetic syndromes and disorders such as the 22q11 deletion syndrome on chromosome 22, which is associated with cardiac defects. Other examples of chromosomal abnormalities include the 11q deletion syndrome on chromosome 11 and 8p deletion syndrome on chromosome 8, both of which are also associated with cardiac defects.

In certain embodiments of the invention, the fetus is a male fetus. In certain embodiments of the invention, the fetus is a female fetus. In certain embodiments of the invention, the fetus is a mammal. In certain embodiments of the invention, the fetus is a human. In certain embodiments of the invention, the fetus is a non-human mammal. In certain embodiments of the invention, the fetus has been determined to be at an elevated risk for having a chromosomal abnormality.

In certain embodiments of the invention, the method further comprises using tandem single nucleotide polymorphisms to compare paternal DNA to the fetal and/or maternal DNA.

In certain embodiments of the invention, the fetal DNA is subjected to an enrichment step. In certain embodiments of the invention, the fetal DNA is not subjected to an enrichment step.

Certain embodiments of the present invention provide a method for identifying chromosomes, comprising comparing tandem single nucleotide polymorphisms on the chromosomes so as to identify the chromosomes. Thus, the methods of the present invention are not limited to maternal-fetal analysis, but can also be applied to other situations, e.g., forensic analysis of blood samples.

In certain embodiments of the invention, the methods further comprises, prior to the comparison step, determining a set of tandem single nucleotide polymorphisms for a specific chromosome.

Certain embodiments of the present invention provide a system comprising packaging material and primers that specifically hybridize to each of the single nucleotide polymorphisms of at least one of the tandem single nucleotide polymorphisms identified herein.

Certain embodiments of the present invention provide a system comprising packaging material and primers that specifically hybridize flanking sequences of at least one of the tandem single nucleotide polymorphisms of the invention.

Certain embodiments of the present invention provide a system comprising packaging material and at least one oligonucleotide that specifically hybridizes to at least one of the tandem single nucleotide polymorphisms of the invention.

Certain embodiments of the present invention provide the use of high-fidelity PCR (HiFi-PCR) to amplify SNPs or tandem SNPs for the purpose of, e.g., determining chromosomal abnormalities.

Certain embodiments of the present invention provide the use of HiFi-PCR to amplify nucleic acids, e.g., DNA, isolated, e.g., from a maternal biological sample to analyze fetal DNA for chromosomal abnormalities.

In certain embodiments, HiFi-PCR is used to detect aneuploidy and large ($\geq$3 megabasepairs) or small (<3 megabasepairs) deletions and/or insertions.

In certain embodiments, the maternal biological sample is serum, urine, sweat, cells, or cell free DNA.

Certain embodiments of the present invention provide an isolated nucleic acid sequence comprising at least one of SEQ ID NOs 1-357.

Certain embodiments of the present invention provide an isolated nucleic acid sequence of the invention (e.g., a nucleic acid sequence comprising a tandem SNP or a primer; e.g., at least one of SEQ ID NOs 1-357) for use in medical treatment or diagnosis.

In certain embodiments, the nucleic acid sequences may be, e.g., isolated nucleic acid sequences and may be, e.g., about 1000 or fewer, e.g., about 900 or fewer, e.g., about 800 or fewer, e.g., about 700 or fewer, e.g., about 600 or fewer, e.g., about 500 or fewer, e.g., about 400 or fewer, e.g., about 300 or fewer, e.g., about 250 or fewer, e.g., about 200 or fewer, e.g., about 150 or fewer, e.g., about 100 or fewer, or e.g., about 50 or fewer nucleic acids in length.

Thus, short haplotypes are used to detect fetal chromosomal abnormalities in maternal serum, e.g., for the most common of these defects, trisomy 21. To demonstrate this method, tandem SNPs for chromosome 21 are identified, heterozygosity of the tandem SNPs determined, the ability to detect fetal DNA from maternal serum demonstrated, and the ability to detect fetal chromosomal abnormalities in maternal serum demonstrated. 118 tandem SNPs have already been identified. These tandem SNPs are useful in the diagnosis of chromosomal abnormalities, for example, of trisomy 21. Thus, certain embodiments of the invention provide the specific tandem SNPs, or combinations thereof, as well as their use in diagnostic and therapeutic applications.

The output of these experiments, e.g., assays based on a set of tandem SNPs for chromosome 21, can be used in the clinic as an alternative to invasive diagnostic tests like amniocentesis and CVS, using, e.g., CDCE or other techniques capable of detecting the tandem SNPs. These diagnostics are sensitive and specific. The tandem SNP assay is particularly suited for fetal DNA analysis because fetal DNA present in maternal serum is generally present as short fragments (e.g., an average of 300 basepairs or fewer).

Thus, certain embodiments of the present invention are directed to each of these tandem SNPs individually, and certain embodiments are directed to combinations of any and/or all of the tandem SNPs. Certain embodiments of the invention are directed to methods of using the tandem SNPs for diagnosing chromosomal abnormalities. Certain embodiments of the invention are directed to compilations of the tandem SNPs (e.g., reference tables) that are useful for diagnosing chromosomal abnormalities. Certain embodiments of the invention are also directed to primers for each of these tandem SNPs individually, and certain embodiments are directed to combinations of primers for any and/or all of the tandem SNPs. Certain embodiments of the invention provide isolated nucleic acid sequences that comprise at least one of the tandem SNPs and compositions that comprise the isolated nucleic acid sequences.

Prenatal Screening

An increasing number of fetal medical conditions can be successfully managed during the neonatal period if an early diagnosis is made. A variety of prenatal screening tools are available for chromosomal and birth defects. The two most commonly utilized non-invasive tools are ultrasound and measurements of maternal serum markers. Both of these "tests" have inadequate sensitivity and specificity for screening the most common of the defects, Down Syndrome (trisomy 21).

An ultrasound screening called the nuchal translucency test is becoming more common. However, this test has an overall sensitivity of 77% for trisomy 21 with a false positive rate of 6% (Malone et al, Obstet Gynecol, 2003. 102(5 Pt 1): p. 1066-79). The most advanced serum marker test is the "quad" screen, which measures the levels of alpha-fetoprotein (AFP), human chorionic gonadotropin (hCG), unconjugated estriol (E3), and inhibin-A. The biological reason for these markers to be elevated or reduced in a percentage of mothers carrying children with trisomy 21 is not understood. Further, the test is only capable of assigning risk categories (i.e., 1 in 250, 1 in 100, 1 in 10), and not in making specific diagnoses. The quad screen is associated with a false positive rate of 7% and a sensitivity of less than 80%, rates which do not approach those achieved by invasive prenatal diagnostic tests (Wald et al., Lancet, 2003. 361(9360): p. 835-6).

Because of the inadequate sensitivity and specificity of currently available non-invasive tools, amniocentesis and chorionic villus sampling (CVS), both invasive procedures, remain the standard for the definitive detection of fetal chromosomal abnormalities. Both of these procedures carry a 0.5%-1% fetal loss rate, which translate into the death of thousands of normal fetuses annually. To solve this problem and meet the overwhelming need for an accurate non-invasive test, several strategies have been previously proposed by other investigators. However, those studies have been limited by their ability to detect and differentiate fetal DNA from maternal DNA.

A PCR-based approach for detecting aneuploidy relies on a method called quantitative fluorescent polymerase chain reaction (QF-PCR) of short tandem repeats (STRs). However, polymerase errors are frequently made in the repeat sequences, generating a high background "noise" for each STR assay. These PCR errors (stutters) make peak area measurements difficult and thus the detection and quantification of low frequency fetal DNA in maternal serum not possible (Dhallan et al., JAMA, 2004. 291(9): p. 1114-9).

In 1994, a technology called constant denaturant capillary electrophoresis (CDCE) combined with high-fidelity PCR (HiFi-PCR) was developed to allow researchers to detect and quantify low frequency somatic mutations present in heterogeneous cell populations (Khrapko et al., Nucleic Acids Res, 1994. 22(3): p. 364-9). Compared to other DNA separation methods, CDCE permits the highest resolution separation of DNA sequences differing by even a single base pair. The separation is based on differences in the melting temperature and the resulting electrophoretic mobility differences as the DNA molecules migrate through a linear polyacrylamide matrix under partially denaturing conditions (Khrapko et al., 1994). CDCE coupled with HiFi-PCR has been demonstrated to detect mutations in ~100 bp sequences with a sensitivity of at least $2 \times 10^{-6}$ in human cells and tissues (Li-Sucholeiki et al., Nucleic Acids Res, 2000. 28(9): p. E44). As described herein, this technology can be applied to single nucleotide polymorphisms (SNPs), natural single basepair variations present in the genome, to separate alleles. CDCE is used in the present invention to screen tandem SNPs to increase the informativeness (or heterozygosity) of each CDCE assay by increasing the number of possible alleles (or haplotypes) available. Through the use of tandem SNPs, a highly specific and sensitive assay for detecting fetal chromosomal abnormalities by simply comparing maternal serum to maternal buccal swabs has been created.

High-Fidelity PCR is an amplification method resulting in an error rate (in per basepair doubling) equal to or better than standard PCR. For example, Taq polymerase has an error rate of $~10^4$ per basepair doubling. As an example, *Pyrococcus furiosus* (Pfu) is a high-fidelity polymerase. The published error rate for Pfu is $1.3 \times 10^{-6}$ per basepair doubling (Cline et al, Nucleic Acids Res. 1996 Sep. 15; 24(18): 3546-3551).

Methods for improving PCR fidelity include, among others: A) using a high-fidelity polymerase enzyme; and B) the addition of chemical reagents (e.g., betaine) that can lower temperatures required during the PCR process. The prolonged heating of DNA and nucleotides during PCR can lead to damaged products, such as deaminated cytosines (uracils) and thus lead to misincorporation errors and miscopying errors during PCR (Andre, Kim, Khrapko, Thilly. Genome Res. 1997 7: 843-852. Zheng, Khrapko, Coller, Thilly, Copeland. Mutat Res. 2006 Jul. 25; 599(1-2): 11-20). Examples of high-fidelity enzymes include Pfu and its derivations, or other enzymes with similar proofreading 3'->5' exonucleases.

In certain embodiments of the invention, amplification, e.g., HiFi-PCR, is performed with primers being in molar excess (e.g., $10^{12}$ copies/μl of primer vs $10^6$ or less of the template) so that it is more likely that primers will anneal with template DNA than with each other (see, e.g., Li-Sucholeiki X C, Thilly W G. Nucleic Acids Res. 2000 May 1; 28(9):E44; Thompson J R, Marcelino L, Polz M. Nucleic Acids Res. 2002 May 1; 30(9): 2083-2088.). This can significantly reduce the creation of heteroduplexes.

A "single nucleotide polymorphism (SNP)" is a single basepair variation in a nucleic acid sequence. A "tandem SNP" is a pair of SNPs that are located in a nucleic acid sequence, e.g. on a chromosome, in a manner that allows for the detection of both of the SNPs. The distance between SNPs generally is about 250 basepairs or fewer, e.g., about 200 basepairs or fewer, e.g., about 150 basepairs or fewer, e.g., about 100 basepairs or fewer, e.g., about 50 basepairs or fewer. The tandem SNPs can be detected by a variety of means that are capable of detecting the tandem SNPs. In one embodiment of the invention, constant denaturant capillary electrophoresis (CDCE) can be combined with high-fidelity PCR (HiFi-PCR) to detect the tandem SNP. In another embodiment, hybridization on a microarray is used. In another embodiment, high-fidelity PCR is used and another method capable of detecting SNPs present at low frequencies is used (e.g., denaturing HPLC, denaturing capillary electrophoresis, cycling temperature capillary electrophoresis, allele-specific PCRs, quantitative real time PCR approaches such as TaqMan® PCR system, polony sequencing approaches, microarray approaches, and mass spectrometry). In another embodiment, high-throughput sequencing approaches, e.g., at a single molecule level, are used.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, J M B, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, J M B, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The invention will now be illustrated by the following non-limiting Examples.

Example 1

Tandem SNPs for Chromosome 21

96 allelic markers on chromosome 21 are selected by examining tandem SNPs. These tandem SNPs will cover both q and p arms of the chromosome. Using heterozygosity data available through dbSNP, DCC Genotype Database and through the HapMap Project, SNPs that appear to be promising for high heterozygosity (≧25%) are selected. Because all four possibilities may not exist in nature due to haplotype blocks in regions of low recombination, those that suggest less than three haplotypes are screened out. FIG. 1 depicts an example of tandem SNPs (SNP 1=rs2839416, average estimated heterozygosity 0.444 and SNP2=rs2839417; average estimated heterozygosity 0.414).

Target sequences covering tandem SNPs are designed using Vector NTI and WinMelt software. As an example, the melting map of a CDCE target covering two tandem SNPs (dbSNP rs2839416 and rs2839417) on chromosome 21 was calculated using WinMelt according to the algorithm of Lerman and Silverstein (Lerman et al., Methods Enzymol, 1987. 155: p. 482-501) and is depicted in FIG. 2.

Figure 2:
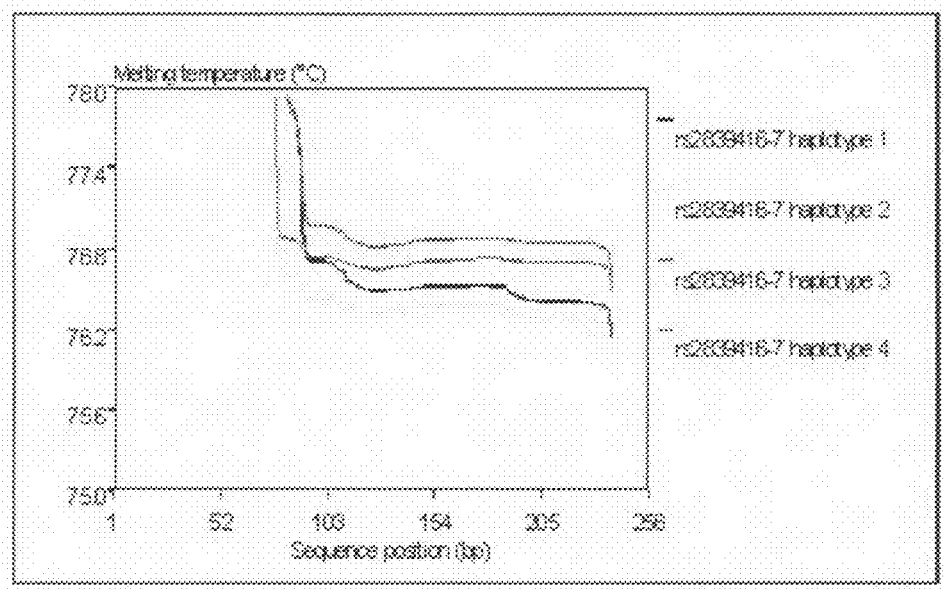
FIG. 2 depicts a DNA melting map of a constant denaturant capillary electrophoresis target sequence covering a tandem SNP.

FIG. 2 depicts a DNA melting map of a CDCE target sequence covering tandem SNPs. All four haplotypes can be theoretically separated according to DNA melting temperature. The black line indicates haplotype 1 (G,A). The yellow line indicates haplotype 2 (T,A). The red line indicates haplotype 3 (G,G). The green line indicates haplotype 4 (T,G).

HiFi PCR optimization for each target sequence is performed using Pfu polymerase. One of primers flanking the target sequence is ~20 bases in length and labeled 5' with a fluorescein molecule. The other primer is about 74 bases including a ~20-base target specific sequence and the 54-base clamp sequence. A standard HiFi PCR condition is applied to all target sequences, varying only annealing temperatures. These PCR amplicons are subjected to CDCE electrophoretic separation. The resulting electropherogram are analyzed for yield and purity of the PCR products. The purity is evaluated by comparing the peak area of the desired products to that of the byproducts and nonspecific amplification. Target sequences that can be amplified with a high PCR efficiency ($\geq 45\%$ per cycle) and low levels of byproducts and nonspecific amplification ($\leq 0.1\%$ of the desired products) are immediately be subjected to CDCE optimization. For those target sequences that do not have acceptable PCR products in the first stage, increasing amounts of $Mg^{+2}$ concentrations (up to about 7 mM) in combination with different annealing temperatures are tested. For the remaining target sequences that still do not work, primer positions are changed and the entire optimization process is repeated.

For CDCE optimization, the relevant haplotypes are created for the targets. The optimal separation condition for each haplotype should provide the greatest resolution among the observed peaks. Initial optimization is done around the theoretical melting temperature ($T_m$) in a 2° C. temperature range in increments of 0.2° C. which covers ($T_m$−1° C.±a predetermined offset) to ($T_m$+1° C.±a predetermined offset).

Electropherogram and peak measurements are transferred to a spreadsheet for analysis. To ensure the quality of the data, minimum and maximum peak heights are used. Individual markers are failed if electrophoretic spikes occur. Peak areas are used to calculate allele ratios. A check for allelic preferential amplification is performed on all 96 tandem SNPs.

Results

In the fall of 2005, the International HapMap Project publicly released genotypes and frequencies from 270 people of four ethnic populations. Chromosome 21 haplotype data from approximately 40,000 SNPs genotyped across four populations, including U.S. residents with northern and western European ancestry, residents of Ibadan, Nigeria, of Tokyo, Japan, and of Beijing, China, were downloaded (2005-10-24: HapMap Public Release #19) and converted to the + orientation. Tandem SNP candidates fell within 100 basepairs from each other and at least three haplotypes existed in all four ethnic populations. CDCE target sequences and primers are designed for the tandem SNPs identified through the HapMap Project. The neighboring sequences for each of the tandem SNPs are imported into a software program, e.g., Sequencher (Gene Codes, Ann Arbor, Mich.) and/or Vector NTI (Invitrogen, Carlsbad, Calif.) for sequence alignment and primer design, and into Winmelt (Medprobe, Oslo, Norway) or Poland software (available on the world wide web at biophys.uniduesseldorf.de/local/POLAND/poland.html) where the algorithm for computing DNA melting temperatures given the Gotoh-Tagashira values for the enthalpy of melting DNA sequences are used to calculate melting temperatures of target sequences. CDCE candidates generally have a high melting region adjacent to a low melting region, lie in a low melting region, melting temperature of the low melting region fall below 80° C., and no "valleys" occur between the high melting region and the low melting region.

All of the 40,000 genotypes on chromosome 21 have been analyzed for tandem SNP/CDCE marker suitability. 118 tandem SNPs/CDCE targets meeting our requirements have been identified (see Table 1 for the first 42 identified and Table 2 for all 118).

Primer sequences for these 118 tandem SNP/CDCE targets have been designed. These will be optimized as described herein using HiFi PCR and CDCE. These optimizations are described herein and include the creation of relevant haplotypes for all targets, a check for allelic preferential amplification during HiFi PCR, and obtaining the greatest resolution among peaks during CDCE. Haplotypes may be separated as homoduplex peaks. However, if certain targets cannot be separated out as homoduplexes, maternal DNA can be separated from fetal DNA as heteroduplexes.

TABLE 1

| Tandem SNP #/Observed haplotypes | dbSNP Name | | Chromosome | Chromosome Position | bp dif |
|---|---|---|---|---|---|
| 1 | rs10482852 | A/C | Chr21 | 14613855 | 86 |
| CC/CT/AC | rs2822567 | C/T | Chr21 | 14613941 | |
| 2 | rs2822654 | A/C | Chr21 | 14687773 | 13 |
| AA/AG/CG/CA | rs1882882 | A/G | Chr21 | 14687786 | |
| 3 | rs2822785 | A/G | Chr21 | 14876399 | 65 |
| AG/GG/AA/GA | rs2822786 | A/G | Chr21 | 14876464 | |
| 4 | rs2822786 | A/G | Chr21 | 14876464 | 67 |
| GC/AC/GT | rs2822787 | C/T | Chr21 | 14876531 | |
| 5 | rs2822816 | A/G | Chr21 | 14948471 | 97 |
| AA/GT/GA | rs2822817 | A/T | Chr2I | 14948568 | |
| 6 | rs2822878 | C/T | Chr21 | 15033311 | 90 |
| CA/CG/TG | rs2822879 | A/G | Chr21 | 15033401 | |
| 7 | rs2223163 | A/G | Chr21 | 15149849 | 72 |
| AT/GT/AC | rs2822963 | C/T | Chr21 | 15149921 | |
| 8 | rs1297213 | A/G | Chr21 | 15253641 | 83 |
| GG/AG/GT/AT | rs1297214 | G/T | Chr21 | 15253724 | |

TABLE 1-continued

| Tandem SNP #/Observed haplotypes | dbSNP Name | | Chromosome | Chromosome Position | bp dif |
|---|---|---|---|---|---|
| 9 CT/CC/TT | rs2142450 rs10482863 | C/T C/T | Chr21 Chr21 | 15257273 15257340 | 67 |
| 10 TC/CC/TT | rs10482863 rs1041403 | C/T C/T | Chr21 Chr21 | 15257340 15257386 | 46 |
| 11 TA/CA/TG | rs2823333 rs2823334 | C/T A/G | Chr21 Chr21 | 15825896 15825985 | 89 |
| 12 GG/AC/GC | rs2823335 rs992557 | A/G C/G | Chr21 Chr21 | 15826379 15826457 | 78 |
| 13 AA/GG/AG | rs2823348 rs2823349 | A/G A/G | Chr21 Chr21 | 15833575 15833601 | 26 |
| 14 AT/AC/CT/CC | rs2823502 rs2823503 | A/C C/T | Chr21 Chr21 | 16124651 16124683 | 32 |
| 15 CC/CA/TC/TA | rs960391 rs13049140 | C/T A/C | Chr21 Chr21 | 17034864 17034893 | 29 |
| 16 CA/TA/TG | rs2824078 rs10482886 | C/T A/G | Chr21 Chr21 | 17134418 17134448 | 30 |
| 17 CT/CC/TC | rs1999288 rs208897 | C/T C/T | Chr21 Chr21 | 17696177 17696269 | 92 |
| 18 GG/GA/AA/AG | rs2824310 rs6517774 | A/G A/G | Chr21 Chr21 | 17744045 17744144 | 99 |
| 19 GG/AA/AG/GA | rs728015 rs728014 | A/G A/G | Chr21 Chr21 | 17968624 17968657 | 33 |
| 20 GG/CG/CC/GC | rs1047978 rs2824495 | C/G C/G | Chr21 Chr21 | 18091026 18091089 | 63 |
| 21 GT/GC/AT/AC | rs157058 rs150141 | A/G C/T | Chr21 Chr21 | 18355312 18355365 | 53 |
| 22 GG/GT/AG/AT | rs2824733 rs2824734 | A/G G/T | Chr21 Chr21 | 18610953 18611032 | 79 |
| 23 AA/GT/GA/AT | rs963638 rs963639 | A/G A/T | Chr21 Chr21 | 19009158 19009214 | 56 |
| 24 AC/TA/TC/AA | rs2187166 rs2156203 | A/T A/C | Chr21 Chr21 | 19081111 19081210 | 99 |
| 25 CT/TC/CC/TT | rs2825470 rs2825471 | C/T C/T | Chr21 Chr21 | 19567109 19567169 | 60 |
| 26 TT/GC/GT | rs2407581 rs2825926 | G/T C/T | Chr21 Chr21 | 20272611 20272639 | 28 |
| 27 GT/AT/GC/AC | rs377685 rs420778 | A/G C/T | Chr21 Chr21 | 20272988 20273021 | 33 |
| 28 AG/CT/CG | rs2826058 rs2826059 | A/C G/T | Chr21 Chr21 | 20464969 20465061 | 92 |
| 29 CT/CC/TT | rs2826072 rs2826073 | C/T C/T | Chr21 Chr21 | 20487958 20488053 | 95 |
| 30 CC/TC/TT | rs2032203 rs2826152 | C/T C/T | Chr21 Chr21 | 20598845 20598943 | 98 |
| 31 CA/TA/CG/TG | rs1735808 rs1786400 | C/T A/G | Chr21 Chr21 | 20766284 20766329 | 45 |
| 32 TG/CA/CG/GA | rs2014509 rs2014519 | C/T A/G | Chr21 Chr21 | 21113081 21113160 | 79 |
| 33 GA/AA/GG | rs2155798 rs2155799 | A/G A/G | Chr21 Chr21 | 21471022 21471097 | 75 |

TABLE 1-continued

| Tandem SNP #/Observed haplotypes | dbSNP Name | | Chromosome | Chromosome Position | bp dif |
|---|---|---|---|---|---|
| 34 GA/GG/CA | rs1475881 rs7275487 | C/G A/G | Chr21 Chr21 | 21748820 21748916 | 96 |
| 35 CG/GG/GC/CC | rs2522558 rs12627388 | C/G C/G | Chr21 Chr21 | 21916691 21916714 | 23 |
| 36 GC/GT/CC/CT | rs12627388 rs2522559 | C/G C/T | Chr21 Chr21 | 21916714 21916762 | 48 |
| 37 AC/GC/GT | rs1735934 rs2826958 | A/G C/T | Chr21 Chr21 | 21995555 21995633 | 78 |
| 38 AC/GT/AT/GC | rs994676 rs2826982 | A/G C/T | Chr21 Chr21 | 22043945 22043979 | 34 |
| 39 AA/GC/AC | rs1735976 rs2827016 | A/G A/C | Chr21 Chr21 | 22054777 22054808 | 31 |
| 40 AA/GA/AG/GG | rs1013069 rs2827307 | A/G A/G | Chr21 Chr21 | 22545627 22545694 | 67 |
| 41 AT/GT/AC/GC | rs244260 rs244261 | A/G C/T | Chr21 Chr21 | 23311737 23311825 | 88 |
| 42 CG/CC/AG/AC | rs2051265 rs198061 | A/C C/G | Chr21 Chr21 | 23334109 23334156 | 47 |

Example 2

Determining Heterozygosity of the Tandem SNPs

As a complement to Example 1, genomic DNA samples from 300 anonymous subjects have been obtained from healthy young adults who are less than 35 years old. The samples are anonymous as the only data obtained were the geographic location of the Red Cross blood donor center, donor gender, and whether or not the donor was 35 and under. These samples were spot-checked to look for the haplotypes seen in the HapMap project.

Example 3

Detecting Fetal DNA from Maternal Serum

A cohort of patients who have been confirmed to have trisomy 21 by traditional karyotype analysis are examined. Tandem SNPs are used to demonstrate detection of trisomy in patients. DNA from 20 patients who have been characterized by traditional karyotype analysis to have trisomy 21 are analyzed with the tandem SNP panel.

Biological samples, including a buccal (cheek) swab and a blood sample are collected from a cohort of pregnant women. Maternal buccal swab samples are compared to maternal serum to demonstrate that a third (paternal) peak is observed in several of the tandem SNP assays. Approximately 20 maternal buccal swab to maternal serum comparisons are made. To control for experimental artifacts, genomic DNA samples from maternal buccal swabs are utilized for each target sequence. The buccal samples are subjected to the process in parallel with the maternal blood sample. Any artifacts generated by the CDCE/HiFi-PCR procedure (including nonspecific PCR amplification and polymerase-induced mutations) are revealed as background peaks in the buccal swab samples.

Example 4

Detecting Fetal Chromosomal Abnormalities

Figure 3:
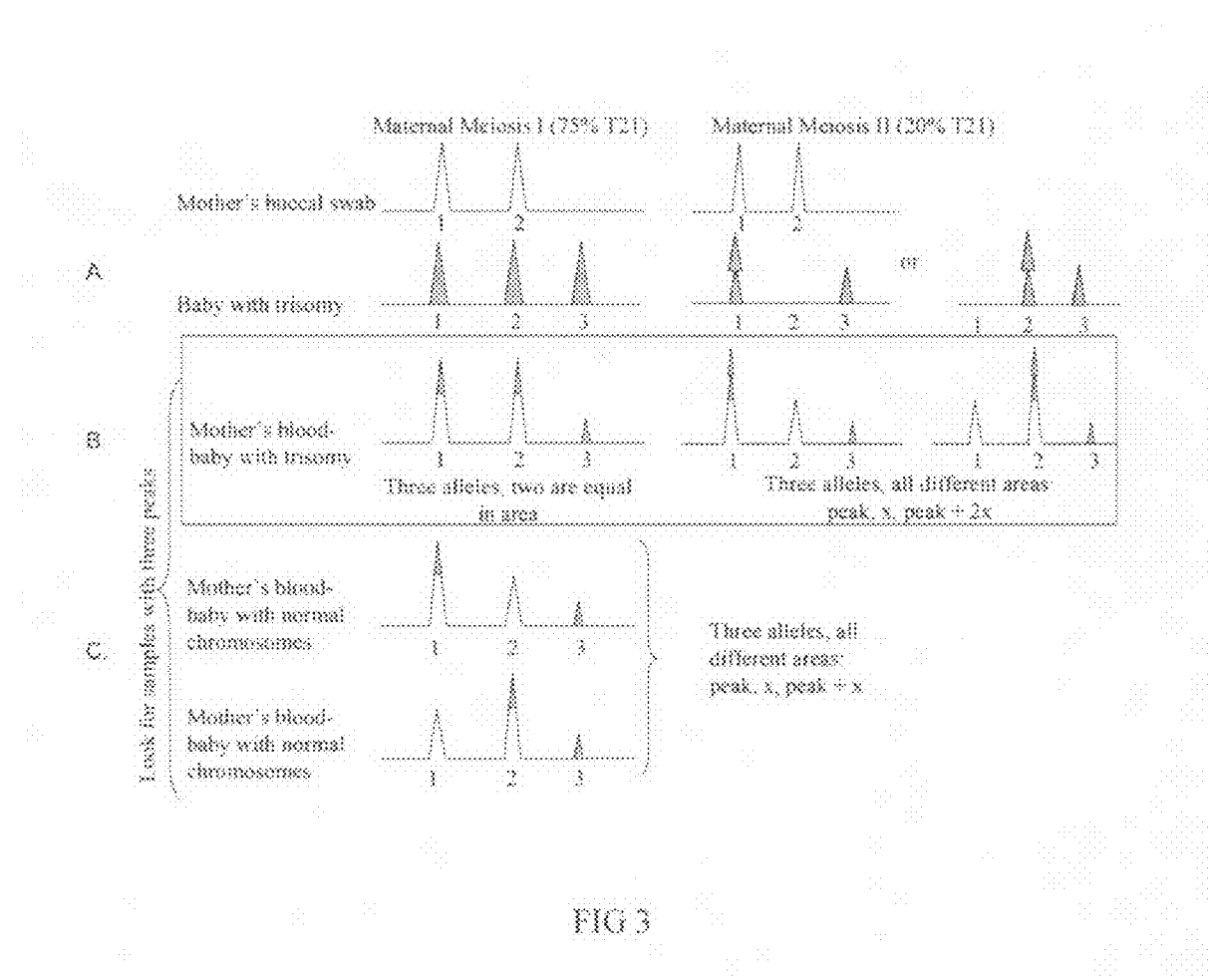
FIG. 3 depicts an example of a constant denaturant capillary electrophoresis electropherogram output.

A blinded study is performed where the goal is to detect 20 known trisomy 21 fetuses by assaying maternal serum from 40 patients (previously determined by amniocentesis or CVS) (see FIG. 3).

FIG. 3 depicts an example of a CDCE electropherogram output with the peaks at full scale. FIG. 3A depicts a sample from maternal buccal swab. Markers exhibiting two alleles are pursued. A baby with trisomy is expected to show either three alleles, evident by three peaks in a 1:1:1 ratio or two alleles in a 2:1 ratio. FIG. 3B depicts a sample from maternal serum. Markers exhibiting three alleles are informative. Maternal serum from a woman carrying a baby with trisomy is expected to exhibit three alleles, evident by two equal peaks with a third smaller peak if the trisomy occurred during meiosis I (75% of T21 cases) or three alleles with different areas if the trisomy occurred during meiosis II (20% of T21 cases) where areas are: peak, x, and peak+2x. FIG. 3C depicts analysis of a sample from maternal serum. Markers exhibiting three alleles are informative. Maternal serum from a woman with a normal baby with three alleles has three different areas where areas are: peak, x, and peak+x.

Interpretation of Results

For the case of the minimum heterozygosity, where both SNP1 and SNP2 are heterozygous at their respective loci at a rate of 25%, if 96 tandem SNPs are assayed, an average of 43 markers (44.5%) are expected to be heterozygous (two haplotypes) in the mother. The mother's expected heterozygosity is calculated using the following formula:

$$H = 1 - \Sigma p_i^2$$

for i=1 to k alleles where $p_i$=estimated allele frequency.

The allele frequencies at each SNP loci are expected to be 85% and 15% for the majority and minority alleles, respectively, assuming Hardy-Weinberg equilibrium. The desired third haplotype is expected to be present at an average of 6.4 markers (15%) of per maternal-fetal sample tested. Because most loci have a heterozygosity value greater than 25%, for every maternal-fetal sample tested using the panel of 96 tandem SNP assays, greater than about 6.4 markers are most informative. Thus, while a panel of 96 tandem SNPs may be used, 6 or 7 of those tandem SNPs may be informative for any one specific maternal-fetal sample tested, and a 'positive' result from any one of those tandem SNPs is informative.

Finally, in order to diagnose a trisomy, a "positive" tandem SNPs should be identified on both the p and the q arm of chromosome 21. Because of the comparative nature of the basic approach, the tandem SNP assay is predicted to have a detection rate of 95% (those that occur during maternal meiosis) for trisomy 21. If paternal samples are available, non-disjunctions that occur during paternal meiosis can also be detected. Thus, detection rates would be higher (about ~99%) with a 0% false positive rate.

Example 5

Tandem SNPs and Primers

Table 2 provides exemplary tandem SNPs of the invention and primers that can be used in the methods of the invention to detect the tandem SNPs. Certain embodiments of the present invention provide primers that can be used to amplify at least one of the SNPs. Certain embodiments of the present invention provide nucleic acid sequences that comprise at least one of the SNPs, e.g., at least one of the tandem SNPs.

TABLE 2

1) Whole sequence ::: rs432114 - rs365433 CC/CT/GC/GT

AACAAATCTTCATCTTGGAATAGCCTGTGAGAATGCCTAATCATCTACGAATgTTACTTT
GGCACCATCTACTGGACAgATTAAATAACAACCAACTCACTGTGGATTAGACCTACTTCT
ATTTCAG (SEQ ID NO: 1)

```
OLIGO          start len    tm     gc %   any   3'    seq (SEQ ID NOs: 2, 3)

LEFT PRIMER      20   20   55.08  45.00  3.00  2.00  ATAGCCTGTGAGAATGCCTA
RIGHT PRIMER    107   20   55.30  45.00  5.00  0.00  ATCCACAGTGAGTTGGTTGT
SEQUENCE SIZE: 127
INCLUDED REGION SIZE: 127

PRODUCT SIZE: 88, PAIR ANY COMPL: 5.00, PAIR 3' COMPL: 1.00
   1 AACAAATCTTCATCTTGGAATAGCCTGTGAGAATGCCTAATCATCTACGAATgTTACTTT
                         >>>>>>>>>>>>>>>>>>>>

61 GGCACCATCTACTGGACAgATTAAATAACAACCAACTCACTGTGGATTAGACCTACTTCT
                                          <<<<<<<<<<<<<<<<<<<<

121 ATTTCAG
```

2) Whole sequence ::: rs7277033-rs2110153 CC/CT/TC/TT

PCR did not work

TTCCTGGAAAACAAAAGTATTTCTTTCATAGCCCAGCTAGCAtGATAAATCAGCgAGTCA
GAATTCTAGCTTTGTTGTAAGGTT (SEQ ID NO: 4)

```
OLIGO          start len    tm     gc %   any   3'    seq (SEQ ID NOs: 5, 6)

LEFT PRIMER       2   20   51.63  30.00  5.00  3.00  TCCTGGAAAACAAAAGTATT
RIGHT PRIMER     84   21   51.36  33.33  4.00  0.00  AACCTTACAACAAAGCTAGAA
SEQUENCE SIZE: 84
INCLUDED REGION SIZE: 84

PRODUCT SIZE: 83, PAIR ANY COMPL: 3.00, PAIR 3' COMPL: 2.00
   1 TTCCTGGAAAACAAAAGTATTTCTTTCATAGCCCAGCTAGCAtGATAAATCAGCgAGTCA
       >>>>>>>>>>>>>>>>>>>>

61 GAATTCTAGCTTTGTTGTAAGGTT
          <<<<<<<<<<<<<<<<<<<<<
```

3) Whole sequence ::: rs2822654-rs1882882 AA/AG/CA/CG

CACTAAGCCTTGGGGATCCAGCTGCTTaAGGACTAAGACCgTATCTAGCTCCTTTTAGTA
TTTCCACAGCA (SEQ ID NO: 7)

```
OLIGO          start len    tm     gc %   any   3'    seq (SEQ ID NOs: 8, 9)

LEFT PRIMER       2   20   60.46  55.00  6.00  2.00  ACTAAGCCTTGGGGATCCAG
RIGHT PRIMER     71   21   54.78  38.10  3.00  0.00  TGCTGTGGAAATACTAAAGG
```

TABLE 2-continued

```
SEQUENCE SIZE: 71
INCLUDED REGION SIZE: 71

PRODUCT SIZE: 70, PAIR ANY COMPL: 4.00, PAIR 3' COMPL: 0.00
   1 CACTAAGCCTTGGGGATCCAGCTGCTTaAGGACTAAGACCgTATCTAGCTCCTTTTAGTA
     >>>>>>>>>>>>>>>>>>>>                                <<<<<<<<<

61 TTTCCACAGCA
     <<<<<<<<<<<

4) Whole sequence ::: rs368657-rs376635 AA/AG/GA/GG

TCCTCCAGAGGTAATCCTGTGATCAGCACTAACaCCACATACCAGCCCTTTCATCAGCTT
GTTGGAGAAGCATCTTTACTTCCCgCCAAGCAGTGACCTagataccatctcacaccagtt
agaatcaggatcattaaaaagtcaagaaaaaacag (SEQ ID NO: 10)

OLIGO           start len   tm    gc %   any   3'  seq (SEQ ID NOs: 11, 12)

LEFT PRIMER        3   20  55.20 50.00  5.00 3.00 CTCCAGAGGTAATCCTGTGA
RIGHT PRIMER     117   21  55.10 47.62  5.00 2.00 tggtgtgagatggtatctAGG
SEQUENCE SIZE: 155
INCLUDED REGION SIZE: 155

PRODUCT SIZE: 115, PAIR ANY COMPL: 3.00, PAIR 3' COMPL: 2.00
   1 TCCTCCAGAGGTAATCCTGTGATCAGCACTAACaCCACATACCAGCCCTTTCATCAGCTT
       >>>>>>>>>>>>>>>>>>>>

61 GTTGGAGAAGCATCTTTACTTCCCgCCAAGCAGTGACCTagataccatctcacaccagtt
                                               <<<<<<<<<<<<<<<<<<<<<

121 agaatcaggatcattaaaaagtcaagaaaaaacag

5) Whole sequence ::: rs2822731-rs2822732 AA/AG/GA/GG

TCCAAGTATAATCCATGAATCTTGTTTAAATATAGATCAAaTAAACCACTATACCAAAAA
CATCAAAAGACAACTGGGTAAATTTTTTAAATGACTAGCTATTTGATGTTAAgGAAGTAA
TGTTACTCTCTTATATACAATTTGAA (SEQ ID NO: 13)

OLIGO           start len   tm    gc %   any   3'  seq (SEQ ID NOs: 14, 15)

LEFT PRIMER        6   22  50.35 27.27  6.00 3.00 GTATAATCCATGAATCTTGTTT
RIGHT PRIMER     146   22  45.69 22.73  6.00 1.00 TTCAAATTGTATATAAGAGAGT
SEQUENCE SIZE: 146
INCLUDED REGION SIZE: 146

PRODUCT SIZE: 141, PAIR ANY COMPL: 4.00, PAIR 3' COMPL: 2.00
   1 TCCAAGTATAATCCATGAATCTTGTTTAAATATAGATCAAaTAAACCACTATACCAAAAA
          >>>>>>>>>>>>>>>>>>>>>>

61 CATCAAAAGACAACTGGGTAAATTTTTTAAATGACTAGCTATTTGATGTTAAgGAAGTAA

121 TGTTACTCTCTTATATACAATTTGAA
     <<<<<<<<<<<<<<<<<<<<<<

6) Whole sequence ::: rs6516899-rs455221 CC/CT/TC/TT

ATGGAACCGAAACTTCAAGTAGTTTCATAcGTATCACATTGACAGTTTTCTCTAAGTTTT
CtGGTCTTATGACTCGTTGTTTCATTATTAAAACTGTGCCAGTGTATGCATAGGGCTTAG
AAATTTTTTAAT (SEQ ID NO: 16)

OLIGO           start len   tm    gc %   any   3'  seq (SEQ ID NOs: 17, 18)

LEFT PRIMER        1   18  53.87 38.89  4.00 3.00 ATGGAACCGAAACTTCAA
RIGHT PRIMER      91   22  52.84 27.27  5.00 1.00 TTAATAATGAAACAACGAGTCA
SEQUENCE SIZE: 132
INCLUDED REGION SIZE: 132

PRODUCT SIZE: 91, PAIR ANY COMPL: 4.00, PAIR 3' COMPL: 0.00
   1 ATGGAACCGAAACTTCAAGTAGTTTCATAcGTATCACATTGACAGTTTTCTCTAAGTTTT
     >>>>>>>>>>>>>>>>>>

61 CtGGTCTTATGACTCGTTGTTTCATTATTAAAACTGTGCCAGTGTATGCATAGGGCTTAG
                <<<<<<<<<<<<<<<<<<<<<<

121 AAATTTTTTAAT
```

TABLE 2-continued

7) Whole sequence ::: rs7275381-rs12627144 GA/GG/TA/TG

```
acaggatccttcctgaagacaccaccttggggagggtgaagGataaagaatttgatcaga
aatcaagggtggtgagatacatgttaaggatgaataaactggccttttaggattcttgct
aaaAttagacaatgcagaggcaaccacagagtccaag (SEQ ID NO: 19)
```

| OLIGO | start | len | tm | gc % | any | 3' | seq (SEQ ID NOs: 20, 21) |
|---|---|---|---|---|---|---|---|
| LEFT PRIMER | 10 | 19 | 55.53 | 47.37 | 4.00 | 0.00 | ttcctgaagacaccacctt |
| RIGHT PRIMER | 157 | 18 | 54.94 | 55.56 | 3.00 | 2.00 | cttggactctgtggttgc |

SEQUENCE SIZE: 157
INCLUDED REGION SIZE: 157

PRODUCT SIZE: 148, PAIR ANY COMPL: 5.00, PAIR 3' COMPL: 1.00

```
  1 acaggatccttcctgaagacaccaccttggggagggtgaagGataaagaatttgatcaga
                >>>>>>>>>>>>>>>>>>>

61 aatcaagggtggtgagatacatgttaaggatgaataaactggccttttaggattcttgct 121 aaaAttagacaatgcagaggcaaccacagagtccaag
                   <<<<<<<<<<<<<<<<<<
```

8) Whole sequence ::: rs1999288-rs208897 CC/CT/TC

```
AATTTCCATTAAATCTTGTTCGTTGCTTTACTGAGGCACTGAAGTTACCAATGTTcCACT
GGTTGACCTGCGGGGCTATCTCTAGGTTATGTTACTCCAGAAAATGAATTGTGTATAAAA
GAGGCCTTGGAGGAAGGCGTTTTATTCaCATCAGTTGTTTTGCACATTGCTTA
(SEQ ID NO: 22)
```

| OLIGO | start | len | tm | gc % | any | 3' | seq (SEQ ID NOs: 23, 24) |
|---|---|---|---|---|---|---|---|
| LEFT PRIMER | 30 | 20 | 54.40 | 50.00 | 4.00 | 2.00 | ACTGAGGCACTGAAGTTACC |
| RIGHT PRIMER | 173 | 20 | 54.96 | 35.00 | 4.00 | 0.00 | TAAGCAATGTGCAAAACAAC |

SEQUENCE SIZE: 173
INCLUDED REGION SIZE: 173

PRODUCT SIZE: 144, PAIR ANY COMPL: 4.00, PAIR 3' COMPL: 0.00

```
  1 AATTTCCATTAAATCTTGTTCGTTGCTTTACTGAGGCACTGAAGTTACCAATGTTcCACT
                              >>>>>>>>>>>>>>>>>>>>

61 GGTTGACCTGCGGGGCTATCTCTAGGTTATGTTACTCCAGAAAATGAATTGTGTATAAAA

121 GAGGCCTTGGAGGAAGGCGTTTTATTCaCATCAGTTGTTTTGCACATTGCTTA
                                <<<<<<<<<<<<<<<<<<<<
```

9) Whole sequence ::: rs1475881-rs7275487 CA/CG/GA/GG

PCR did not work

```
TCGGTTTCAGCAGGAAAGTTATTTTTAATAACTTCCCTGTATTTcTTGGTTTCAGTTATTAATT
AACTCATTAATGCTAAACTTTGTGATCCTAGGTTAAAAAACATATTCAAGATAGCTTCAGAATG
TTTGGTATACAAgTAGGTCTGGCTAAATATAAGTGTTAGCTTT CTCAAGCATC TAAATGCTG
G (SEQ ID NO: 25)
```

| OLIGO | start | len | tm | gc % | any | 3' | seq (SEQ ID NOs: 26, 27) |
|---|---|---|---|---|---|---|---|
| LEFT PRIMER | 10 | 20 | 48.49 | 25.00 | 5.00 | 3.00 | GCAGGAAAGTTATTTTTAAT |
| RIGHT PRIMER | 179 | 21 | 54.70 | 38.10 | 4.00 | 1.00 | TGCTTGAGAAAGCTAACACTT |

SEQUENCE SIZE: 191
INCLUDED REGION SIZE: 191

PRODUCT SIZE: 170, PAIR ANY COMPL: 5.00, PAIR 3' COMPL: 2.00

```
  1 TCGGTTTCAGCAGGAAAGTTATTTTTAATAACTTCCCTGTATTTcTTGGTTTCAGTTATT
                >>>>>>>>>>>>>>>>>>>>

61 AATTAACTCATTAATGCTAAACTTTGTGATCCTAGGTTAAAAAACATATTCAAGATAGCT
```

TABLE 2-continued

```
121 TCAGAATGTTTGGTATACAAgTAGGTCTGGCTAAATATAAGTGTTAGCTTTCTCAAGCAT
                                      <<<<<<<<<<<<<<<<<<<<

181 CTAAATGCTGG

ALTERNATIVE:: (LESS THAN 5 bp APART)

AAGTTATTTTTAATAACTTCCCTGTATTTcTTGGTTTCAGTTATTAATTAACTCATTAAT
GCTAAACTTTGTGATCCTAGGTTAAAAAACATATTCAAGATAGCTTCAGAATGTTTGGTA
TACAAgTAGGTCTGGCTAAATATAAGTGTTAGCTTTCTCAAGCATC
(SEQ ID NO: 28)

OLIGO          start len   tm    gc %   any    3'  seq (SEQ ID NOs: 29, 30)

LEFT PRIMER       6   20  47.68  25.00  6.00  0.00 ATTTTTAATAACTTCCCTGT
RIGHT PRIMER    148   20  49.30  40.00  4.00  0.00 CACTTATATTTAGCCAGACC
SEQUENCE SIZE: 166
INCLUDED REGION SIZE: 166

PRODUCT SIZE: 143, PAIR ANY COMPL: 4.00, PAIR 3' COMPL: 1.00
   1 AAGTTATTTTTAATAACTTCCCTGTATTTcTTGGTTTCAGTTATTAATTAACTCATTAAT
         >>>>>>>>>>>>>>>>>>>>

61 GCTAAACTTTGTGATCCTAGGTTAAAAAACATATTCAAGATAGCTTCAGAATGTTTGGTA

121 TACAAgTAGGTCTGGCTAAATATAAGTGTTAGCTTTCTCAAGCATC
            <<<<<<<<<<<<<<<<<<<<

10) Whole sequence ::: rs1735976-rs2827016 AA/AC/GA/GC

ATTCATTGTGTAGAAAGTGCCTGACTCAGTGTTTGGAAATTGTCTGACTTTTCCTCATAT
aTAGTGTGGTTTCATGTTATTGTATATAAGAaCTGACATGAACTCTGTTTACAATAATCT
CCCAGTGCCATAAAGACCATAATAAATAATAT (SEQ ID NO: 31)

OLIGO          start len   tm    gc %   any    3'  seq (SEQ ID NOs: 32, 33)

LEFT PRIMER      27   20  54.11  40.00  4.00  1.00 CAGTGTTTGGAAATTGTCTG
RIGHT PRIMER    129   20  55.17  45.00  3.00  2.00 GGCACTGGGAGATTATTGTA
SEQUENCE SIZE: 152
INCLUDED REGION SIZE: 152

PRODUCT SIZE: 103, PAIR ANY COMPL: 5.00, PAIR 3' COMPL: 1.00
   1 ATTCATTGTGTAGAAAGTGCCTGACTCAGTGTTTGGAAATTGTCTGACTTTTCCTCATAT
                                >>>>>>>>>>>>>>>>>>>>

61 aTAGTGTGGTTTCATGTTATTGTATATAAGAaCTGACATGAACTCTGTTTACAATAATCT
                                                   <<<<<<<<<<

121 CCCAGTGCCATAAAGACCATAATAAATAATAT
        <<<<<<<<<<

2nd group of primers

11) Whole sequence ::: rs447349-rs2824097 CT/TC/TT (156 long)

CACTGGGTCCTGTTGTTAAGTACACATAATACCAcaCAGGAGAAAATCAGGCTAATTGTA
AATGGGCAACCTACTTAATTGTTTCATTAAAAAGCATACAGATTACATTTACACTAtAGC
TAGTCTTGTTTGTTTTTTTATTTTGCAAAAGTAATTACGGCCC (SEQ ID NO: 34)

OLIGO          start len   tm    gc %   any    3'  seq (SEQ ID NOs: 35, 36)

LEFT PRIMER       8   20  47.79  35.00  6.00  2.00 TCCTGTTGTTAAGTACACAT
RIGHT PRIMER    163   18  53.29  44.44  8.00  2.00 GGGCCGTAATTACTTTTG
SEQUENCE SIZE: 163
INCLUDED REGION SIZE: 163

PRODUCT SIZE: 156, PAIR ANY COMPL: 5.00, PAIR 3' COMPL: 1.00
   1 CACTGGGTCCTGTTGTTAAGTACACATAATACCAcaCAGGAGAAAATCAGGCTAATTGTA
           >>>>>>>>>>>>>>>>>>>>

61 AATGGGCAACCTACTTAATTGTTTCATTAAAAAGCATACAGATTACATTTACACTAtAGC
```

TABLE 2-continued

```
121 TAGTCTTGTTTGTTTTTTTATTTTGCAAAAGTAATTACGGCCC
              <<<<<<<<<<<<<<<<<<
```

12) Whole sequence ::: rs418989-rs13047336 AC/AT/CC

```
CTACTCAGTAGGCACTTTGTGTCTAGAAACTTCTGTGTCAACgGTTTTCCCTCTCTGG
AATTCaTCAGGACAGAAGTGATTGGTGTGGTGGAAGAGGGTTGTGSTA
(SEQ ID NO: 37)
```

OLIGO          start len   tm     gc %  any   3'   seq (SEQ ID NOs: 38, 39)

LEFT PRIMER      3    21  54.50  47.62  5.00  3.00 ACTCAGTAGGCACTTTGTGTC
RIGHT PRIMER    97    18  54.95  50.00  2.00  0.00 TCTTCCACCACACCAATC
SEQUENCE SIZE: 108
INCLUDED REGION SIZE: 108

PRODUCT SIZE: 95, PAIR ANY COMPL: 5.00, PAIR 3' COMPL: 2.00
```
  1 CTACTCAGTAGGCACTTTGTGTCTAGAAACTTCTGTGTCAACgGTTTTCCCTCTCTGG
    >>>>>>>>>>>>>>>>>>>>>

61 AATTCaTCAGGACAGAAGTGATTGGTGTGGTGGAAGAGGGTTGTGSTA
                                    <<<<<<<<<<<<<<<<<<
```

13) Whole sequence ::: rs987980-rs987981 AG/GG/GT

```
TGGCTTTTCAAAGGTAAAATTTACTaAGTGTATTAATATTTTACCAATTTCCAGCCAGGA
GAGTATGAATGTTGCATTATTACATTGCTTTGAAACAAAGCATTAgTCTTAATTCAGAAG
TTTAAATTCAGATGTTAACGTTGC (SEQ ID NO: 40)
```

OLIGO          start len   tm     gc %  any   3'   seq (SEQ ID NOs: 41, 42)

LEFT PRIMER      1    19  53.67  31.58  6.00  2.00 TGGCTTTTCAAAGGTAAAA
RIGHT PRIMER   144    21  54.59  33.33  6.00  3.00 GCAACGTTAACATCTGAATTT
SEQUENCE SIZE: 144
INCLUDED REGION SIZE: 144

PRODUCT SIZE: 144, PAIR ANY COMPL: 6.00, PAIR 3' COMPL: 3.00
```
  1 TGGCTTTTCAAAGGTAAAATTTACTaAGTGTATTAATATTTTACCAATTTCCAGCCAGGA
    >>>>>>>>>>>>>>>>>>>

61 GAGTATGAATGTTGCATTATTACATTGCTTTGAAACAAAGCATTAgTCTTAATTCAGAAG

121 TTTAAATTCAGATGTTAACGTTGC
         <<<<<<<<<<<<<<<<<<<<<
```

14) Whole sequence ::: rs4143392-rs4143391 CA/CG/GA/GG

```
TAAGTATTGAAGAAAGGAGAATTTAAATTACTTCATATACctgataaaggaaaacatata
CAAGGCAAATAAACATCTTAGATCATGACATATAAAATAATAGATTATTA
(SEQ ID NO: 43)
```

OLIGO          start len   tm     gc %  any   3'   seq (SEQ ID NOs: 44, 45)

LEFT PRIMER      7    20  49.56  25.00  4.00  4.00 TTGAAGAAAGGAGAATTTAA
RIGHT PRIMER    98    22  45.86  22.73  6.00  3.00 ATTTTATATGTCATGATCTAAG
SEQUENCE SIZE: 110
INCLUDED REGION SIZE: 110

PRODUCT SIZE: 92, PAIR ANY COMPL: 4.00, PAIR 3' COMPL: 1.00
```
  1 TAAGTATTGAAGAAAGGAGAATTTAAATTACTTCATATACctgataaaggaaaacatata
          >>>>>>>>>>>>>>>>>>>>

61 CAAGGCAAATAAACATCTTAGATCATGACATATAAAATAATAGATTATTA
                   <<<<<<<<<<<<<<<<<<<<<
```

15) Whole sequence ::: rs1691324-rs13050434 CG/TA/TG (4 bp apart for right primer)
```
TGCAGAGATTACAGGTGTGAGCCACCGTGCCCAGCCTCATAACcGTTTCAACTACTTTTT
CACTTGACAAGCAGATGTGAAGTTAACAAAGTCACCCATATTTGAAATAAAGATAGTATA
TTCCTGGGGtAGGCAGAGGCAGTTGAGGATCATGAAATAACTATG (SEQ ID NO: 46)
```

OLIGO          start len   tm     gc %  any   3'   seq (SEQ ID NOs: 47, 48)

LEFT PRIMER      4    19  49.78  47.37  4.00  4.00 AGAGATTACAGGTGTGAGC
RIGHT PRIMER   153    19  54.61  47.37  4.00  0.00 ATGATCCTCAACTGCCTCT

TABLE 2-continued

```
SEQUENCE SIZE: 165
INCLUDED REGION SIZE: 165

PRODUCT SIZE: 150, PAIR ANY COMPL: 4.00, PAIR 3' COMPL: 2.00
   1 TGCAGAGATTACAGGTGTGAGCCACCGTGCCCAGCCTCATAACcGTTTTCAACTACTTTTT
         >>>>>>>>>>>>>>>>>>>>

61 CACTTGACAAGCAGATGTGAAGTTAACAAAGTCACCCATATTTGAAATAAAGATAGTATA

121 TTCCTGGGGtAGGCAGAGGCAGTTGAGGATCATGAAATAACTATG
                   <<<<<<<<<<<<<<<<<<<<

16) Whole sequence ::: rs11909758-rs9980111 (159 bp long) AG/AT/GT

TGCAATGAAACTCAAAAGAGAAAAGTTAACAGGTGCAAaAGGTAGTTTTATTATAAAAGG
AGGGTAGGCAACAAGAATATGTTTAATTTTTCTTCCTTTTCATGAGTAAGGACAAGAGTg
TCATATATGTGaatattttttatttaattttaaGTAGAAATCTGTTTTTAAAATATGGG
(SEQ ID NO: 49)

OLIGO           start len    tm     gc %  any   3'  seq (SEQ ID NOs: 50, 51)

LEFT PRIMER        6   20  49.91  30.00  3.00 0.00 TGAAACTCAAAAGAGAAAAG
RIGHT PRIMER     164   20  42.77  20.00  6.00 4.00 ACAGATTTCTACttaaaatt
SEQUENCE SIZE: 178
INCLUDED REGION SIZE: 178

PRODUCT SIZE: 159, PAIR ANY COMPL: 6.00, PAIR 3' COMPL: 3.00
   1 TGCAATGAAACTCAAAAGAGAAAAGTTAACAGGTGCAAaAGGTAGTTTTATTATAAAAGG
            >>>>>>>>>>>>>>>>>>>>

61 AGGGTAGGCAACAAGAATATGTTTAATTTTTCTTCCTTTTCATGAGTAAGGACAAGAGTg

121 TCATATATGTGaatattttttatttaattttaaGTAGAAATCTGTTTTTAAAATATGGG
                    <<<<<<<<<<<<<<<<<<<<

17) Whole sequence ::: rs854613-rs854614 AA/AG/TG

CCACCATTCATCAAAACTTTGATACTGGACTCAATTGTGAATTTGaCTTGAAATTTGATA
ATGCTTTTGTTTTACTgTTCTGCTCAGCAAAATAGTACATGT (SEQ ID NO: 52)

OLIGO           start len    tm     gc %  any   3'  seq (SEQ ID NOs: 53, 54)

LEFT PRIMER       12   20  49.40  35.00  6.00 1.00 CAAAACTTTGATACTGGACT
RIGHT PRIMER     102   19  46.05  31.58  6.00 1.00 ACATGTACTATTTTGCTGA
SEQUENCE SIZE: 102
INCLUDED REGION SIZE: 102

PRODUCT SIZE: 91, PAIR ANY COMPL: 5.00, PAIR 3' COMPL: 1.00
   1 CCACCATTCATCAAAACTTTGATACTGGACTCAATTGTGAATTTGaCTTGAAATTTGATA
                  >>>>>>>>>>>>>>>>>>>>

61 ATGCTTTTGTTTTACTgTTCTGCTCAGCAAAATAGTACATGT
                   <<<<<<<<<<<<<<<<<<<

3rd group --- order primers from 18-25

18) Whole sequence ::: rs2826225-rs2826226 AA/GA/GC

GCCTGCATAAAGTGAGGATGGTGTAGTAATTGGGTATCTCCAGTTATAAACACAAaAAGC
ATGATAGAGCTGGGAcTGTGATTGCAGGAAAGCAATAGTCACTCCAAAAGGAGATCCTCA
TGATATGAATACGGAAGAAACAATATTTCCTGCTAATGTAGTAGCC (SEQ ID NO: 55)

OLIGO           start len    tm     gc %  any   3'  seq (SEQ ID NOs: 56, 57)

LEFT PRIMER        2   20  58.17  50.00  4.00 0.00 CCTGCATAAAGTGAGGATGG
RIGHT PRIMER     120   21  59.27  47.62  6.00 0.00 TGAGGATCTCCTTTTGGAGTG
SEQUENCE SIZE: 166
INCLUDED REGION SIZE: 166

PRODUCT SIZE: 119, PAIR ANY COMPL: 6.00, PAIR 3' COMPL: 3.00
   1 GCCTGCATAAAGTGAGGATGGTGTAGTAATTGGGTATCTCCAGTTATAAACACAAaAAGC
         >>>>>>>>>>>>>>>>>>>>
```

TABLE 2-continued

```
 61 ATGATAGAGCTGGGAcTGTGATTGCAGGAAAGCAATAGTCACTCCAAAAGGAGATCCTCA
                              <<<<<<<<<<<<<<<<<<<<

121 TGATATGAATACGGAAGAAACAATATTTCCTGCTAATGTAGTAGCC
```

19) Whole sequence ::: rs2826842-rs232414 CA/CG/TA/TG

```
GCAAAGGGGTACTCTATGTAATGAAcATgacctggcagtactgacatctcctgagggact
gttagaagtgcagactcttgtatcttttctcaagtctatgaaatctagacttcattttaa
caagatgacccgatatttacatacacattaaagt (SEQ ID NO: 58)
```

| OLIGO | start | len | tm | gc % | any | 3' | seq (SEQ ID NOs: 59, 60) |
|---|---|---|---|---|---|---|---|
| LEFT PRIMER | 1 | 20 | 52.04 | 45.00 | 4.00 | 2.00 | GCAAAGGGGTACTCTATGTA |
| RIGHT PRIMER | 135 | 20 | 53.29 | 35.00 | 4.00 | 3.00 | tatcgggtcatcttgttaaa |

SEQUENCE SIZE: 154
INCLUDED REGION SIZE: 154

PRODUCT SIZE: 135, PAIR ANY COMPL: 3.00, PAIR 3' COMPL: 2.00

```
  1 GCAAAGGGGTACTCTATGTAATGAAcATgacctggcagtactgacatctcctgagggact
    >>>>>>>>>>>>>>>>>>>>

61 gttagaagtgcagactcttgtatcttttctcaagtctatgaaatctagacttcattttaa
                                                         <<<<<

121 caagatgacccgatatttacatacacattaaagt
    <<<<<<<<<<<<<<<
```

20) Whole sequence ::: rs1980969-rs1980970 AA/AG/TA/TG

```
GTATCTAACAAAGCTCTGTCCAAAATTTTGAATTTCTCGTTAAAaGCATCATGATTATAG
AACAGAGGTTACAATCAATTATTCAGTCACACAATCACTCTCATCAGTCATTAAGGTGCg
TACCTGGTGTTCCAGTTATTCAGTGTGGTATAACAAACTACCTGGAACTTAATG
(SEQ ID NO: 61)
```

| OLIGO | start | len | tm | gc % | any | 3' | seq (SEQ ID NOs: 62, 63) |
|---|---|---|---|---|---|---|---|
| LEFT PRIMER | 4 | 22 | 56.88 | 36.36 | 8.00 | 2.00 | TCTAACAAAGCTCTGTCCAAAA |
| RIGHT PRIMER | 148 | 21 | 56.12 | 42.86 | 3.00 | 1.00 | CCACACTGAATAACTGGAACA |

SEQUENCE SIZE: 174
INCLUDED REGION SIZE: 174

PRODUCT SIZE: 145, PAIR ANY COMPL: 4.00, PAIR 3' COMPL: 1.00

```
  1 GTATCTAACAAAGCTCTGTCCAAAATTTTGAATTTCTCGTTAAAaGCATCATGATTATAG
       >>>>>>>>>>>>>>>>>>>>>>

61 AACAGAGGTTACAATCAATTATTCAGTCACACAATCACTCTCATCAGTCATTAAGGTGCg

121 TACCTGGTGTTCCAGTTATTCAGTGTGGTATAACAAACTACCTGGAACTTAATG
            <<<<<<<<<<<<<<<<<<<<<
```

4th group

21) Whole sequence ::: rs189900-rs2221492

```
AGAGTGGTTAAGTGACTTGATCAATTCCTCA GGTGGGGATTCAAGCTCTTAAAGCTGTAG
ACTATGTCGTCCAAACAAAcACTGACATGAATATGACTTCCAATAGGCAAGAAAAGAGGC
CTAGGTCgAGATACTGCAAGACATGCAAGCAATCTAGTAATGGCATAAAACCTGCTATCC
GAATTGGCTAAAATTATGTATT (SEQ ID NO: 64)
```

| OLIGO | start | len | tm | gc % | any | 3' | seq (SEQ ID NOs: 65, 66) |
|---|---|---|---|---|---|---|---|
| LEFT PRIMER | 32 | 20 | 59.13 | 50.00 | 4.00 | 2.00 | GGTGGGGATTCAAGCTCTTA |
| RIGHT PRIMER | 180 | 22 | 59.38 | 40.91 | 5.00 | 3.00 | GGATAGCAGGTTTTATGCCATT |

SEQUENCE SIZE: 202
INCLUDED REGION SIZE: 202

PRODUCT SIZE: 149, PAIR ANY COMPL: 4.00, PAIR 3' COMPL: 1.00

```
  1 AGAGTGGTTAAGTGACTTGATCAATTCCTCAGGTGGGGATTCAAGCTCTTAAAGCTGTAG
                                   >>>>>>>>>>>>>>>>>>>>

61 ACTATGTCGTCCAAACAAAcACTGACATGAATATGACTTCCAATAGGCAAGAAAAGAGGC

121 CTAGGTCgAGATACTGCAAGACATGCAAGCAATCTAGTAATGGCATAAAACCTGCTATCC
                                         <<<<<<<<<<<<<<<<<<<<<<

181 GAATTGGCTAAAATTATGTATT
```

TABLE 2-continued

22) Whole sequence ::: rs2827920-rs2827921

TTCTTTCTCACACAATGGGTTCCATTCCCACTACTACTCCATTCAAATTGAAGTGCCTTC
aATGATTATTAAAAAACTCTCTTTAAAATAGCTCAcGTAACCTTACATCCTTTGACTGAG
GCTCAACTCATGTCAATGCTTCAGTATCAACTTTTC (SEQ ID NO: 67)

| OLIGO | start | len | tm | gc % | any | 3' | seq (SEQ ID NOs: 68, 69) |
|---|---|---|---|---|---|---|---|
| LEFT PRIMER | 14 | 21 | 59.93 | 47.62 | 7.00 | 0.00 | AATGGGTTCCATTCCCACTAC |
| RIGHT PRIMER | 125 | 20 | 58.96 | 50.00 | 7.00 | 1.00 | TGAGCCTCAGTCAAAGGATG |

SEQUENCE SIZE: 156
INCLUDED REGION SIZE: 156

PRODUCT SIZE: 112, PAIR ANY COMPL: 4.00, PAIR 3' COMPL: 1.00
```
  1 TTCTTTCTCACACAATGGGTTCCATTCCCACTACTACTCCATTCAAATTGAAGTGCCTTC
                    >>>>>>>>>>>>>>>>>>>>>

61 aATGATTATTAAAAAACTCTCTTTAAAATAGCTCAcGTAACCTTACATCCTTTGACTGAG
                                         <<<<<<<<<<<<<<

121 GCTCAACTCATGTCAATGCTTCAGTATCAACTTTTC
    <<<<<
```

23) Whole sequence ::: rs198047-rs2827935

ATTTGTAATAACATTTAGTAAGTATTTATTTGAGGAGTTTGAATTTTGTTCTTGTTTATC
TTGTTCTCTTTCTTcGTAGATTAGTTGGTGTTAACATCAATAGGATAACCCTTTCTTTCA
GCATATGTGAATGAAATaAACCAATTATTGCCACTTTCCAGGTTAACCAGAATATACATA
GATACGAGGACAGTGGACTGTT (SEQ ID NO: 70)

| OLIGO | start | len | tm | gc % | any | 3' | seq (SEQ ID NOs: 71, 72) |
|---|---|---|---|---|---|---|---|
| LEFT PRIMER | 30 | 22 | 56.07 | 31.82 | 4.00 | 1.00 | TTGAGGAGTTTGAATTTTGTTC |
| RIGHT PRIMER | 164 | 20 | 57.22 | 40.00 | 3.00 | 1.00 | AACCTGGAAAGTGGCAATAA |

SEQUENCE SIZE: 202
INCLUDED REGION SIZE: 202

PRODUCT SIZE: 135, PAIR ANY COMPL: 3.00, PAIR 3' COMPL: 2.00
```
  1 ATTTGTAATAACATTTAGTAAGTATTTATTTGAGGAGTTTGAATTTTGTTCTTGTTTATC
                                  >>>>>>>>>>>>>>>>>>>>>>

61 TTGTTCTCTTTCTTcGTAGATTAGTTGGTGTTAACATCAATAGGATAACCCTTTCTTTCA

121 GCATATGTGAATGAAATaAACCAATTATTGCCACTTTCCAGGTTAACCAGAATATACATA
                                  <<<<<<<<<<<<<<<<<<<<

181 GATACGAGGACAGTGGACTGTT
```

24) Whole sequence ::: rs9978999-rs9979175 tagggcagagagagcaagcaagctctctaccttctcatataagggcactaatcccaccat
gaaggcgccactgtcatgacCtgattatgtcacaaagaccccggggcaaatattaccact
Gtgaggagtacagttttagcatgtgaattttggaagaacacaaacatttag
(SEQ ID NO: 73)

| OLIGO | start | len | tm | gc % | any | 3' | seq (SEQ ID NOs: 74, 75) |
|---|---|---|---|---|---|---|---|
| LEFT PRIMER | 14 | 21 | 58.50 | 52.38 | 4.00 | 0.00 | gcaagcaagctctctaccttc |
| RIGHT PRIMER | 160 | 22 | 59.98 | 36.36 | 4.00 | 2.00 | tgttcttccaaaattcacatgc |

SEQUENCE SIZE: 171
INCLUDED REGION SIZE: 171

PRODUCT SIZE: 147, PAIR ANY COMPL: 3.00, PAIR 3' COMPL: 0.00
```
  1 tagggcagagagagcaagcaagctctctaccttctcatataagggcactaatcccaccat
                  >>>>>>>>>>>>>>>>>>>>>

61 gaaggcgccactgtcatgacCtgattatgtcacaaagaccccggggcaaatattaccact

121 Gtgaggagtacagttttagcatgtgaattttggaagaacacaaacatttag
                      <<<<<<<<<<<<<<<<<<<<<<
```

25) Whole sequence ::: rs1034346-rs12481852

ATTCTAATTTTAAATATCATTGATGTAGAACATTCTATTTCACTATTCCTTCATTTTATT
aTTATGGGAAATTATATACAGTTCTCCAGATTTTTAAAGCCTTGCTAACATGTTTTAAGT

TABLE 2-continued

```
CACACAAATATTCTcCTGTGGGAAAATGACAGTAATTTAGTGTGCAACAATTATATAGAA
CTATTTTTCAAACTT (SEQ ID NO: 76)

OLIGO          start  len  tm     gc %   any   3'    seq (SEQ ID NOs: 77, 78)

LEFT PRIMER     37    21   50.04  23.81  2.00  0.00  ATTTCACTATTCCTTCATTTT
RIGHT PRIMER   173    22   50.19  27.27  6.00  3.00  TAATTGTTGCACACTAAATTAC
SEQUENCE SIZE: 195
INCLUDED REGION SIZE: 195

PRODUCT SIZE: 137, PAIR ANY COMPL: 4.00, PAIR 3' COMPL: 2.00
   1 ATTCTAATTTTAAATATCATTGATGTAGAACATTCTATTTCACTATTCCTTCATTTTATT
                                              >>>>>>>>>>>>>>>>>>>>>

61 aTTATGGGAAATTATATACAGTTCTCCAGATTTTTAAAGCCTTGCTAACATGTTTTAAGT

121 CACACAAATATTCTcCTGTGGGAAAATGACAGTAATTTAGTGTGCAACAATTATATAGAA
                                     <<<<<<<<<<<<<<<<<<<<<

181 CTATTTTTCAAACTT
```

5<sup>th</sup> group

26) Whole sequence ::: rs7509629-rs2828358

```
ACTGTCATGGACTTAAACAATTGTCTTTGAATTGTCTTTTTTCATACTTTTATTTGCATC
TTTcCACTAAAAAGATGgCACAAAGTAATCCTAGTTTACATTTTTTACCATGTAATTCCA
TATTACTTTTTCCTGAAA (SEQ ID NO: 79)

OLIGO          start  len  tm     gc %   any   3'    seq (SEQ ID NOs: 80, 81)

LEFT PRIMER      1    20   50.46  35.00  4.00  0.00  ACTGTCATGGACTTAAACAA
RIGHT PRIMER   137    22   53.49  27.27  4.00  0.00  TTCAGGAAAAAGTAATATGGAA
SEQUENCE SIZE: 138
INCLUDED REGION SIZE: 138

PRODUCT SIZE: 137, PAIR ANY COMPL: 4.00, PAIR 3 COMPL: 0.00
   1 ACTGTCATGGACTTAAACAATTGTCTTTGAATTGTCTTTTTTCATACTTTTATTTGCATC
     >>>>>>>>>>>>>>>>>>>>

61 TTTcCACTAAAAAGATGgCACAAAGTAATCCTAGTTTACATTTTTTACCATGTAATTCCA
                                                              <<<<<

121 TATTACTTTTTCCTGAAA
     <<<<<<<<<<<<<<<<<
```

6<sup>th</sup> group

27) Whole sequence ::: rs4817013-rs7277036

```
aaagaaaaaaaagccacagaaatcagtcctagagaaaacCgatctatgagctgcctgaAa
ataattataaaataactatcataaaaatgcccagtgagatataagaaaacacagacaac
(SEQ ID NO: 82)

OLIGO          start  len  tm     gc %   any   3'    seq (SEQ ID NOs: 83, 84)

LEFT PRIMER      8    21   56.10  38.10  4.00  2.00  aaaaagccacagaaatcagtc
RIGHT PRIMER   107    22   55.60  36.36  4.00  2.00  ttcttatatctcactgggcatt
SEQUENCE SIZE: 119
INCLUDED REGION SIZE: 119

PRODUCT SIZE: 100, PAIR ANY COMPL: 5.00, PAIR 3' COMPL: 1.00
   1 aaagaaaaaaaagccacagaaatcagtcctagagaaaacCgatctatgagctgcctgaAa
             >>>>>>>>>>>>>>>>>>>>>

61 ataattataaaataactatcataaaaatgcccagtgagatataagaaaacacagacaac
                                    <<<<<<<<<<<<<<<<<<<<<<
```

28) Whole sequence ::: rs9981121-rs2829696

```
CAAGGTCAGAGAAGTTATCTTGGATGGTAGAAGAGAAGAAAGGAGAAGAAaGGATAAGCA
GAAAATCAAAAAGGGCATAAAAAAATTACTGGgGAAAATAATTCTTAGTCACTCACCATT
TCTTATGTTTGTGAAAACAGAAA (SEQ ID NO: 85)

OLIGO          start  len  tm     gc %   any   3'    seq (SEQ ID NOs: 86, 87)

LEFT PRIMER     22    22   56.24  45.45  2.00  0.00  GGATGGTAGAAGAGAAGAAAGG
RIGHT PRIMER   134    22   55.74  31.82  4.00  1.00  TCACAAACATAAGAAATGGTGA
SEQUENCE SIZE: 143
```

TABLE 2-continued

```
INCLUDED REGION SIZE: 143

PRODUCT SIZE: 113, PAIR ANY COMPL: 3.00, PAIR 3' COMPL: 0.00
   1 CAAGGTCAGAGAAGTTATCTTGGATGGTAGAAGAGAAGAAAGGAGAAGAAaGGATAAGCA
                     >>>>>>>>>>>>>>>>>>>>>

61 GAAAATCAAAAAGGGCATAAAAAAATTACTGGGgGAAAATAATTCTTAGTCACTCACCATT
                                                       <<<<<<<

121 TCTTATGTTTGTGAAAACAGAAA
        <<<<<<<<<<<<<<

29) Whole sequence ::: rs455921-rs2898102 gaccacaattcacaaatgcaaagatgcagaaccaacctaagtggccaCtgactaatgaga
ggataaagaagatgtggcatatataTatcagggactactactcagccattacaaggaaca
aaataatgtcttttgc (SEQ ID NO: 88)

OLIGO          start len    tm   gc %   any    3'  seq (SEQ ID NOs: 89, 90)

LEFT PRIMER      17   20  59.85  45.00  4.00  0.00 tgcaaagatgcagaaccaac
RIGHT PRIMER    123   22  59.63  36.36  2.00  1.00 tttttgttccttgtaatggctga
SEQUENCE SIZE: 136
INCLUDED REGION SIZE: 136

PRODUCT SIZE: 107, PAIR ANY COMPL: 5.00, PAIR 3' COMPL: 1.00
   1 gaccacaattcacaaatgcaaagatgcagaaccaacctaagtggccaCtgactaatgaga
                     >>>>>>>>>>>>>>>>>>>>

61 ggataaagaagatgtggcatatataTatcagggactactactcagccattacaaggaaca
                                                  <<<<<<<<<<<<<<<<<<<

121 aaataatgtcttttgc
        <<<

30) Whole sequence ::: rs2898102-rs458848 gaccacaattcacaaatgcaaagatgcagaaccaacctaagtggccactgactaatgaga
ggataaagaagatgtggcatatataCatcagggactactTctcagccattacaaggaaca
aaataatgtcttttgcaacaacttggatagagctggaggc (SEQ ID NO: 91)

OLIGO          start len    tm   gc %   any    3'  seq (SEQ ID NOs: 92, 93)

LEFT PRIMER      17   20  59.85  45.00  4.00  0.00 tgcaaagatgcagaaccaac
RIGHT PRIMER    160   21  59.86  52.38  4.00  3.00 gcctccagctctatccaagtt
SEQUENCE SIZE: 160
INCLUDED REGION SIZE: 160

PRODUCT SIZE: 144, PAIR ANY COMPL: 4.00, PAIR 3' COMPL: 3.00
   1 gaccacaattcacaaatgcaaagatgcagaaccaacctaagtggccactgactaatgaga
                     >>>>>>>>>>>>>>>>>>>>

61 ggataaagaagatgtggcatatataCatcagggactactTctcagccattacaaggaaca 121 aaataatgtcttttgcaacaacttggatagagctggaggc
                     <<<<<<<<<<<<<<<<<<<<<

31) Whole sequence ::: rs961301-rs2830208

AATCCTAGACCTTGGATTGCAAGAGACTCCTTAATATCTTCCCATGTCCACATTTcCTTC
ACATAGTTTGAATGTGGCTTCTATTATATACAGATACAAGATTCAAATCCAACCTCTAtG
ATGACTGGTCTTGTGAATAAGCAGAAGAGGCACTAACAAT (SEQ ID NO: 94)

OLIGO          start len    tm   gc %   any    3'  seq (SEQ ID NOs: 95, 96)

LEFT PRIMER      29   22  57.95  40.91  4.00  2.00 CCTTAATATCTTCCCATGTCCA
RIGHT PRIMER    160   22  57.35  40.91  3.00  0.00 ATTGTTAGTGCCTCTTCTGCTT
SEQUENCE SIZE: 160
INCLUDED REGION SIZE: 160
```

TABLE 2-continued

PRODUCT SIZE: 132, PAIR ANY COMPL: 3.00, PAIR 3' COMPL: 1.00
```
  1 AATCCTAGACCTTGGATTGCAAGAGACTCCTTAATATCTTCCCATGTCCACATTTcCTTC
                                 >>>>>>>>>>>>>>>>>>>>>

61 ACATAGTTTGAATGTGGCTTCTATTATATACAGATACAAGATTCAAATCCAACCTCTAtG

121 ATGACTGGTCTTGTGAATAAGCAGAAGAGGCACTAACAAT
                  <<<<<<<<<<<<<<<<<<<<
```

32) Whole sequence ::: rs2174536-rs458076

AAGAGAAGTGAGGTCAGCAGCTGCAAGCCACCTCCGTCATTTAGAAAAGCTTCaTGATGT
AGTGTGTCGTTTCGATGTGACACTGTCTCACAGAGTTAAAATGATGTtAAGGAACTGTTC
AATGGAAATTTAGAAATTTCTCTTTTTCTCAATTTTAGTGTA (SEQ ID NO: 97)

OLIGO          start len   tm    gc %   any    3'  seq (SEQ ID NOs: 98, 99)

LEFT PRIMER        3  20  57.31  55.00  5.00  5.00 GAGAAGTGAGGTCAGCAGCT
RIGHT PRIMER     136  22  53.92  27.27  6.00  2.00 TTTCTAAATTTCCATTGAACAG
SEQUENCE SIZE: 162
INCLUDED REGION SIZE: 162

PRODUCT SIZE: 134, PAIR ANY COMPL: 4.00, PAIR 3' COMPL: 2.00
```
  1 AAGAGAAGTGAGGTCAGCAGCTGCAAGCCACCTCCGTCATTTAGAAAAGCTTCaTGATGT
       >>>>>>>>>>>>>>>>>>>>

61 AGTGTGTCGTTTCGATGTGACACTGTCTCACAGAGTTAAAATGATGTtAAGGAACTGTTC
                                                         <<<<<<

121 AATGGAAATTTAGAAATTTCTCTTTTTCTCAATTTTAGTGTA
          <<<<<<<<<<<<<<<<
```

33) Whole sequence ::: rs432557-rs1012766

ATGGCTGAATAGTATTCCCTTGTGTATATATCTaTTTATCCTTTTATTCATTGATGGACA
CTTAGGCTGATTTTCTCTCTTCTCATGGCTGGCTTCTCATCACCCTTTGGTCCTCCTGTA
TCCTCgTGTAATAAAGCTCTTCCCCAATATCTCGATAGAT (SEQ ID NO: 100)

OLIGO          start len   tm    gc %   any    3'  seq (SEQ ID NOs: 101, 102)

LEFT PRIMER        3  22  57.77  45.45  9.00  0.00 GGCTGAATAGTATTCCCTTGTG
RIGHT PRIMER     155  20  59.22  50.00  4.00  2.00 TCGAGATATTGGGGAAGAGC
SEQUENCE SIZE: 160
INCLUDED REGION SIZE: 160

PRODUCT SIZE: 153, PAIR ANY COMPL: 5.00, PAIR 3' COMPL: 1.00
```
  1 ATGGCTGAATAGTATTCCCTTGTGTATATATCTaTTTATCCTTTTATTCATTGATGGACA
       >>>>>>>>>>>>>>>>>>>>>>

61 CTTAGGCTGATTTTCTCTCTTCTCATGGCTGGCTTCTCATCACCCTTTGGTCCTCCTGTA

121 TCCTCgTGTAATAAAGCTCTTCCCCAATATCTCGATAGAT
                   <<<<<<<<<<<<<<<<<<<<
```

34) Whole sequence ::: rs10222076-rs10222075 cattttaacttgatta cctccacaaagactattccagaataaggttatgttctgaggtat
tagggggttacAacttcaacatatgaattttgagtggacacaattcaacccatagcaCCTC
CGTGTAAGAGCTGGGAAGGGAAAGTGGCTAAGTTGTGCAAATGTGCACATTGGTTGGAGA
TGATTAACTTCTGGCATGT (SEQ ID NO: 103)

OLIGO          start len   tm    gc %   any    3'  seq (SEQ ID NOs: 104, 105)

LEFT PRIMER       17  22  58.32  45.45  4.00  2.00 cctccacaaagactattccaga
RIGHT PRIMER     146  20  60.76  55.00  4.00  2.00 CACTTTCCCTTCCCAGCTCT
SEQUENCE SIZE: 199
INCLUDED REGION SIZE: 199

PRODUCT SIZE: 130, PAIR ANY COMPL: 4.00, PAIR 3' COMPL: 3.00
```
  1 cattttaacttgattacctccacaaagactattccagaataaggttatgttctgaggtat
                   >>>>>>>>>>>>>>>>>>>>>>

61 tagggggttacAacttcaacatatgaattttgagtggacacaattcaacccatagcaCCTC

121 CGTGTAAGAGCTGGGAAGGGAAAGTGGCTAAGTTGTGCAAATGTGCACATTGGTTGGAGA
             <<<<<<<<<<<<<<<<<<<<

181 TGATTAACTTCTGGCATGT
```

TABLE 2-continued

35) Whole sequence ::: rs11088023-rs11088024 aggggaaattggcaatctgattctaaaattcataCggaaaaaaacaatggagttagaat
aactaaaacaagtccgaaaagaaaaagaaatggaggactaatgctacctgatttcaagt
cttatcTtataaatctacatcaataaaggacaagttg (SEQ ID NO: 106)

| OLIGO | start | len | tm | gc % | any | 3' | seq (SEQ ID NOs: 107, 108) |
|---|---|---|---|---|---|---|---|
| LEFT PRIMER | 6 | 20 | 54.34 | 35.00 | 7.00 | 3.00 | gaaattggcaatctgattct |
| RIGHT PRIMER | 157 | 21 | 51.94 | 33.33 | 5.00 | 0.00 | caacttgtcctttattgatgt |

SEQUENCE SIZE: 157
INCLUDED REGION SIZE: 157

PRODUCT SIZE: 152, PAIR ANY COMPL: 4.00, PAIR 3' COMPL: 0.00
```
  1 aggggaaattggcaatctgattctaaaattcataCggaaaaaaacaatggagttagaat
       >>>>>>>>>>>>>>>>>>>>

61 aactaaaacaagtccgaaaagaaaaagaaatggaggactaatgctacctgatttcaagt 121 cttatcTtataaatctacatcaataaaggacaagttg
                       <<<<<<<<<<<<<<<<<<<<<
```

36) Whole sequence ::: rs1011734-rs1011733

TCTGTGTTTGTCTATGTTGATAAAACATTGAAATGCCAaATAGCTCAAAGGTCATTCACT
TAAGAAATCTAAGTACTGATAACATCTTAGCCCCGATTCTTCATAGGCATTGTTAAGCCT
ATTATAATTTTGGTtCAGAGAGAAGGTAAACTATATTCCAGACAGGCATATAA
(SEQ ID NO: 109)

| OLIGO | start | len | tm | gc % | any | 3' | seq (SEQ ID NOs: 110, 111) |
|---|---|---|---|---|---|---|---|
| LEFT PRIMER | 12 | 22 | 50.06 | 22.73 | 6.00 | 2.00 | CTATGTTGATAAAACATTGAAA |
| RIGHT PRIMER | 167 | 20 | 51.09 | 40.00 | 4.00 | 2.00 | GCCTGTCTGGAATATAGTTT |

SEQUENCE SIZE: 173
INCLUDED REGION SIZE: 173

PRODUCT SIZE: 156, PAIR ANY COMPL: 5.00, PAIR 3' COMPL: 3.00
```
  1 TCTGTGTTTGTCTATGTTGATAAAACATTGAAATGCCAaATAGCTCAAAGGTCATTCACT
             >>>>>>>>>>>>>>>>>>>>>>

61 TAAGAAATCTAAGTACTGATAACATCTTAGCCCCGATTCTTCATAGGCATTGTTAAGCCT

121 ATTATAATTTTGGTtCAGAGAGAAGGTAAACTATATTCCAGACAGGCATATAA
                              <<<<<<<<<<<<<<<<<<<<
```

37) Whole sequence ::: rs2831244-rs9789838

TGCAGGGCATATAATCTAAGCTGTAAACGTCCTGTcAGAAGACAACATATTCATCTTGCT
AAGGTtTAAGCTATATGACTGGCACTGTGCTCAACTCAGAGTCATTGAATGAACAGTATT
TATTTA (SEQ ID NO: 112)

| OLIGO | start | len | tm | gc % | any | 3' | seq (SEQ ID NOs: 113, 114) |
|---|---|---|---|---|---|---|---|
| LEFT PRIMER | 3 | 22 | 55.40 | 40.91 | 5.00 | 3.00 | CAGGGCATATAATCTAAGCTGT |
| RIGHT PRIMER | 107 | 21 | 55.99 | 47.62 | 7.00 | 2.00 | CAATGACTCTGAGTTGAGCAC |

SEQUENCE SIZE: 126
INCLUDED REGION SIZE: 126

PRODUCT SIZE: 105, PAIR ANY COMPL: 4.00, PAIR 3' COMPL: 2.00
```
  1 TGCAGGGCATATAATCTAAGCTGTAAACGTCCTGTcAGAAGACAACATATTCATCTTGCT
       >>>>>>>>>>>>>>>>>>>>>>

61 AAGGTtTAAGCTATATGACTGGCACTGTGCTCAACTCAGAGTCATTGAATGAACAGTATT
                         <<<<<<<<<<<<<<<<<<<<<

121 TATTTA
```

38) Whole sequence ::: rs8132769-rs2831440

TTCACATTATTCCCTTAAAATAAACTCTCTCCCTCCCCTCTCCCGTCTCAaCCTTGTCCC
TTTCTTTATATAATGGGTAATtCGTTAATGTCAGCAGAATAGTTTTGGGGCCATAATGGC
AAGTATCACGTG (SEQ ID NO: 115)

| OLIGO | start | len | tm | gc % | any | 3' | seq (SEQ ID NOs: 116, 117) |
|---|---|---|---|---|---|---|---|
| LEFT PRIMER | 23 | 19 | 56.84 | 57.89 | 1.00 | 0.00 | AACTCTCTCCCTCCCCTCT |
| RIGHT PRIMER | 115 | 20 | 56.24 | 40.00 | 4.00 | 2.00 | TATGGCCCCAAAACTATTCT |

SEQUENCE SIZE: 132

TABLE 2-continued

INCLUDED REGION SIZE: 132

PRODUCT SIZE: 93, PAIR ANY COMPL: 2.00, PAIR 3' COMPL: 0.00
```
  1 TTCACATTATTCCCTTAAAATAAACTCTCTCCCTCCCCTCTCCCGTCTCAaCCTTGTCCC
                                >>>>>>>>>>>>>>>>>>>>>

61 TTTCTTTATATAATGGGTAATtCGTTAATGTCAGCAGAATAGTTTTGGGGCCATAATGGC
                                     <<<<<<<<<<<<<<<<<<<<

121 AAGTATCACGTG
```

39) Whole sequence ::: rs8134080-rs2831524

TCAGGAAGCAACAAGTACTGGGCAGATTGATACTGTAGCTaGGCTCTAGCTCTATACCTC
TAGAATaaatgttacaaactagcaacttgaaagctaaacctggcccacag
(SEQ ID NO: 118)

OLIGO           start  len  tm    gc %   any  3'    seq (SEQ ID NOs: 119, 120)

LEFT PRIMER      11    20   55.75 45.00  6.00 2.00  ACAAGTACTGGGCAGATTGA
RIGHT PRIMER    104    20   56.27 45.00  4.00 2.00  gccaggtttagctttcaagt
SEQUENCE SIZE: 110
INCLUDED REGION SIZE: 110

PRODUCT SIZE: 94, PAIR ANY COMPL: 4.00, PAIR 3' COMPL: 3.00
```
  1 TCAGGAAGCAACAAGTACTGGGCAGATTGATACTGTAGCTaGGCTCTAGCTCTATACCTC
               >>>>>>>>>>>>>>>>>>>>

61 TAGAATaaatgttacaaactagcaacttgaaagctaaacctggcccacag
                                   <<<<<<<<<<<<<<<<<<<<
```

40) Whole sequence ::: rs4817219-rs4817220 tggttcttgagaattttatatcaggagaaacactgtcagtCtgtattgaaaggaacagag
aaaatTcgaaattaaagaagactattaaacctccaaaattctggca (SEQ ID NO: 121)

OLIGO           start  len  tm    gc %   any  3'    seq (SEQ ID NOs: 122, 123)

LEFT PRIMER      14    22   51.54 31.82  4.00 3.00  ttttatatcaggagaaacactg
RIGHT PRIMER    104    21   55.03 33.33  8.00 2.00  ccagaattttggaggtttaat
SEQUENCE SIZE: 106
INCLUDED REGION SIZE: 106

PRODUCT SIZE: 91, PAIR ANY COMPL: 4.00, PAIR 3' COMPL: 2.00
```
  1 tggttcttgagaattttatatcaggagaaacactgtcagtCtgtattgaaaggaacagag
                  >>>>>>>>>>>>>>>>>>>>>>

61 aaaatTcgaaattaaagaagactattaaacctccaaaattctggca
                             <<<<<<<<<<<<<<<<<<<<<
```

41) Whole sequence ::: rs2250911-rs2250997

GCATCAAACTACACACTGTCATTCCTCCTTTATCTCCAAAAGCTTGAAAATTCCTCACTT
GTaTCTCATTCTTTCTCTCTTAGAAAACTGATCACCTCTGATGAATTAgAACGGAATGAC
CAAGCTTTGGGAGAGGCAAAAGAATCTCGGTGTTAAAGACTCAGAGTTTAA
(SEQ ID NO: 124)

OLIGO           start  len  tm    gc %   any  3'    seq (SEQ ID NOs: 125, 126)

LEFT PRIMER      17    22   58.65 40.91  3.00 0.00  TGTCATTCCTCCTTTATCTCCA
RIGHT PRIMER    144    20   59.42 45.00  4.00 2.00  TTCTTTTGCCTCTCCCAAAG
SEQUENCE SIZE: 171
INCLUDED REGION SIZE: 171

PRODUCT SIZE: 128, PAIR ANY COMPL: 4.00, PAIR 3' COMPL: 0.00
```
  1 GCATCAAACTACACACTGTCATTCCTCCTTTATCTCCAAAAGCTTGAAAATTCCTCACTT
                  >>>>>>>>>>>>>>>>>>>>>>

61 GTaTCTCATTCTTTCTCTCTTAGAAAACTGATCACCTCTGATGAATTAgAACGGAATGAC

121 CAAGCTTTGGGAGAGGCAAAAGAATCTCGGTGTTAAAGACTCAGAGTTTAA
            <<<<<<<<<<<<<<<<<<<<
```

42) Whole sequence ::: rs2831899-rs2831900

TTGAAAATTAAGAAACCCTGGCACAGTGTTGACTGGAGCCaCTTACCTTAATAGAAAATA
AAGCTCACATATATCCATAATGAAAAGCAGAGACCAGCACAACCATAGTCACCTGACAGT
TTtAAAATCCAAGGCCAGGATCTTCTCAACTCAGGCCCACTCA (SEQ ID NO: 127)

TABLE 2-continued

```
OLIGO           start len    tm   gc %   any    3' seq (SEQ ID NOs: 128, 129)
LEFT PRIMER       15   20 60.63 55.00   6.00 2.00 ACCCTGGCACAGTGTTGACT
RIGHT PRIMER     159   20 59.80 50.00   4.00 2.00 TGGGCCTGAGTTGAGAAGAT
SEQUENCE SIZE: 163
INCLUDED REGION SIZE: 163

PRODUCT SIZE: 145, PAIR ANY COMPL: 5.00, PAIR 3' COMPL: 1.00
    1 TTGAAAATTAAGAAACCCTGGCACAGTGTTGACTGGAGCCaCTTACCTTAATAGAAAATA
                     >>>>>>>>>>>>>>>>>>>>

61 AAGCTCACATATATCCATAATGAAAAGCAGAGACCAGCACAACCATAGTCACCTGACAGT

121 TTtAAAATCCAAGGCCAGGATCTTCTCAACTCAGGCCCACTCA
                     <<<<<<<<<<<<<<<<<<<<
```

43) Whole sequence ::: rs2831902-rs2831903

CACATAACTAATAAATTTGTAAGTATGTGCAACGGCTCACaCTTGCTTCCAGAATGGCAC
CTAAAAAACAGATTTACCTCTCCCCAAATTCAGATATGGAATTAAATGTAATGTCAGGAA
AAcTGTCTAAGAGTTGGAAATGGGAAAAAAATGTTCTTTTGGT (SEQ ID NO: 212)

```
OLIGO           start len    tm   gc %   any    3' seq (SEQ ID NOs: 213, 130)
LEFT PRIMER       14   21 53.16 33.33   4.00 2.00 AATTTGTAAGTATGTGCAACG
RIGHT PRIMER     149   20 56.27 35.00   2.00 0.00 TTTTTCCCATTTCCAACTCT
SEQUENCE SIZE: 163
INCLUDED REGION SIZE: 163

PRODUCT SIZE: 136, PAIR ANY COMPL: 4.00, PAIR 3' COMPL: 2.00
    1 CACATAACTAATAAATTTGTAAGTATGTGCAACGGCTCACaCTTGCTTCCAGAATGGCAC
                    >>>>>>>>>>>>>>>>>>>>>

61 CTAAAAAACAGATTTACCTCTCCCCAAATTCAGATATGGAATTAAATGTAATGTCAGGAA

121 AAcTGTCTAAGAGTTGGAAATGGGAAAAAAATGTTCTTTTGGT
                    <<<<<<<<<<<<<<<<<<<<
```

44) Whole sequence ::: rs11088086-rs2251447

AAAAAAAAAGATGAGACAGGCAGGTGCGAAAGAAATAAAAGTCAaAACTGATCCAGTTGG
GAAACTCAGAATTGACAGTTAcGTGTCCTTTCATTTATTGATATTTTGAGATTCACAGGG
GT (SEQ ID NO: 131)

```
OLIGO           start len    tm   gc %   any    3' seq (SEQ ID NOs: 132, 133)
LEFT PRIMER        6   20 56.41 45.00   2.00 2.00 AAAAGATGAGACAGGCAGGT
RIGHT PRIMER     122   20 55.99 40.00   5.00 2.00 ACCCCTGTGAATCTCAAAAT
SEQUENCE SIZE: 122
INCLUDED REGION SIZE: 122

PRODUCT SIZE: 117, PAIR ANY COMPL: 5.00, PAIR 3' COMPL: 2.00
    1 AAAAAAAAAGATGAGACAGGCAGGTGCGAAAGAAATAAAAGTCAaAACTGATCCAGTTGG
               >>>>>>>>>>>>>>>>>>>>

61 GAAACTCAGAATTGACAGTTAcGTGTCCTTTCATTTATTGATATTTTGAGATTCACAGGG
                                             <<<<<<<<<<<<<<<<<<<<

121 GT
      <<
```

45) Whole sequence ::: rs2832040-rs11088088

GAGTTAAATAAAGCACTTGCTTCTATTGTTTGTACCTAAACTTAACAGAAcACAGTAAGT
AACAAGTCATTGGGATGCAGAAAAGAAAAAAGAGAGTGAAGGAAGGAGAaAAGGTGAAGG
GAGAATGGAAGAGAGGAAGGGAGGGAGGAA (SEQ ID NO: 134)

```
OLIGO           start len    tm   gc %   any    3' seq (SEQ ID NOs: 135, 136)
LEFT PRIMER       13   21 54.81 38.10   4.00 0.00 GCACTTGCTTCTATTGTTTGT
RIGHT PRIMER     141   20 57.37 50.00   2.00 0.00 CCCTTCCTCTCTTCCATTCT
SEQUENCE SIZE: 150
INCLUDED REGION SIZE: 150

PRODUCT SIZE: 129, PAIR ANY COMPL: 2.00, PAIR 3' COMPL: 0.00
    1 GAGTTAAATAAAGCACTTGCTTCTATTGTTTGTACCTAAACTTAACAGAAcACAGTAAGT
                    >>>>>>>>>>>>>>>>>>>>>
```

TABLE 2-continued

```
 61 AACAAGTCATTGGGATGCAGAAAAGAAAAAAGAGAGTGAAGGAAGGAGAaAAGGTGAAGG

121 GAGAATGGAAGAGAGGAAGGGAGGGAGGAA
    <<<<<<<<<<<<<<<<<<
```

46) Whole sequence ::: rs2832141-rs2246777

```
aaacgagccaccagtgggAGCACTGCAGGTATCTGTGTGAGACCcGTACTTCACAACTCC
TGCTTTCCCTCCATAAAGtAGCTTGCATTTTCCACATTGACTTTGCAGTTCTTTGGTATC
TGTATTGGT (SEQ ID NO: 137)

OLIGO          start len   tm    gc %   any   3'   seq (SEQ ID NOs: 138, 139)

LEFT PRIMER     14  18  58.28  61.11  6.00  2.00 gtgggAGCACTGCAGGTA
RIGHT PRIMER   123  21  55.05  38.10  4.00  2.00 ACAGATACCAAAGAACTGCAA
SEQUENCE SIZE: 129
INCLUDED REGION SIZE: 129

PRODUCT SIZE: 110, PAIR ANY COMPL: 5.00, PAIR 3' COMPL: 3.00
   1 aaacgagccaccagtgggAGCACTGCAGGTATCTGTGTGAGACCcGTACTTCACAACTCC
                      >>>>>>>>>>>>>>>>>>

61 TGCTTTCCCTCCATAAAGtAGCTTGCATTTTCCACATTGACTTTGCAGTTCTTTGGTATC
                                                 <<<<<<<<<<<<<<<<<<<<<

121 TGTATTGGT
     <<<
```

47) Whole sequence ::: rs2832959-rs9980934

```
TGGACACCTTTCAACTTAGAAATCATAAACAGATTCATTTcCTTAAAGTTAATGaaaaga
attaacagaccctcctcaaaaaagacatatatgcagcctacaatcatatgaaaaaaagtt
caacattactgttcagcaaatcaaa (SEQ ID NO: 140)

OLIGO          start len   tm    gc %   any   3'   seq (SEQ ID NOs: 141, 142)

LEFT PRIMER      1  20  53.30  40.00  3.00  3.00 TGGACACCTTTCAACTTAGA
RIGHT PRIMER   134  22  50.67  27.27  8.00  3.00 gaacagtaatgttgaactttt
SEQUENCE SIZE: 145
INCLUDED REGION SIZE: 145

PRODUCT SIZE: 134, PAIR ANY COMPL: 7.00, PAIR 3' COMPL: 3.00
   1 TGGACACCTTTCAACTTAGAAATCATAAACAGATTCATTTcCTTAAAGTTAATGaaaaga
     >>>>>>>>>>>>>>>>>>>>

61 attaacagaccctcctcaaaaaagacatatatgcagcctacaatcatatgaaaaaaagtt
                                                         <<<<<<<

121 caacattactgttcagcaaatcaaa
     <<<<<<<<<<<<<<<
```

7th group

48) Whole sequence ::: rs2833734-rs2833735

```
TGGATACATTCCTAGAAATAGATGGAAACTGCTCTTGCAAAAAGCTTAGCACATGTTAAA
aATTTTAGAAACAATTTGCCAAAGTTTATTTAGTCTAGTGATTTtGACAGGTTAAATGGA
CCCTTTGAGATCTTTTTTCCTCAAGTACAAAGGCT (SEQ ID NO: 143)

OLIGO          start len   tm    gc %   any   3'   seq (SEQ ID NOs: 144, 145)

LEFT PRIMER    33  21  58.90  38.10  6.00  2.00 TCTTGCAAAAAGCTTAGCACA
RIGHT PRIMER  137  21  57.77  38.10  6.00  1.00 AAAAAGATCTCAAAGGGTCCA
SEQUENCE SIZE: 155
INCLUDED REGION SIZE: 155

PRODUCT SIZE: 105, PAIR ANY COMPL: 4.00, PAIR 3' COMPL: 0.00
   1 TGGATACATTCCTAGAAATAGATGGAAACTGCTCTTGCAAAAAGCTTAGCACATGTTAAA
                                         >>>>>>>>>>>>>>>>>>>>>

61 aATTTTAGAAACAATTTGCCAAAGTTTATTTAGTCTAGTGATTTtGACAGGTTAAATGGA
                                                         <<<<

121 CCCTTTGAGATCTTTTTTCCTCAAGTACAAAGGCT
     <<<<<<<<<<<<<<<<<
```

TABLE 2-continued

49) Whole sequence ::: rs933121-rs933122

GCTTTTGCTGAACATCAAGTGGTGAGCCAGGACTCAAaGCCAGATCTTCTTGTTTCCCTG
TTAGGTGTtTGTAGCACAACTGGTATCTGCAGACTATGCTGCTGGAAGGGCTAGCCGTC
(SEQ ID NO: 146)

OLIGO         start len  tm    gc %  any   3'   seq (SEQ ID NOs: 147, 148)

LEFT PRIMER       1  20  55.61 40.00 6.00 3.00 GCTTTTGCTGAACATCAAGT
RIGHT PRIMER    109  19  55.56 52.63 3.00 3.00 CCTTCCAGCAGCATAGTCT
SEQUENCE SIZE: 119
INCLUDED REGION SIZE: 119

PRODUCT SIZE: 109, PAIR ANY COMPL: 5.00, PAIR 3' COMPL: 1.00
   1 GCTTTTGCTGAACATCAAGTGGTGAGCCAGGACTCAAaGCCAGATCTTCTTGTTTCCCTG
     >>>>>>>>>>>>>>>>>>>>

61 TTAGGTGTtTGTAGCACAACTGGTATCTGCAGACTATGCTGCTGGAAGGGCTAGCCGTC
                                              <<<<<<<<<<<<<<<<<<<

50) Whole sequence ::: rs2834140-rs12626953

ACTGTCCTAGAAAATCCAGGATGTGCAGTGATCAtGTATGAATGCATGGACCTGCACACA
CAGGAGTGAACAAAAGACCCACCCCTGCCAGGTCACCACTCATATCTCACCCCAGCCCAC
GCTAGCTCACaCTCCTCCCCACACACCACTGACCTCATCAT (SEQ ID NO: 149)

OLIGO         start len  tm    gc %  any   3'   seq (SEQ ID NOs: 150, 151)

LEFT PRIMER      12  18  53.64 44.44 7.00 1.00 AAATCCAGGATGTGCAGT
RIGHT PRIMER    161  19  53.29 47.37 4.00 0.00 ATGATGAGGTCAGTGGTGT
SEQUENCE SIZE: 161
INCLUDED REGION SIZE: 161

PRODUCT SIZE: 150, PAIR ANY COMPL: 3.00, PAIR 3' COMPL: 0.00
   1 ACTGTCCTAGAAAATCCAGGATGTGCAGTGATCAtGTATGAATGCATGGACCTGCACACA
                >>>>>>>>>>>>>>>>>>

61 CAGGAGTGAACAAAAGACCCACCCCTGCCAGGTCACCACTCATATCTCACCCCAGCCCAC

121 GCTAGCTCACaCTCCTCCCCACACACCACTGACCTCATCAT
                             <<<<<<<<<<<<<<<<<<<

51) Whole sequence ::: rs2834485-rs3453

CACATCACAGATCATAGTAAATGGCTTTAATTTTTTAaCGAAATCTCACTACTGCAAATG
CATTGTTGTCCTAGCTAATGAATGCAtAGAGTATTGCCTGCAAAATAATAATTGAGATTC
TATT (SEQ ID NO: 152)

OLIGO         start len  tm    gc %  any   3'   seq (SEQ ID NOs: 153, 154)

LEFT PRIMER       3  22  52.35 36.36 4.00 0.00 CATCACAGATCATAGTAAATGG
RIGHT PRIMER    113  21  53.50 23.81 6.00 4.00 AATTATTATTTTGCAGGCAAT
SEQUENCE SIZE: 124
INCLUDED REGION SIZE: 124

PRODUCT SIZE: 111, PAIR ANY COMPL: 5.00, PAIR 3' COMPL: 2.00
   1 CACATCACAGATCATAGTAAATGGCTTTAATTTTTTAaCGAAATCTCACTACTGCAAATG
       >>>>>>>>>>>>>>>>>>>>>>

61 CATTGTTGTCCTAGCTAATGAATGCAtAGAGTATTGCCTGCAAAATAATAATTGAGATTC
                                               <<<<<<<<<<<<<<<<<<<<<

121 TATT

8th group

52) Whole sequence ::: rs9974986-rs2834703

TTATCCTCCACATCCTCATGAGGCAAACACCTTTCCTACCTTACCGCTCCcCAGTGGCCT
CCCTGTTGCCTTCTTATTCAAGACTAAGACtCTCTAGAATGTTCTTTATCCTGAGTCCAG
CTGATTGTCTATACTAATATCAGTACGGGGT (SEQ ID NO: 155)

OLIGO         start len  tm    gc %  any   3'   seq (SEQ ID NOs: 156, 157)

LEFT PRIMER      17  20  60.50 50.00 4.00 2.00 CATGAGGCAAACACCTTTCC
RIGHT PRIMER    121  22  58.46 45.45 3.00 0.00 GCTGGACTCAGGATAAAGAACA

TABLE 2-continued

```
SEQUENCE SIZE: 151
INCLUDED REGION SIZE: 151

PRODUCT SIZE: 105, PAIR ANY COMPL: 4.00, PAIR 3' COMPL: 1.00
   1 TTATCCTCCACATCCTCATGAGGCAAACACCTTTCCTACCTTACCGCTCCcCAGTGGCCT
                       >>>>>>>>>>>>>>>>>>>>

61 CCCTGTTGCCTTCTTATTCAAGACTAAGACtCTCTAGAATGTTCTTTATCCTGAGTCCAG
                                      <<<<<<<<<<<<<<<<<<<<

121 CTGATTGTCTATACTAATATCAGTACGGGGT
     <
```

53) Whole sequence ::: rs12482353-rs2205032

ATCACCTGGTTTGGTGCATCCTCGCAGAAAGAGAGCCATACAGTGAAGTGGAAACACACCCAAA
AGCTCTGCAATATTCCTAGAAGTTCTCGAATCTCCTCCTTAAcAGAGCTGCAGAAGGGAAACAC
AGACAGGAAGCACCTGTTTGACTCAgACAGCAGCCCTAATGCAGTGCCACTCAGGAGCATTCCC
TCATTTGAAGACCCCCCAATTACATGAAATTATCAACCCC (SEQ ID NO: 346)

| OLIGO | start | len | tm | gc % | any | 3' | seq (SEQ ID NOs: 347, 348) |
|---|---|---|---|---|---|---|---|
| LEFT PRIMER | 56 | 20 | 59.74 | 45.00 | 4.00 | 2.00 | ACACCCAAAAGCTCTGCAAT |
| RIGHT PRIMER | 199 | 20 | 60.59 | 50.00 | 4.00 | 2.00 | CAAATGAGGGAATGCTCCTG |

SEQUENCE SIZE: 232
INCLUDED REGION SIZE: 232

```
PRODUCT SIZE: 144, PAIR ANY COMPL: 3.00, PAIR 3' COMPL: 0.00
   1 ATCACCTGGTTTGGTGCATCCTCGCAGAAAGAGAGCCATACAGTGAAGTGGAAACACACC
                                                            >>>>>

61 CAAAAGCTCTGCAATATTCCTAGAAGTTCTCGAATCTCCTCCTTAAcAGAGCTGCAGAAG
     >>>>>>>>>>>>>>>

121 GGAAACACAGACAGGAAGCACCTGTTTGACTCAgACAGCAGCCCTAATGCAGTGCCACTC
                                                              <

181 AGGAGCATTCCCTCATTTGAAGACCCCCCAATTACATGAAATTATCAACCCC
         <<<<<<<<<<<<<<<<<<<<
```

54) Whole sequence ::: rs2776266-rs2835001 agggtgcagcactttattatggaagcctgagctgactaatacaGGTGTCTcTATATCTCA
CTGAGGGAAAGTGACAGGAAAGTAAGAACCATTTaTGTCCAAGAGTCCAGAGGAGTCAAC
CAGATTCTGGGGGAAAAGAAGGTAC (SEQ ID NO: 158)

| OLIGO | start | len | tm | gc % | any | 3' | seq (SEQ ID NOs: 159, 160) |
|---|---|---|---|---|---|---|---|
| LEFT PRIMER | 20 | 20 | 58.75 | 50.00 | 4.00 | 1.00 | tggaagcctgagctgactaa |
| RIGHT PRIMER | 142 | 20 | 59.87 | 50.00 | 4.00 | 3.00 | CCTTCTTTTCCCCCAGAATC |

SEQUENCE SIZE: 145
INCLUDED REGION SIZE: 145

```
PRODUCT SIZE: 123, PAIR ANY COMPL: 4.00, PAIR 3' COMPL: 0.00
   1 agggtgcagcactttattatggaagcctgagctgactaatacaGGTGTCTcTATATCTCA
                       >>>>>>>>>>>>>>>>>>>>

61 CTGAGGGAAAGTGACAGGAAAGTAAGAACCATTTaTGTCCAAGAGTCCAGAGGAGTCAAC

121 CAGATTCTGGGGGAAAAGAAGGTAC
         <<<<<<<<<<<<<<<<<<<<
```

55) Whole sequence ::: rs1984014-rs1984015

TGAGAAT TTAGGAGAACAGAAGATCAGAGGGCTGCAcAGGCTAAACTAGACAATGAGCCC
ATGCAAGTAAGTTAAGAGGAGAAGCGGGTAAGTATGCACCTGCTTTGTCTAGGtGACCAG
CAAGCATTTAGCAATAGTCTTT TCAAAACAACAG (SEQ ID NO: 161)

| OLIGO | start | len | tm | gc % | any | 3' | seq (SEQ ID NOs: 162, 163) |
|---|---|---|---|---|---|---|---|
| LEFT PRIMER | 8 | 22 | 53.09 | 40.91 | 4.00 | 1.00 | TTAGGAGAACAGAAGATCAGAG |
| RIGHT PRIMER | 142 | 22 | 53.52 | 31.82 | 4.00 | 2.00 | AAAGACTATTGCTAAATGCTTG |

SEQUENCE SIZE: 154
INCLUDED REGION SIZE: 154

```
PRODUCT SIZE: 135, PAIR ANY COMPL: 4.00, PAIR 3' COMPL: 2.00
   1 TGAGAATTTAGGAGAACAGAAGATCAGAGGGCTGCAcAGGCTAAACTAGACAATGAGCCC
             >>>>>>>>>>>>>>>>>>>>>>
```

TABLE 2-continued

```
 61 ATGCAAGTAAGTTAAGAGGAGAAGCGGGTAAGTATGCACCTGCTTTGTCTAGGtGACCAG

121 CAAGCATTTAGCAATAGTCTTTTCAAAACAACAG
    <<<<<<<<<<<<<<<<<<<
```

56) Whole sequence ::: rs1014593-rs9305569

```
GGAACTGCAGGAGATCCCTGCTGCCTTCCAGTTCATGGGATGATGGCCTCCACTTCTGCCCCTG
TTTGCTTCTCCTTTCAaATCTTACATGAAGGTATACAGTTTGAAGAAGCCAGTTTGACTCCAAT
ATCTGTGCAATGGAATACTGCTCATTAAAAAGgAATTAAACTATTGATACACACAACATGGGTG
AAGATCAAACTGTCTCCTTCCCTTTGATTCAAGGGAATCTGAGAAATG (SEQ ID NO: 349)
```

| OLIGO | start | len | tm | gc % | any | 3' | seq (SEQ ID NOs: 350, 351) |
|---|---|---|---|---|---|---|---|
| LEFT PRIMER | 51 | 19 | 59.86 | 52.63 | 2.00 | 0.00 | ACTTCTGCCCCTGTTTGCT |
| RIGHT PRIMER | 198 | 21 | 58.84 | 42.86 | 4.00 | 3.00 | TGATCTTCACCCATGTTGTGT |

SEQUENCE SIZE: 239
INCLUDED REGION SIZE: 239

PRODUCT SIZE: 148, PAIR ANY COMPL: 2.00, PAIR 3' COMPL: 0.00

```
  1 GAACTGCAGGAGATCCCTGCTGCCTTCCAGTTCATGGGATGATGGCCTCCACTTCTGCCC
                                                     >>>>>>>>>>

61 CTGTTTGCTTCTCCTTTCAaATCTTACATGAAGGTATACAGTTTGAAGAAGCCAGTTTGA
    >>>>>>>>>

121 CTCCAATATCTGTGCAATGGAATACTGCTCATTAAAAAGgAATTAAACTATTGATACACA
                                                            <<<

181 CAACATGGGTGAAGATCAAACTGTCTCCTTCCCTTTGATTCAAGGGAATCTGAGAAATG
    <<<<<<<<<<<<<<<<<<
```

57) Whole sequence ::: rs7281674-rs2835316

```
AAACAGGCAAAATAAGCGTAGGGCTGTGTGTGCAACAGTTaATCATAAAGCCATCACCAG
GAGACgTCACTGGGCGCCTTCTGGAGTCTATCCGTCCTAACTTTGC (SEQ ID NO: 164)
```

| OLIGO | start | len | tm | gc % | any | 3' | seq (SEQ ID NOs: 165, 166) |
|---|---|---|---|---|---|---|---|
| LEFT PRIMER | 13 | 20 | 59.93 | 55.00 | 4.00 | 0.00 | TAAGCGTAGGGCTGTGTGTG |
| RIGHT PRIMER | 97 | 21 | 60.08 | 57.14 | 3.00 | 1.00 | GGACGGATAGACTCCAGAAGG |

SEQUENCE SIZE: 106
INCLUDED REGION SIZE: 106

PRODUCT SIZE: 85, PAIR ANY COMPL: 3.00, PAIR 3' COMPL: 0.00

```
  1 AAACAGGCAAAATAAGCGTAGGGCTGTGTGTGCAACAGTTaATCATAAAGCCATCACCAG
                >>>>>>>>>>>>>>>>>>>>

61 GAGACgTCACTGGGCGCCTTCTGGAGTCTATCCGTCCTAACTTTGC
                      <<<<<<<<<<<<<<<<<<<<<
```

58) Whole sequence ::: rs13047304-rs13047322

```
gaatgaccttggcactttttatcaaacatcaactggccacaCacaggtgagtctacttctg
gacacttaTcctgttccattcatctgtatatctctatccttacac (SEQ ID NO: 167)
```

| OLIGO | start | len | tm | gc % | any | 3' | seq (SEQ ID NOs: 168, 169) |
|---|---|---|---|---|---|---|---|
| LEFT PRIMER | 1 | 23 | 60.36 | 39.13 | 3.00 | 2.00 | gaatgaccttggcactttttatca |
| RIGHT PRIMER | 101 | 27 | 57.86 | 33.33 | 4.00 | 0.00 | aaggatagagatatacagatgaatgga |

SEQUENCE SIZE: 105
INCLUDED REGION SIZE: 105

PRODUCT SIZE: 101, PAIR ANY COMPL: 4.00, PAIR 3' COMPL: 1.00

```
  1 gaatgaccttggcactttttatcaaacatcaactggccacaCacaggtgagtctacttctg
    >>>>>>>>>>>>>>>>>>>>>>>

61 gacacttaTcctgttccattcatctgtatatctctatccttacac
                      <<<<<<<<<<<<<<<<<<<<<<<<<<<
```

TABLE 2-continued

59) Whole sequence ::: rs2835545-rs4816551

CTGCTGGAATAGGCTGCTTGGCCATGTTCTTGGAAGCTACCACCATATCAaGGTAATTTC
CCACACAACATTCCAGCCCCTGCTTTCCtCTCTGGCCTTATCTAGGGCCATTCCCCAACT
CAGGTGAAT (SEQ ID NO: 170)

| OLIGO | start | len | tm | gc % | any | 3' | seq (SEQ ID NOs: 171, 172) |
|---|---|---|---|---|---|---|---|
| LEFT PRIMER | 20 | 20 | 60.21 | 50.00 | 4.00 | 2.00 | GGCCATGTTCTTGGAAGCTA |
| RIGHT PRIMER | 128 | 20 | 60.89 | 50.00 | 5.00 | 0.00 | TTCACCTGAGTTGGGGAATG |

SEQUENCE SIZE: 129
INCLUDED REGION SIZE: 129

PRODUCT SIZE: 109, PAIR ANY COMPL: 3.00, PAIR 3' COMPL: 0.00
```
  1 CTGCTGGAATAGGCTGCTTGGCCATGTTCTTGGAAGCTACCACCATATCAaGGTAATTTC
                        >>>>>>>>>>>>>>>>>>>>

61 CCACACAACATTCCAGCCCCTGCTTTCCtCTCTGGCCTTATCTAGGGCCATTCCCCAACT
                                              <<<<<<<<<<

121 CAGGTGAAT
    <<<<<<<<
```

60) Whole sequence ::: rs2835735-rs2835736

ACCTTTGTTCCATGCACCGCGCAAATACCTGGGAACCCTTaTTGCCCAACTCAAGAGCCA
GAGTCCTCTGTCATCATTTTGCCTCTCTCCTAAGTGAgAGGACTGAGTGCAGACTTGGTG
TTTGTGGGTGAGGCATGT (SEQ ID NO: 173)

| OLIGO | start | len | tm | gc % | any | 3' | seq (SEQ ID NOs: 174, 175) |
|---|---|---|---|---|---|---|---|
| LEFT PRIMER | 11 | 18 | 62.22 | 55.56 | 5.00 | 0.00 | CATGCACCGCGCAAATAC |
| RIGHT PRIMER | 136 | 19 | 59.38 | 52.63 | 2.00 | 0.00 | ATGCCTCACCCACAAACAC |

SEQUENCE SIZE: 138
INCLUDED REGION SIZE: 138

PRODUCT SIZE: 126, PAIR ANY COMPL: 3.00, PAIR 3' COMPL: 0.00
```
  1 ACCTTTGTTCCATGCACCGCGCAAATACCTGGGAACCCTTaTTGCCCAACTCAAGAGCCA
              >>>>>>>>>>>>>>>>>>

61 GAGTCCTCTGTCATCATTTTGCCTCTCTCCTAAGTGAgAGGACTGAGTGCAGACTTGGTG
                                                            <<<

121 TTTGTGGGTGAGGCATGT
    <<<<<<<<<<<<<<<<
```

61) Whole sequence ::: rs13047608-rs2835826

CTCCTGAGTCCAAGCCCTTCTCACTCACCTCTTTCTTGAACTAATTTCTTcCTGTTTTTT
TCCAGTCCTCCCTTCTGTTCATGTCTCTCCTCTGCACACTTCCATTTTgTGGTTCAGAAA
ATGTCACCGTCCCAG TCACACTTGCCTTATGGCTGTTGT (SEQ ID NO: 176)

| OLIGO | start | len | tm | gc % | any | 3' | seq (SEQ ID NOs: 177, 178) |
|---|---|---|---|---|---|---|---|
| LEFT PRIMER | 9 | 20 | 60.39 | 55.00 | 4.00 | 0.00 | TCCAAGCCCTTCTCACTCAC |
| RIGHT PRIMER | 135 | 20 | 59.97 | 50.00 | 3.00 | 1.00 | CTGGGACGGTGACATTTTCT |

SEQUENCE SIZE: 159
INCLUDED REGION SIZE: 159

PRODUCT SIZE: 127, PAIR ANY COMPL: 4.00, PAIR 3' COMPL: 0.00
```
  1 CTCCTGAGTCCAAGCCCTTCTCACTCACCTCTTTCTTGAACTAATTTCTTcCTGTTTTTT
            >>>>>>>>>>>>>>>>>>>>

61 TCCAGTCCTCCCTTCTGTTCATGTCTCTCCTCTGCACACTTCCATTTTgTGGTTCAGAAA
                                                    <<<<<

121 ATGTCACCGTCCCAGTCACACTTGCCTTATGGCTGTTGT
    <<<<<<<<<<<<<<<
```

TABLE 2-continued

62) Whole sequence ::: rs857998-rs17284497

TGGAGAAAGTTGTTGCAAACTGCCCAGAGACCCTGGGAGTCACTCCAGTTTTCTGAAACCCAGA
TATTTCAGtGCCTCAGGAGAGACAAGTCCTGACCTTCTCTCCTCCAGCTCTCCCAGgAGATAGG
CAAGCCCCTAACTCCCTAACTAAGCCCTTCAGACCTGAAATCCATTGAGTGGCTTCTTT
(SEQ ID NO: 352)

```
OLIGO          start len   tm    gc %  any   3'   seq (SEQ ID NOs: 353, 354)

LEFT PRIMER       15   18 59.35 61.11 4.00 0.00 GCAAACTGCCCAGAGACC
RIGHT PRIMER     147   20 60.57 55.00 2.00 2.00 TTAGGGAGTTAGGGGCTTGC
SEQUENCE SIZE: 189
INCLUDED REGION SIZE: 189

PRODUCT SIZE: 133, PAIR ANY COMPL: 5.00, PAIR 3' COMPL: 2.00
   1 TGGAGAAAGTTGTTGCAAACTGCCCAGAGACCCTGGGAGTCACTCCAGTTTTCTGAAACC
                    >>>>>>>>>>>>>>>>>>

61 CAGATATTTCAGtGCCTCAGGAGAGACAAGTCCTGACCTTCTCTCCTCCAGCTCTCCCAG 121 gAGATAGGCAAGCCCCTAACTCCCTAACTAAGCCCTTCAGACCTGAAATCCATTGAGTGG
              <<<<<<<<<<<<<<<<<<<<

181 CTTCTTTAC
```

9<sup>th</sup> group

63) Whole sequence ::: rs2836550-rs2212596

CCCAGGAAGAGTGGAAAGATTAACCTTTGTGAGCCAAACCaGTGACACTTGATTACTTGA
CAGAACTAATCCTTCTGTCCTGATGACAGAAcTTCAACTACACAGGTACATGCAAGCTAA
TATCTGTTGTAA (SEQ ID NO: 179)

```
OLIGO          start len   tm    gc %  any   3'   seq (SEQ ID NOs: 180, 181)

LEFT PRIMER        1   21 59.56 47.62 3.00 2.00 CCCAGGAAGAGTGGAAAGATT
RIGHT PRIMER     120   21 56.03 42.86 6.00 1.00 TTAGCTTGCATGTACCTGTGT
SEQUENCE SIZE: 132
INCLUDED REGION SIZE: 132

PRODUCT SIZE: 120, PAIR ANY COMPL: 5.00, PAIR 3' COMPL: 3.00
   1 CCCAGGAAGAGTGGAAAGATTAACCTTTGTGAGCCAAACCaGTGACACTTGATTACTTGA
     >>>>>>>>>>>>>>>>>>>>>

61 CAGAACTAATCCTTCTGTCCTGATGACAGAAcTTCAACTACACAGGTACATGCAAGCTAA
                                             <<<<<<<<<<<<<<<<<<<<<

121 TATCTGTTGTAA
```

64) Whole sequence ::: rs2836660-rs2836661

GCCTGGCAAGCTAGATGGGGTGAATTTTCACCTGCCACAGcCGCAAGTCAAAGCCACCGG
CTTCTCTCTTCTCCCTCCCATTGCTCCTGACAGCCAGGGTTAATATTTTGCCTCATGTAA
ACAGGGAGGCAtCCACCCGAGAATCTCCCCTCAGCCCACATAAGC (SEQ ID NO: 182)

```
OLIGO          start len   tm    gc %  any   3'   seq (SEQ ID NOs: 183, 184)

LEFT PRIMER        9   20 55.41 40.00 4.00 2.00 AGCTAGATGGGGTGAATTTT
RIGHT PRIMER     158   18 61.14 61.11 3.00 3.00 TGGGCTGAGGGGAGATTC
SEQUENCE SIZE: 165
INCLUDED REGION SIZE: 165

PRODUCT SIZE: 150, PAIR ANY COMPL: 4.00, PAIR 3' COMPL: 3.00
   1 GCCTGGCAAGCTAGATGGGGTGAATTTTCACCTGCCACAGcCGCAAGTCAAAGCCACCGG
             >>>>>>>>>>>>>>>>>>>>

61 CTTCTCTCTTCTCCCTCCCATTGCTCCTGACAGCCAGGGTTAATATTTTGCCTCATGTAA

121 ACAGGGAGGCAtCCACCCGAGAATCTCCCCTCAGCCCACATAAGC
                       <<<<<<<<<<<<<<<<<<
```

TABLE 2-continued

65) Whole sequence ::: rs465612-rs8131220 atcaagctaattaatgttatctatcacttcAcatagttcaacctttttttgtggtgagag
tactgaagatctactctcttagcaattttcaaatctaaaatacattattattaacacagt
cactgtgccGtacgttagctctgaggaccttattcatttt (SEQ ID NO: 185)

| OLIGO | start | len | tm | gc % | any | 3' | seq (SEQ ID NOs: 186, 187) |
|---|---|---|---|---|---|---|---|
| LEFT PRIMER | 1 | 22 | 47.51 | 22.73 | 6.00 | 4.00 | atcaagctaattaatgttatct |
| RIGHT PRIMER | 158 | 20 | 50.92 | 40.00 | 5.00 | 5.00 | aatgaataaggtcctcagag |

SEQUENCE SIZE: 160
INCLUDED REGION SIZE: 160

PRODUCT SIZE: 158, PAIR ANY COMPL: 5.00, PAIR 3' COMPL: 2.00
```
  1 atcaagctaattaatgttatctatcacttcAcatagttcaacctttttttgtggtgagag
    >>>>>>>>>>>>>>>>>>>>>>

61 tactgaagatctactctcttagcaattttcaaatctaaaatacattattattaacacagt 121 cactgtgccGtacgttagctctgaggaccttattcatttt
                         <<<<<<<<<<<<<<<<<<<<
```

66) Whole sequence ::: rs9980072-rs8130031

TTTAATCTGATCATTGCCCTATGAGGTAGGgAGTATTCTGATTCCCATTTTATAAATAAG
GAACCCGAGGCTTAGAGAGCATCaGTGACTTGTTCAAGGTCACCCACAGCTGTCAAGTGA
CAGA (SEQ ID NO: 188)

| OLIGO | start | len | tm | gc % | any | 3' | seq (SEQ ID NOs: 189, 190) |
|---|---|---|---|---|---|---|---|
| LEFT PRIMER | 1 | 21 | 55.02 | 33.33 | 6.00 | 2.00 | TTTAATCTGATCATTGCCCTA |
| RIGHT PRIMER | 111 | 18 | 57.61 | 55.56 | 5.00 | 1.00 | AGCTGTGGGTGACCTTGA |

SEQUENCE SIZE: 124
INCLUDED REGION SIZE: 124

PRODUCT SIZE: 111, PAIR ANY COMPL: 3.00, PAIR 3' COMPL: 1.00
```
  1 TTTAATCTGATCATTGCCCTATGAGGTAGGgAGTATTCTGATTCCCATTTTATAAATAAG
    >>>>>>>>>>>>>>>>>>>>>

61 GAACCCGAGGCTTAGAGAGCATCaGTGACTTGTTCAAGGTCACCCACAGCTGTCAAGTGA
                                       <<<<<<<<<<<<<<<<<<

121 CAGA
```

10$^{th}$ group

67) Whole sequence ::: rs418359-rs2836926 tgtcccaccattgtgtattaggtttgtagagCgtagacaacttgccttttagtttgtag
gtttctgtatcaagagaagatgtgtgtGggcctaacctagattacaggatcctggacttc
aagtctga (SEQ ID NO: 191)

| OLIGO | start | len | tm | gc % | any | 3' | seq (SEQ ID NOs: 192, 193) |
|---|---|---|---|---|---|---|---|
| LEFT PRIMER | 1 | 20 | 54.64 | 40.00 | 6.00 | 3.00 | tgtcccaccattgtgtatta |
| RIGHT PRIMER | 128 | 20 | 54.70 | 45.00 | 9.00 | 3.00 | tcagacttgaagtccaggat |

SEQUENCE SIZE: 128
INCLUDED REGION SIZE: 128

PRODUCT SIZE: 128, PAIR ANY COMPL: 3.00, PAIR 3' COMPL: 1.00
```
  1 tgtcccaccattgtgtattaggtttgtagagCgtagacaacttgccttttagtttgtag
    >>>>>>>>>>>>>>>>>>>>

61 gtttctgtatcaagagaagatgtgtgtGggcctaacctagattacaggatcctggacttc
                                                  <<<<<<<<<<<

121 aagtctga
    <<<<<<<<
```

TABLE 2-continued

68) Whole sequence ::: rs11701943-rs4816634 tcatttgctaaggtcggatagctcctaattggcaaagtcaCgatgggatcccagggattc
tgaggatgaagcctgtgtttaataactAttatgccaAGTGAGCATTTTCAAATATATGAG
AGAAATTA (SEQ ID NO: 194)

| OLIGO | start | len | tm | gc % | any | 3' | seq (SEQ ID NOs: 195, 196) |
|---|---|---|---|---|---|---|---|
| LEFT PRIMER | 2 | 19 | 53.86 | 42.11 | 4.00 | 2.00 | catttgctaaggtcggata |
| RIGHT PRIMER | 114 | 20 | 51.56 | 30.00 | 6.00 | 2.00 | TATTTGAAAATGCTCACTtg |

SEQUENCE SIZE: 128
INCLUDED REGION SIZE: 128

PRODUCT SIZE: 113, PAIR ANY COMPL: 6.00, PAIR 3' COMPL: 0.00
```
  1 tcatttgctaaggtcggatagctcctaattggcaaagtcaCgatgggatcccagggattc
    >>>>>>>>>>>>>>>>>>>

61 tgaggatgaagcctgtgtttaataactAttatgccaAGTGAGCATTTTCAAATATATGAG
                                        <<<<<<<<<<<<<<<<<<<<

121 AGAAATTA
```

69) Whole sequence ::: rs7278447-rs7278858

CATTGCTTCAGGGGTGTTAGTTTTGTGTTCaCAACTAGATTATAAACTCCTCTTGCATTC
CTGATGGCAGTGACTTGAAGGCAtttatttgaagaataatagacatacagaaagggcac
atgtcataaaggtacagctggacgacttttcacaaagtg (SEQ ID NO: 197)

| OLIGO | start | len | tm | gc % | any | 3' | seq (SEQ ID NOs: 198, 199) |
|---|---|---|---|---|---|---|---|
| LEFT PRIMER | 5 | 20 | 55.96 | 45.00 | 2.00 | 0.00 | GCTTCAGGGGTGTTAGTTTT |
| RIGHT PRIMER | 157 | 20 | 55.97 | 45.00 | 5.00 | 1.00 | ctttgtgaaaagtcgtccag |

SEQUENCE SIZE: 159
INCLUDED REGION SIZE: 159

PRODUCT SIZE: 153, PAIR ANY COMPL: 4.00, PAIR 3' COMPL: 0.00
```
  1 CATTGCTTCAGGGGTGTTAGTTTTGTGTTCaCAACTAGATTATAAACTCCTCTTGCATTC
       >>>>>>>>>>>>>>>>>>>>

61 CTGATGGCAGTGACTTGAAGGCAtttatttgaagaataatagacatacagaaagggcac 121 atgtcataaaggtacagctggacgacttttcacaaagtg
                        <<<<<<<<<<<<<<<<<<<<
```

70) Whole sequence ::: rs385787-rs367001

GAGAGGATGGTGCCATCATGGAAAGCATGGGGCAGTCATGGAGATGACGGaGTAGCTCAT
GGAGAAgATAATGCCATCATGGAAGGCATAGTGCAGTCATGGAGATGATGGTGCAGC
(SEQ ID NO: 200)

| OLIGO | start | len | tm | gc % | any | 3' | seq (SEQ ID NOs: 201, 202) |
|---|---|---|---|---|---|---|---|
| LEFT PRIMER | 13 | 18 | 58.34 | 50.00 | 7.00 | 3.00 | CCATCATGGAAAGCATGG |
| RIGHT PRIMER | 108 | 20 | 55.09 | 45.00 | 4.00 | 2.00 | TCATCTCCATGACTGCACTA |

SEQUENCE SIZE: 117
INCLUDED REGION SIZE: 117

PRODUCT SIZE: 96, PAIR ANY COMPL: 7.00, PAIR 3' COMPL: 3.00
```
  1 GAGAGGATGGTGCCATCATGGAAAGCATGGGGCAGTCATGGAGATGACGGaGTAGCTCAT
               >>>>>>>>>>>>>>>>>>

61 GGAGAAgATAATGCCATCATGGAAGGCATAGTGCAGTCATGGAGATGATGGTGCAGC
                                   <<<<<<<<<<<<<<<<<<<<
```

71) Whole sequence ::: rs367001-rs386095

ATGGGGCAGTCATGGAGATGACGGAGTAGCTCATGGAGAAaATAATGCCATCATGGAAGG
CATAGTGCAGTCATGGAGATGATGGTGCAGCTCATGGAGAAGATGGTGCCATCATGgAAG
GCATGGTGCAATCATGGAGTAGACAGTGCAGCTGGGCCaagattctc
(SEQ ID NO: 203)

| OLIGO | start | len | tm | gc % | any | 3' | seq (SEQ ID NOs: 204, 205) |
|---|---|---|---|---|---|---|---|
| LEFT PRIMER | 15 | 20 | 54.39 | 50.00 | 4.00 | 3.00 | GAGATGACGGAGTAGCTCAT |
| RIGHT PRIMER | 156 | 18 | 55.17 | 61.11 | 6.00 | 2.00 | CCCAGCTGCACTGTCTAC |

SEQUENCE SIZE: 167
INCLUDED REGION SIZE: 167

TABLE 2-continued

```
PRODUCT SIZE: 142, PAIR ANY COMPL: 6.00, PAIR 3' COMPL: 2.00
   1 ATGGGGCAGTCATGGAGATGACGGAGTAGCTCATGGAGAAaATAATGCCATCATGGAAGG
             >>>>>>>>>>>>>>>>>>>>

61 CATAGTGCAGTCATGGAGATGATGGTGCAGCTCATGGAGAAGATGGTGCCATCATGgAAG

121 GCATGGTGCAATCATGGAGTAGACAGTGCAGCTGGGCCaagattctc
                                      <<<<<<<<<<<<<<<<

72) Whole sequence ::: rs2837296-rs2837297
```

GATGTGCCTCTCTTGTTCCAATCACAGGACAGGGGTATAAcTAGGGGCACTGTCTATACT
GGCTGCACTCTGGCCAGTGCTGTCCCAgGTAGATTCATCAGGGTCTAGAGCTTCAGCTAA
CAGCATGA (SEQ ID NO: 206)

```
OLIGO          start len   tm    gc %  any   3'  seq (SEQ ID NOs: 207, 208)

LEFT PRIMER      11  20  56.00  45.00  4.00 1.00 TCTTGTTCCAATCACAGGAC
RIGHT PRIMER    126  20  54.59  45.00  6.00 3.00 ATGCTGTTAGCTGAAGCTCT
SEQUENCE SIZE: 128
INCLUDED REGION SIZE: 128

PRODUCT SIZE: 116, PAIR ANY COMPL: 4.00, PAIR 3' COMPL: 1.00
   1 GATGTGCCTCTCTTGTTCCAATCACAGGACAGGGGTATAAcTAGGGGCACTGTCTATACT
             >>>>>>>>>>>>>>>>>>>>

61 GGCTGCACTCTGGCCAGTGCTGTCCCAgGTAGATTCATCAGGGTCTAGAGCTTCAGCTAA
                                            <<<<<<<<<<<<<

121 CAGCATGA
     <<<<<<<

73) Whole sequence ::: rs4239808-rs2410205
```

AGGGCCATGGGATGATGCAGGTGGAGACTGGAGTGCTACAGCTGCAAGCAAATACATTTCTGTG
CTGTGAAGCCAcCCATTTGGTGGTACTACGTTAAAACAGCTCTAGGAAATTAAtACAGATGTTG
CCTGTATTTTTGTTTCTCATATTACTACTCATTGTTTTAATGATGACTGTTTTATT
(SEQ ID NO: 355)

```
OLIGO          start len   tm    gc %  any   3'  seq (SEQ ID NOs: 356, 357)

LEFT PRIMER      19  20  57.45  55.00  4.00 2.00 AGGTGGAGACTGGAGTGCTA
RIGHT PRIMER    145  22  56.58  31.82  2.00 0.00 AGAAACAAAAATACAGGCAACA
SEQUENCE SIZE: 184
INCLUDED REGION SIZE: 184

PRODUCT SIZE: 127, PAIR ANY COMPL: 3.00, PAIR 3' COMPL: 1.00
   1 AGGGCCATGGGATGATGCAGGTGGAGACTGGAGTGCTACAGCTGCAAGCAAATACATTTC
                     >>>>>>>>>>>>>>>>>>>>

61 TGTGCTGTGAAGCCAcCCATTTGGTGGTACTACGTTAAAACAGCTCTAGGAAATTAAtAC

121 AGATGTTGCCTGTATTTTTGTTTCTCATATTACTACTCATTGTTTTAATGATGACTGTTT
              <<<<<<<<<<<<<<<<<<<<<<

181 TATT

74) Whole sequence ::: rs2837381-rs4816672
```

TTTTATTCATTAAGTTGAAAGCTCCTAAAGCAGAGGGACCaTATTTTTATGTCCCAACTC
TCCTTAAGgCCTTGCCTATGATAGCACATCTCTTCAATAGAATTGTCCT
(SEQ ID NO: 209)

```
OLIGO          start len   tm    gc %  any   3'  seq (SEQ ID NOs: 210, 211)

LEFT PRIMER      16  20  55.17  45.00  4.00 0.00 TGAAAGCTCCTAAAGCAGAG
RIGHT PRIMER     97  20  50.59  35.00  4.00 3.00 TTGAAGAGATGTGCTATCAT
SEQUENCE SIZE: 109
INCLUDED REGION SIZE: 109

PRODUCT SIZE: 82, PAIR ANY COMPL: 5.00, PAIR 3' COMPL: 1.00
   1 TTTTATTCATTAAGTTGAAAGCTCCTAAAGCAGAGGGACCaTATTTTTATGTCCCAACTC
                  >>>>>>>>>>>>>>>>>>>>
```

TABLE 2-continued

```
 61 TCCTTAAGgCCTTGCCTATGATAGCACATCTCTTCAATAGAATTGTCCT
                   <<<<<<<<<<<<<<<<<<<

11 th group

75) Whole sequence ::: rs13047873-rs2837697
```

AAAGACCAGCTTTTAGCTGAACATCAGGGCTGCCTTCAGAGTTTAATTACCGCCCTCCCC
ATGGGGCCAAATGAGCCATCGACTCCTCCCAAGGGGGTTCgGCTTGGTACTGATCTTTAA
GTAAGTaAACGCTAAACCAGCTCATCTTAAAGCGCCCACATCTGATTTCCTGCTCTGCTG
CAAGACAGTAGGTGACTGGTAATGACC (SEQ ID NO: 214)

```
OLIGO          start len   tm    gc %  any   3' seq (SEQ ID NOs: 215, 216)

LEFT PRIMER     26   20  59.08  50.00  5.00  2.00 AGGGCTGCCTTCAGAGTTTA
RIGHT PRIMER   155   20  59.62  50.00  5.00  2.00 GCGCTTTAAGATGAGCTGGT
SEQUENCE SIZE: 207
INCLUDED REGION SIZE: 207

PRODUCT SIZE: 130, PAIR ANY COMPL: 3.00, PAIR 3' COMPL: 1.00
   1 AAAGACCAGCTTTTAGCTGAACATCAGGGCTGCCTTCAGAGTTTAATTACCGCCCTCCCC
                              >>>>>>>>>>>>>>>>>>>>

61 ATGGGGCCAAATGAGCCATCGACTCCTCCCAAGGGGGTTCgGCTTGGTACTGATCTTTAA

121 GTAAGTaAACGCTAAACCAGCTCATCTTAAAGCGCCCACATCTGATTTCCTGCTCTGCTG
                       <<<<<<<<<<<<<<<<<<<<

181 CAAGACAGTAGGTGACTGGTAATGACC

76) Whole sequence ::: rs455999-rs9305700
```

ACTCTGCTCCCAGTGTGAACATGGGGAAAGTTGATTAAACTCTCTGACTTCAGATTCCTC
aTGTAAAATGTGGGGAAACAGCTCTGACTTAATGGTGTCACTGTGAGGAGTAAATGAGGT
AgCATATTTAAAGGATTTTGTATAGTGCTGGTGACAGTAACCAGCCAATAGATGATATAG
CTAGTAATAGCA (SEQ ID NO: 217)

```
OLIGO          start len   tm    gc %  any   3' seq (SEQ ID NOs: 218, 219)

LEFT PRIMER     16   20  57.84  40.00  4.00  2.00 TGAACATGGGGAAAGTTGAT
RIGHT PRIMER   154   22  56.81  40.91  4.00  0.00 TCACCAGCACTATACAAAATCC
SEQUENCE SIZE: 192
INCLUDED REGION SIZE: 192

PRODUCT SIZE: 139, PAIR ANY COMPL: 4.00, PAIR 3' COMPL: 2.00
   1 ACTCTGCTCCCAGTGTGAACATGGGGAAAGTTGATTAAACTCTCTGACTTCAGATTCCTC
                       >>>>>>>>>>>>>>>>>>>>

61 aTGTAAAATGTGGGGAAACAGCTCTGACTTAATGGTGTCACTGTGAGGAGTAAATGAGGT

121 AgCATATTTAAAGGATTTTGTATAGTGCTGGTGACAGTAACCAGCCAATAGATGATATAG
                       <<<<<<<<<<<<<<<<<<<<<<

181 CTAGTAATAGCA

77) Whole sequence ::: rs9976207-rs455473
``` cttcactgaccacttccttaactgtccactccgaaacaccCcttcttcctgttcttccaa
tacaccaaactctttcttgcctctgtgtgcttgcccatgctgttccttctggcttcttcc
ttcACATTCAAGTCTTGACTTAGATGTCACTTGCCAAGGGAGACCTTGGA
(SEQ ID NO: 220)

```
OLIGO          start len   tm    gc %  any   3' seq (SEQ ID NOs: 221, 222)

LEFT PRIMER     12   21  54.96  47.62  4.00  0.00 acttccttaactgtccactcc
RIGHT PRIMER   159   19  54.64  47.37  7.00  2.00 CCTTGGCAAGTGACATCTA
SEQUENCE SIZE: 170
INCLUDED REGION SIZE: 170

PRODUCT SIZE: 148, PAIR ANY COMPL: 5.00, PAIR 3' COMPL: 3.00
   1 cttcactgaccacttccttaactgtccactccgaaacaccCcttcttcctgttcttccaa
                  >>>>>>>>>>>>>>>>>>>>>

61 tacaccaaactctttcttgcctctgtgtgcttgcccatgctgttccttctggcttcttcc 121 ttcACATTCAAGTCTTGACTTAGATGTCACTTGCCAAGGGAGACCTTGGA
                              <<<<<<<<<<<<<<<<<<<
```

TABLE 2-continued

78) Whole sequence ::: rs2837807-rs2837808

AAACATCCCAATAGACAAAACTCCAAGAAGAGTCAAAACAAGAATAAAGTaCAGGTCATC
TTTTCTTTTGCACTCCTGACAGCACTTTGTACATGGTAATAATAATCTACCAATTAACTA
CATAAGCCACATGGTTTTATcATAGTGTGAAGCTTTGTATCCAGAAAGGAGAGAAGGCTCC
(SEQ ID NO: 223)

```
OLIGO          start   len   tm     gc %   any    3'    seq (SEQ ID NOs: 224, 225)

LEFT PRIMER      23     22   56.31  36.36  3.00   0.00  CCAAGAAGAGTCAAAACAAGAA
RIGHT PRIMER    172     21   56.19  42.86  4.00   2.00  TCTCCTTTCTGGATACAAAGC
SEQUENCE SIZE: 181
INCLUDED REGION SIZE: 181

PRODUCT SIZE: 150, PAIR ANY COMPL: 5.00, PAIR 3' COMPL: 1.00
   1 AAACATCCCAATAGACAAAACTCCAAGAAGAGTCAAAACAAGAATAAAGTaCAGGTCATC
                            >>>>>>>>>>>>>>>>>>>>>>

61 TTTTCTTTTGCACTCCTGACAGCACTTTGTACATGGTAATAATAATCTACCAATTAACTA

121 CATAAGCCACATGGTTTTATcATAGTGTGAAGCTTTGTATCCAGAAAGGAGAGAAGGCTC
                                          <<<<<<<<<<<<<<<<<<<<<

181 C
```

79) Whole sequence ::: rs9974587-rs2776356

GGCAGAGGCATGGGGTGCATAGGGATATGGGGTGGGCCAGTTTGCTCCTCAGACCAGAAG
GGGTGCAGGAcTCCCCCCGATCAGGATCaTGGAGAAAGGTGTGGACAGAGGAAGGGAGGG
AGGGAGAAATGGCAGCTGCCCTGCAGTGG (SEQ ID NO: 226)

```
OLIGO          start   len   tm     gc %   any    3'    seq (SEQ ID NOs: 227, 228)

LEFT PRIMER      42     20   60.52  55.00  3.00   2.00  TTGCTCCTCAGACCAGAAGG
RIGHT PRIMER    118     20   59.68  60.00  4.00   2.00  CTCCCTTCCTCTGTCCACAC
SEQUENCE SIZE: 149
INCLUDED REGION SIZE: 149

PRODUCT SIZE: 77, PAIR ANY COMPL: 5.00, PAIR 3' COMPL: 1.00
   1 GGCAGAGGCATGGGGTGCATAGGGATATGGGGTGGGCCAGTTTGCTCCTCAGACCAGAAG
                                              >>>>>>>>>>>>>>>>>>>>

61 GGGTGCAGGAcTCCCCCCGATCAGGATCaTGGAGAAAGGTGTGGACAGAGGAAGGGAGGG
     >                                  <<<<<<<<<<<<<<<<<<<<

121 AGGGAGAAATGGCAGCTGCCCTGCAGTGG
```

80) Whole sequence ::: rs2838089-rs2838090 cagggactaagtgtctctgacaatacattcagccactactAcagtatgaagccagcccct
catccccaccttcagagacccctggtgcctcagattcctcggccattctggagctgctgt
gCCCGAGGCTTGTGTAGTTGGAGATCATTTTGGCAGTCAGTGCTG (SEQ ID NO: 229)

```
OLIGO          start   len   tm     gc %   any    3'    seq (SEQ ID NOs: 230, 231)

LEFT PRIMER      12     22   55.48  40.91  5.00   2.00  tgtctctgacaatacattcagc
RIGHT PRIMER    160     20   55.81  45.00  4.00   2.00  CTGACTGCCAAAATGATCTC
SEQUENCE SIZE: 165
INCLUDED REGION SIZE: 165

PRODUCT SIZE: 149, PAIR ANY COMPL: 5.00, PAIR 3' COMPL: 1.00
   1 cagggactaagtgtctctgacaatacattcagccactactAcagtatgaagccagcccct
                 >>>>>>>>>>>>>>>>>>>>>>

61 catccccaccttcagagacccctggtgcctcagattcctcggccattctggagctgctgt 121 gCCCGAGGCTTGTGTAGTTGGAGATCATTTTGGCAGTCAGTGCTG
                             <<<<<<<<<<<<<<<<<<<<
```

12th group

81) Whole sequence ::: rs453592-rs380152

CCTGTCTCCGTGCGTGAAAGCCGGCTCCAAAGTGCCTTCTGTCCTATCTGCCTTCcGCAC
CTGGCTTTCCTGAAAGAAAGAAAACGCGTGGCTTATCTTTTCACGGCACGCCACCTTCAC
TCTCaCTTTTTCTTTTCTAATAAATACCTCTGGATGGGTTAGTGGTAATCTCTCCTCAAAC
(SEQ ID NO: 232)

TABLE 2-continued

```
OLIGO            start  len   tm    gc %  any   3'   seq (SEQ ID NOs: 233, 234)

LEFT PRIMER       24    20  60.00  55.00  4.00  1.00  GCTCCAAAGTGCCTTCTGTC
RIGHT PRIMER     165    20  58.87  55.00  3.00  2.00  CCACTAACCCATCCAGAGGT
SEQUENCE SIZE: 181
INCLUDED REGION SIZE: 181

PRODUCT SIZE: 142, PAIR ANY COMPL: 4.00, PAIR 3' COMPL: 1.00
    1 CCTGTCTCCGTGCGTGAAAGCCGGCTCCAAAGTGCCTTCTGTCCTATCTGCCTTCcGCAC
                              >>>>>>>>>>>>>>>>>>>>

61 CTGGCTTTCCTGAAAGAAAGAAAACGCGTGGCTTATCTTTTCACGGCACGCCACCTTCAC

121 TCTCaCTTTTTCTTTTCTAATAAATACCTCTGGATGGGTTAGTGGTAATCTCTCCTCAAA
                              <<<<<<<<<<<<<<<<<<<<

181 C
```

82) Whole sequence ::: rs442723-rs449888

```
GGGAGCACAACCTAGGCCCCTCCTGGGGAGGTGGTGGAGTCAGAATCACGTAAGAGaCAA
AGTTCCAGTCCCTCAGTGCCGGCTCCATTGTCCCCTGGACTTCCCTTACAAACCACAGAT
GCAAAGAGAGCACTTCTCgGAATCTCCACACAGCCACGGTGGAGCACTCAACCCACGCGA
CCCTCGGGCGCAGGTGCT (SEQ ID NO: 235)
```

```
OLIGO            start  len   tm    gc %  any   3'   seq (SEQ ID NOs: 236, 237)

LEFT PRIMER       23    20  65.82  65.00  3.00  1.00  CTGGGGAGGTGGTGGAGTCA
RIGHT PRIMER     169    20  66.12  65.00  7.00  1.00  GAGTGCTCCACCGTGGCTGT
SEQUENCE SIZE: 198
INCLUDED REGION SIZE: 198

PRODUCT SIZE: 147, PAIR ANY COMPL: 7.00, PAIR 3' COMPL: 1.00
    1 GGGAGCACAACCTAGGCCCCTCCTGGGGAGGTGGTGGAGTCAGAATCACGTAAGAGaCAA
                             >>>>>>>>>>>>>>>>>>>>

61 AGTTCCAGTCCCTCAGTGCCGGCTCCATTGTCCCCTGGACTTCCCTTACAAACCACAGAT

121 GCAAAGAGAGCACTTCTCgGAATCTCCACACAGCCACGGTGGAGCACTCAACCCACGCGA
                                      <<<<<<<<<<<<<<<<<<<<

181 CCCTCGGGCGCAGGTGCT
```

83) Whole sequence ::: rs375886-rs9976560

```
CCTGAGAAGCTTCCAGCAAAGCACCAGCACGAACCGCCCCACCTCCCCACCTCCCCGCAA
GCGTTGcCGGGACTGACAGATTACAGAGCTCTGgTCCCTCTGCACTCCTGCTCTGCCACC
CCCAGGGTGTCAGAATGTGCCCCCCACACAGTTTCCAAAAG (SEQ ID NO: 238)
```

```
OLIGO            start  len   tm    gc %  any   3'   seq (SEQ ID NOs: 239, 240)

LEFT PRIMER       18    18  59.84  55.56  2.00  0.00  AAAGCACCAGCACGAACC
RIGHT PRIMER     143    18  59.89  61.11  3.00  3.00  GGGGCACATTCTGACACC
SEQUENCE SIZE: 161
INCLUDED REGION SIZE: 161

PRODUCT SIZE: 126, PAIR ANY COMPL: 3.00, PAIR 3' COMPL: 0.00
    1 CCTGAGAAGCTTCCAGCAAAGCACCAGCACGAACCGCCCCACCTCCCCACCTCCCCGCAA
                        >>>>>>>>>>>>>>>>>>

61 GCGTTGcCGGGACTGACAGATTACAGAGCTCTGgTCCCTCTGCACTCCTGCTCTGCCACC

121 CCCAGGGTGTCAGAATGTGCCCCCCACACAGTTTCCAAAAG
            <<<<<<<<<<<<<<<<<<
```

84) Whole sequence ::: rs3819900-rs3819901

```
ATGGAGCTGCTGCGCCGGCCTGAGCTCTGATCCCTCCTCCGACCCAGCCTCACCCTGCaA
GCAGCACCATGTGGGGCTCAGAATGGGATCTTAAGGGACCCTcCCCACAACCTCCCGAT
AAGCCTTTCCACGGAGGGCCCAAGCGGAGACAGGAGAACACT (SEQ ID NO: 241)
```

```
OLIGO            start  len   tm    gc %  any   3'   seq (SEQ ID NOs: 242, 243)

LEFT PRIMER       20    19  57.00  57.89  6.00  0.00  CTGAGCTCTGATCCCTCCT
RIGHT PRIMER     158    18  57.51  55.56  2.00  0.00  TTCTCCTGTCTCCGCTTG
SEQUENCE SIZE: 162
INCLUDED REGION SIZE: 162
```

TABLE 2-continued

```
PRODUCT SIZE: 139, PAIR ANY COMPL: 3.00, PAIR 3' COMPL: 0.00
   1 ATGGAGCTGCTGCGCCGGCCTGAGCTCTGATCCCTCCTCCGACCCAGCCTCACCCTGCaA
                       >>>>>>>>>>>>>>>>>>>>

61 GCAGCACCATGTGGGGCTCAGAATGGGGATCTTAAGGGACCCTcCCCACAACCTCCCGAT

121 AAGCCTTTCCACGGAGGGCCCAAGCGGAGACAGGAGAACACT
                       <<<<<<<<<<<<<<<<<<<

85) Whole sequence ::: rs10451852-rs10451853

ACTTTCAGAATGTGCTGCCTTCCACGTGTGAACCAGACTGAGCTCCTTTCTGCCACTGAT
GTTGAATTGTCCATTTGCTCACaTCAGTGTCCACGTGGCAAATCCACAGGGCgTGGGTGG
GATCCTGCAGTCTAGACAAAGCCAAGGAGCACCGCTGGAGGCCACGTTGGGCTTCCCAAT
CCACATGCAAACCC (SEQ ID NO: 244)

OLIGO           start  len  tm     gc %   any  3'   seq (SEQ ID NOs: 245, 246)

LEFT PRIMER       45   20  59.29  50.00  3.00 1.00 CCTTTCTGCCACTGATGTTG
RIGHT PRIMER     190   19  60.46  47.37  4.00 0.00 TTGCATGTGGATTGGGAAG
SEQUENCE SIZE: 194
INCLUDED REGION SIZE: 194

PRODUCT SIZE: 146, PAIR ANY COMPL: 4.00, PAIR 3' COMPL:.0.00
   1 ACTTTCAGAATGTGCTGCCTTCCACGTGTGAACCAGACTGAGCTCCTTTCTGCCACTGAT
                                              >>>>>>>>>>>>>>>>

61 GTTGAATTGTCCATTTGCTCACaTCAGTGTCCACGTGGCAAATCCACAGGGCgTGGGTGG
     >>>>

121 GATCCTGCAGTCTAGACAAAGCCAAGGAGCACCGCTGGAGGCCACGTTGGGCTTCCCAAT
                                                      <<<<<<<<

181 CCACATGCAAACCC
     <<<<<<<<<

86) Whole sequence ::: rs7278528-rs11701158

TCTCCAGCCAGCGTGTCACAAAGCCGCTCACCTGCTCGTGTGAGTGTCTGAATGCACGTG
TTTGAGTGTCAGaGGCGTGTGAACCACAGCAACTCAATCTTGAATAGGGGCTGGGTAAAG
TGAGGCTgAGACCTCCCGGGGCTGCATTCCCAGATGGTTAAGGCATTCTAAGTCACAAGA
TGAGATAGGAAGTTCGCACAAGACACTGGTCAT (SEQ ID NO: 247)

OLIGO           start  len  tm     gc %   any  3'   seq (SEQ ID NOs: 248, 249)

LEFT PRIMER       28   20  60.53  55.00  4.00 0.00 TCACCTGCTCGTGTGAGTGT
RIGHT PRIMER     163   20  59.39  50.00  4.00 2.00 CCTTAACCATCTGGGAATGC
SEQUENCE SIZE: 213
INCLUDED REGION SIZE: 213

PRODUCT SIZE: 136, PAIR ANY COMPL: 3.00, PAIR 3' COMPL: 0.00
   1 TCTCCAGCCAGCGTGTCACAAAGCCGCTCACCTGCTCGTGTGAGTGTCTGAATGCACGTG
                           >>>>>>>>>>>>>>>>>>>>

61 TTTGAGTGTCAGaGGCGTGTGAACCACAGCAACTCAATCTTGAATAGGGGCTGGGTAAAG

121 TGAGGCTgAGACCTCCCGGGGCTGCATTCCCAGATGGTTAAGGCATTCTAAGTCACAAGA
                                   <<<<<<<<<<<<<<<<<<<<

181 TGAGATAGGAAGTTCGCACAAGACACTGGTCAT

87) Whole sequence ::: rs2839627-rs170916

TTGAGTCCTCTTAAGTAGTTACTATAGTGGAGAACTTGAGTCATTCTTTGTAGCGTGCTT
cGTAGAGCAGCGTGTTTGTTAGAAGGATTTGTTAATCCTGTATAGgGTCTTTACGAAGGC
TGTTTTCATGGAAGCTTCTCTTTGTTGACTCC (SEQ ID NO: 250)

OLIGO           start  len  tm     gc %   any  3'   seq (SEQ ID NOs: 251, 252)

LEFT PRIMER       28   22  55.68  36.36  5.00 1.00 TGGAGAACTTGAGTCATTCTTT
RIGHT PRIMER     152   19  52.33  47.37  3.00 2.00 GGAGTCAACAAAGAGAAGC
SEQUENCE SIZE: 152
INCLUDED REGION SIZE: 152

PRODUCT SIZE: 125, PAIR ANY COMPL: 5.00, PAIR 3' COMPL: 3.00
   1 TTGAGTCCTCTTAAGTAGTTACTATAGTGGAGAACTTGAGTCATTCTTTGTAGCGTGCTT
                               >>>>>>>>>>>>>>>>>>>>>>
```

TABLE 2-continued

```
 61 cGTAGAGCAGCGTGTTTGTTAGAAGGATTTGTTAATCCTGTATAGgGTCTTTACGAAGGC

121 TGTTTTCATGGAAGCTTCTCTTTGTTGACTCC
                  <<<<<<<<<<<<<<<<<<<
```

88) Whole sequence ::: rs2839628-rs234740

```
CATTCTCTCCAGCTGCAAACTTTCTTCAACTTTCCTAAATTCTTAcTAAATTCAGAGGAA
TAGGATAAAGATCACTTAGAGAAAGGGTGCTTATGGACATAGCCTGAGTTTCCTTTAACC
TCTCTgCAATGGGTGCTTTTAACTAGCTTCTACATGGCAAGCTGTTTCAGTTTG
(SEQ ID NO: 253)

OLIGO           start len   tm    gc %  any  3'  seq (SEQ ID NOs: 254, 255)

LEFT PRIMER       20   21  50.06  28.57 3.00 2.00 CTTTCTTCAACTTTCCTAAAT
RIGHT PRIMER     160   19  50.96  42.11 4.00 2.00 TTGCCATGTAGAAGCTAGT
SEQUENCE SIZE: 174
INCLUDED REGION SIZE: 174

PRODUCT SIZE: 141, PAIR ANY COMPL: 5.00, PAIR 3' COMPL: 2.00
   1 CATTCTCTCCAGCTGCAAACTTTCTTCAACTTTCCTAAATTCTTAcTAAATTCAGAGGAA
                     >>>>>>>>>>>>>>>>>>>>>

61 TAGGATAAAGATCACTTAGAGAAAGGGTGCTTATGGACATAGCCTGAGTTTCCTTTAACC

121 TCTCTgCAATGGGTGCTTTTAACTAGCTTCTACATGGCAAGCTGTTTCAGTTTG
                       <<<<<<<<<<<<<<<<<<<
```

89) Whole sequence ::: rs2838239-rs2838240

```
GGACATCTGGAACTGCACCAGCACAGAACCGACACGTTGTTAcTCATCGTCACTCGGCAG
GGCTGAAGACCACCAGAACTCATGACAGGCAGACGTGCCTGGCCCAGTTGAGGATGTAGC
tTCAGAGCCAAGCGCCAGTCCTGTTGGCCACGTGGGCTGGGGGCAGGATAGACCA
(SEQ ID NO: 256)

OLIGO           start len   tm    gc %  any  3'  seq (SEQ ID NOs: 257, 258)

LEFT PRIMER       17   19  59.73  57.89 2.00 0.00 ACCAGCACAGAACCGACAC
RIGHT PRIMER     145   18  62.40  61.11 4.00 0.00 AACAGGACTGGCGCTTGG
SEQUENCE SIZE: 175
INCLUDED REGION SIZE: 175

PRODUCT SIZE: 129, PAIR ANY COMPL: 4.00, PAIR 3' COMPL: 1.00
   1 GGACATCTGGAACTGCACCAGCACAGAACCGACACGTTGTTAcTCATCGTCACTCGGCAG
                     >>>>>>>>>>>>>>>>>>>

61 GGCTGAAGACCACCAGAACTCATGACAGGCAGACGTGCCTGGCCCAGTTGAGGATGTAGC 121 tTCAGAGCCAAGCGCCAGTCCTGTTGGCCACGTGGGCTGGGGGCAGGATAGACCA
                     <<<<<<<<<<<<<<<<<<
```

90) Whole sequence ::: rs630397-rs11089106

```
GGCTGGTTCTGCCCTTGGGAGGTGGTTCCTTTGGCTGGACCAGAATGTCTGaAGATGATC
AGGAGAGGGCCAAGGGTTGGGGGGTGCCCCATGTGCACCCTGAGAATTGCACCAGGCACA
GtGAGCAACTTCAGCCCTCCTTGTGCAGAGCTGCAGCGTACAGTGCCAGCCCTCGCTGGC
CC (SEQ ID NO: 259)

OLIGO           start len   tm    gc %  any  3'  seq (SEQ ID NOs: 260, 261)

LEFT PRIMER       14   20  61.79  55.00 3.00 0.00 CTTGGGAGGTGGTTCCTTTG
RIGHT PRIMER     148   18  61.15  61.11 4.00 1.00 CTGCACAAGGAGGGCTGA
SEQUENCE SIZE: 182
INCLUDED REGION SIZE: 182

PRODUCT SIZE: 135, PAIR ANY COMPL: 5.00, PAIR 3' COMPL: 0.00
   1 GGCTGGTTCTGCCCTTGGGAGGTGGTTCCTTTGGCTGGACCAGAATGTCTGaAGATGATC
                  >>>>>>>>>>>>>>>>>>>>

61 AGGAGAGGGCCAAGGGTTGGGGGGTGCCCCATGTGCACCCTGAGAATTGCACCAGGCACA

121 GtGAGCAACTTCAGCCCTCCTTGTGCAGAGCTGCAGCGTACAGTGCCAGCCCTCGCTGGC
                    <<<<<<<<<<<<<<<<<<

181 CC
```

TABLE 2-continued

91) Whole sequence ::: rs9637180-rs481767

GTTCTCACTTTACTGAGAAACCTGGCAGCTTCTCAGGCCACCGCCCAGGTCACCTGCTCA
CCAGCAAcGTGAACCACAGGAActGAGGCTGTGCGGGAGGCGGCTCTGCTCTGTGCTGGG
CCCCCCTCCTCCTCACTCACCCTCTTCAGTCAAAG (SEQ ID NO: 262)

| OLIGO | start | len | tm | gc % | any | 3' | seq (SEQ ID NOs: 263, 264) |
|---|---|---|---|---|---|---|---|
| LEFT PRIMER | 11 | 20 | 57.70 | 50.00 | 5.00 | 5.00 | TACTGAGAAACCTGGCAGCT |
| RIGHT PRIMER | 155 | 20 | 54.98 | 50.00 | 3.00 | 0.00 | CTTTGACTGAAGAGGGTGAG |

SEQUENCE SIZE: 155
INCLUDED REGION SIZE: 155

PRODUCT SIZE: 145, PAIR ANY COMPL: 3.00, PAIR 3' COMPL: 2.00
```
  1 GTTCTCACTTTACTGAGAAACCTGGCAGCTTCTCAGGCCACCGCCCAGGTCACCTGCTCA
               >>>>>>>>>>>>>>>>>>>>

61 CCAGCAAcGTGAACCACAGGAActGAGGCTGTGCGGGAGGCGGCTCTGCTCTGTGCTGGG

121 CCCCCCTCCTCCTCACTCACCCTCTTCAGTCAAAG
                  <<<<<<<<<<<<<<<<<<<<
```

92) Whole sequence ::: rs162360-rs162359

TTAGTATTATTATTTTCATATATATTTTTTATAATAATCATATATTCAATTTTATCATCA
AGAAAAAAGTTTTAAAATTCaAAATCCTTTCATGTGCACTGTTTTAAACTtAGGTAGAAG
AAAAAAAGTCACTGAAAATCCAAGATGTAATAAACAGGCCCAACAAAGGCCAACAAACTT
(SEQ ID NO: 265)

| OLIGO | start | len | tm | gc % | any | 3' | seq (SEQ ID NOs: 266, 267) |
|---|---|---|---|---|---|---|---|
| LEFT PRIMER | 45 | 20 | 48.37 | 20.00 | 5.00 | 3.00 | TTCAATTTTATCATCAAGAA |
| RIGHT PRIMER | 163 | 20 | 55.18 | 40.00 | 4.00 | 1.00 | TTGGGCCTGTTTATTACATC |

SEQUENCE SIZE: 180
INCLUDED REGION SIZE: 180

PRODUCT SIZE: 119, PAIR ANY COMPL: 4.00, PAIR 3' COMPL: 1.00
```
  1 TTAGTATTATTATTTTCATATATATTTTTTATAATAATCATATATTCAATTTTATCATCA
                                                  >>>>>>>>>>>>>>>>

61 AGAAAAAAGTTTTAAAATTCaAAATCCTTTCATGTGCACTGTTTTAAACTtAGGTAGAAG
    >>>>

121 AAAAAAAGTCACTGAAAATCCAAGATGTAATAAACAGGCCCAACAAAGGCCAACAAACTT
                      <<<<<<<<<<<<<<<<<<<<
```

93) Whole sequence ::: rs162356-rs162355

AGGGAACATGGCCTTGCCCACACAGATTTCAGACATCTGGCTCCAGAACTGTGGGAGGAC
ACATTTCTGTTGTTTAGAACTGCaTGTTTTTTATACTTTGTTATGGCTGCCCTAGGcAAC
TAATACAGATATTATTTTCCACTTCTGAACTTAGCAAAATATTTTTAAAATGAAAATTCT
TAAATGTTGGCACAGT (SEQ ID NO: 268)

| OLIGO | start | len | tm | gc % | any | 3' | seq (SEQ ID NOs: 269, 270) |
|---|---|---|---|---|---|---|---|
| LEFT PRIMER | 14 | 20 | 60.24 | 45.00 | 3.00 | 3.00 | TTGCCCACACAGATTTCAGA |
| RIGHT PRIMER | 156 | 22 | 56.88 | 36.36 | 5.00 | 0.00 | TGCTAAGTTCAGAAGTGGAAAA |

SEQUENCE SIZE: 196
INCLUDED REGION SIZE: 196

PRODUCT SIZE: 143, PAIR ANY COMPL: 4.00, PAIR 3' COMPL: 2.00
```
  1 AGGGAACATGGCCTTGCCCACACAGATTTCAGACATCTGGCTCCAGAACTGTGGGAGGAC
                  >>>>>>>>>>>>>>>>>>>>

61 ACATTTCTGTTGTTTAGAACTGCaTGTTTTTTATACTTTGTTATGGCTGCCCTAGGcAAC

121 TAATACAGATATTATTTTCCACTTCTGAACTTAGCAAAATATTTTTAAAATGAAAATTCT
                      <<<<<<<<<<<<<<<<<<<<<<

181 TAAATGTTGGCACAGT
```

TABLE 2-continued

94) Whole sequence ::: rs91424-rs463738

CTGGATAAAGGATGCTACACGTCCCTGGTGGGACAGAGCAGGACGGCAGGGGATTTCATT
AcGCCAcTCAGAATGGCAGGCAATTGAAAAAACTTATAAATTGTTTATTTCCAGAATTTT
(SEQ ID NO: 271)

| OLIGO | start | len | tm | gc % | any | 3' | seq (SEQ ID NOs: 272, 273) |
|---|---|---|---|---|---|---|---|
| LEFT PRIMER | 3 | 20 | 54.33 | 45.00 | 4.00 | 4.00 | GGATAAAGGATGCTACACGT |
| RIGHT PRIMER | 120 | 20 | 49.40 | 20.00 | 4.00 | 0.00 | AAAATTCTGGAAATAAACAA |

SEQUENCE SIZE: 120
INCLUDED REGION SIZE: 120

PRODUCT SIZE: 118, PAIR ANY COMPL: 3.00, PAIR 3' COMPL: 1.00
```
  1 CTGGATAAAGGATGCTACACGTCCCTGGTGGGACAGAGCAGGACGGCAGGGGATTTCATT
    >>>>>>>>>>>>>>>>>>>>

61 AcGCCAcTCAGAATGGCAGGCAATTGAAAAAACTTATAAATTGTTTATTTCCAGAATTTT
                                                 <<<<<<<<<<<<<<<<<<<<
```

95) Whole sequence ::: rs2838318-rs2838319

TGTCAGTGGTGTAATCCGACTGTGAAAGATCAGTCTAACAAAACAGCGGGGAGAGAGAGG
GCTGAATCAGAGCaACTAGGTCCAAAGCCGAGGGAACCACCAACAGATCCCCTGGTGACC
CAACAAGAAATGCTCACAGTCTGGACCCAgTCAGAGTCTGCAGGACACAGCAGACATTCT
GGAAGTTACAACAGCCAGGAGCAAGAGGACGCATGGCCTGACTG (SEQ ID NO: 274)

| OLIGO | start | len | tm | gc % | any | 3' | seq (SEQ ID NOs: 275, 276) |
|---|---|---|---|---|---|---|---|
| LEFT PRIMER | 49 | 20 | 60.30 | 60.00 | 3.00 | 3.00 | GGGAGAGAGAGGGCTGAATC |
| RIGHT PRIMER | 202 | 21 | 59.00 | 52.38 | 4.00 | 2.00 | GCTCCTGGCTGTTGTAACTTC |

SEQUENCE SIZE: 224
INCLUDED REGION SIZE: 224

PRODUCT SIZE: 154, PAIR ANY COMPL: 4.00, PAIR 3' COMPL: 1.00
```
  1 TGTCAGTGGTGTAATCCGACTGTGAAAGATCAGTCTAACAAAACAGCGGGGAGAGAGAGG
                                                       >>>>>>>>>>

61 GCTGAATCAGAGCaACTAGGTCCAAAGCCGAGGGAACCACCAACAGATCCCCTGGTGACC
    >>>>>>>>

121 CAACAAGAAATGCTCACAGTCTGGACCCAgTCAGAGTCTGCAGGACACAGCAGACATTCT

181 GGAAGTTACAACAGCCAGGAGCAAGAGGACGCATGGCCTGACTG
    <<<<<<<<<<<<<<<<<<<<<
```

96) Whole sequence ::: rs915770-rs731935

CGCCAGAGCACCCCTTCTCAGAACAGAAAGCGTCTCTACAaAGTGATCCGGAAGTGAGTG
TGTGAGGGCGCTGCGTCCTCCCTGCTCCCCTTGGAGTTGCCCTTTCTTGCTCAGATCTGG
GTGCCTTgGCCTTGTCCTGGGCCCTTCCGCAGCCCCCGGGGTGATCCCCGCTAG
(SEQ ID NO: 277)

| OLIGO | start | len | tm | gc % | any | 3' | seq (SEQ ID NOs: 278, 279) |
|---|---|---|---|---|---|---|---|
| LEFT PRIMER | 3 | 19 | 60.95 | 63.16 | 3.00 | 3.00 | CCAGAGCACCCCTTCTCAG |
| RIGHT PRIMER | 148 | 18 | 62.95 | 66.67 | 6.00 | 0.00 | GGAAGGGCCCAGGACAAG |

SEQUENCE SIZE: 174
INCLUDED REGION SIZE: 174

PRODUCT SIZE: 146, PAIR ANY COMPL: 6.00, PAIR 3' COMPL: 2.00
```
  1 CGCCAGAGCACCCCTTCTCAGAACAGAAAGCGTCTCTACAaAGTGATCCGGAAGTGAGTG
      >>>>>>>>>>>>>>>>>>>

61 TGTGAGGGCGCTGCGTCCTCCCTGCTCCCCTTGGAGTTGCCCTTTCTTGCTCAGATCTGG

121 GTGCCTTgGCCTTGTCCTGGGCCCTTCCGCAGCCCCCGGGGTGATCCCCGCTAG
            <<<<<<<<<<<<<<<<<<
```

Final Set

97) Whole sequence ::: rs1573338-rs1573339

TATCTTACGGATTTGTCAACATCATTTGAGAAGAAGTCCATAGGCTCAGCAGATTTTTAT
GCCAGGTGGGCCATGGCATAAAAATGTGAAGAATGTGCTCaCTTAGACAATACcTGTGCT
AAAATTGGAACAATACAGAGAAGATTAGCAAATTAAAACAATGTTAGGAAGTCAGTGTGG
TGAGGTACGGTGCCTCATGCC (SEQ ID NO: 280)

TABLE 2-continued

```
OLIGO           start len  tm    gc %  any  3'   seq (SEQ ID NOs: 281, 282)

LEFT PRIMER        47   21 59.24 42.86 3.00 1.00 CAGCAGATTTTTATGCCAGGT
RIGHT PRIMER      192   20 60.06 60.00 4.00 3.00 CACCGTACCTCACCACACTG
SEQUENCE SIZE: 201
INCLUDED REGION SIZE: 201

PRODUCT SIZE: 146, PAIR ANY COMPL: 4.00, PAIR 3' COMPL: 3.00
   1 TATCTTACGGATTTGTCAACATCATTTGAGAAGAAGTCCATAGGCTCAGCAGATTTTTAT
                                                 >>>>>>>>>>>>>

61 GCCAGGTGGGCCATGGCATAAAAATGTGAAGAATGTGCTCaCTTAGACAATACcTGTGCT
     >>>>>>>

121 AAAATTGGAACAATACAGAGAAGATTAGCAAATTAAAACAATGTTAGGAAGTCAGTGTGG
                                                         <<<<<<<<

181 TGAGGTACGGTGCCTCATGCC
     <<<<<<<<<<<
```

98) Whole sequence ::: rs3788094-rs3788095

AGGCAGGGCCCTCCTTGCCACATGTAAAGCTGCACAGAGCGGTCACTATATGTGTTTCCA
TATTTGCAATCCAACCACCACCAACTGAGTGTGCGTCCTGaTCAGCCGAGCCTGCCCACG
GTGGCCACAGGCCCTCTACATTCTAATCTCGAGAGCCTGAGCATGTACAAATTAAACgAA
GCAAAACGACACCACCCAGTTCTGGCCGTACTATAGGAGGTTTTCCAGGAAGGGTTTGTGA
ACATAAACATAAGCTAGGTAACACTCCTTTCTGAA (SEQ ID NO: 283)

```
OLIGO           start len  tm    gc %  any  3'   seq (SEQ ID NOs: 284, 285)

LEFT PRIMER        73   20 57.88 50.00 5.00 3.00 AACCACCACCAACTGAGTGT
RIGHT PRIMER      220   20 56.94 55.00 6.00 2.00 CCTCCTATAGTACGGCCAGA
SEQUENCE SIZE: 275
INCLUDED REGION SIZE: 275

PRODUCT SIZE: 148, PAIR ANY COMPL: 3.00, PAIR 3' COMPL: 1.00
   1 AGGCAGGGCCCTCCTTGCCACATGTAAAGCTGCACAGAGCGGTCACTATATGTGTTTCCA

61 TATTTGCAATCCAACCACCACCAACTGAGTGTGCGTCCTGaTCAGCCGAGCCTGCCCACG
                   >>>>>>>>>>>>>>>>>>>>

121 GTGGCCACAGGCCCTCTACATTCTAATCTCGAGAGCCTGAGCATGTACAAATTAAACgAA

181 GCAAAACGACACCACCCAGTTCTGGCCGTACTATAGGAGGTTTTCCAGGAAGGGTTTGTGA
                              <<<<<<<<<<<<<<<<<<<<

241 ACATAAACATAAGCTAGGTAACACTCCTTTCTGAA
```

99) Whole sequence ::: rs756554-rs756555

TCAGAGCATCGCCTCAGTGGCCATCAATAGCTCGGGGGACTGGATTGCTTTTGGCTGTTC
AGGTTTGTCCCCaGCCTGGGTGGTAGAGATGGACTCCCCATTAGGGACCAGTGCTGCCCG
GCTACAGGCtTACTTGACAGCCACCCACTGGGGGTGCCCTCCCCTCCCCCAGTTGTCTTC
CATGGGGTGCCCTCTCCCCCAGCCGCCTTTCAGAAGGGGCCCTCCCCTCC
(SEQ ID NO: 286)

```
OLIGO           start len  tm    gc %  any  3'   seq (SEQ ID NOs: 287, 288)

LEFT PRIMER        41   20 61.15 45.00 2.00 0.00 TGGATTGCTTTTGGCTGTTC
RIGHT PRIMER      189   20 61.37 55.00 6.00 2.00 CACCCCATGGAAGACAACTG
SEQUENCE SIZE: 230
INCLUDED REGION SIZE: 230

PRODUCT SIZE: 149, PAIR ANY COMPL: 4.00, PAIR 3' COMPL: 2.00
   1 TCAGAGCATCGCCTCAGTGGCCATCAATAGCTCGGGGGACTGGATTGCTTTTGGCTGTTC
                                             >>>>>>>>>>>>>>>>>>>>

61 AGGTTTGTCCCCaGCCTGGGTGGTAGAGATGGACTCCCCATTAGGGACCAGTGCTGCCCG

121 GCTACAGGCtTACTTGACAGCCACCCACTGGGGGTGCCCTCCCCTCCCCCAGTTGTCTTC
                                                      <<<<<<<<<<

181 CATGGGGTGCCCTCTCCCCCAGCCGCCTTTCAGAAGGGGCCCTCCCCTCC
     <<<<<<<<<<
```

TABLE 2-continued

100) Whole sequence ::: rs4350841-rs2838545

CTCATGCTTACATCCTTAGCTGATCATTAAACTTTGTGACCATTTCATGCTCACTGCTTT
CTTGCCcGGGAGCTAATGGTGAGGAAAGGTCACTGGGAACCAGCGCACCAACCTCAGACA
TcGATTTTGTTCCAGCCTTTTTTCCTGGGCAGGGGTGGCTATCACCTGCTGGTAGGCAGC
GGCAGGCCCACTGTCCTGC (SEQ ID NO: 289)

| OLIGO | start | len | tm | gc % | any | 3' | seq (SEQ ID NOs: 290, 291) |
|---|---|---|---|---|---|---|---|
| LEFT PRIMER | 27 | 21 | 53.45 | 28.57 | 5.00 | 2.00 | TTAAACTTTGTGACCATTTCA |
| RIGHT PRIMER | 174 | 18 | 54.55 | 55.56 | 6.00 | 2.00 | TACCAGCAGGTGATAGCC |

SEQUENCE SIZE: 199
INCLUDED REGION SIZE: 199

PRODUCT SIZE: 148, PAIR ANY COMPL: 3.00, PAIR 3' COMPL: 0.00
```
  1 CTCATGCTTACATCCTTAGCTGATCATTAAACTTTGTGACCATTTCATGCTCACTGCTTT
                                 >>>>>>>>>>>>>>>>>>>>>

61 CTTGCCcGGGAGCTAATGGTGAGGAAAGGTCACTGGGAACCAGCGCACCAACCTCAGACA

121 TcGATTTTGTTCCAGCCTTTTTTCCTGGGCAGGGGTGGCTATCACCTGCTGGTAGGCAGC
                                           <<<<<<<<<<<<<<<<<<

181 GGCAGGCCCACTGTCCTGC
```

101) Whole sequence ::: rs2838551-rs2838552

TGACAGAAAAGTCTCAGAGCAGTGCCTTCTGAGCTCTTCTACACCAAGCAGGCAGAATGT
TCACTGCTAATGAGgCTGGAGCTGGTCCCCAGCAGTGGTAGGAAGCTTCCAaCAGGCTCA
GGCTGTGGGTGCTTGCAGGGGCACAGTGTGACGGCCACGGGCCTCAGAGCTCTGGTGGGC
T (SEQ ID NO: 292)

| OLIGO | start | len | tm | gc % | any | 3' | seq (SEQ ID NOs: 293, 294) |
|---|---|---|---|---|---|---|---|
| LEFT PRIMER | 2 | 20 | 53.05 | 45.00 | 5.00 | 3.00 | GACAGAAAAGTCTCAGAGCA |
| RIGHT PRIMER | 135 | 18 | 62.10 | 61.11 | 5.00 | 3.00 | CAAGCACCCACAGCCTGA |

SEQUENCE SIZE: 181
INCLUDE0 REGION SIZE: 181

PRODUCT SIZE: 134, PAIR ANY COMPL: 4.00, PAIR 3' COMPL: 3.00
```
  1 TGACAGAAAAGTCTCAGAGCAGTGCCTTCTGAGCTCTTCTACACCAAGCAGGCAGAATGT
    >>>>>>>>>>>>>>>>>>>>

61 TCACTGCTAATGAGgCTGGAGCTGGTCCCCAGCAGTGGTAGGAAGCTTCCAaCAGGCTCA
                                                           <<<

121 GGCTGTGGGTGCTTGCAGGGGCACAGTGTGACGGCCACGGGCCTCAGAGCTCTGGTGGGC
    <<<<<<<<<<<<<<<

181 T
```

102) Whole sequence ::: rs8134902-rs8133874

ACATCTTTCTCAAATAAAGATAACAGCGATGTATTTTCACAAAAGCAAGAGCTTAGAAAG
TACTcCACCCAGGTATCCCTCTTGGAAAAAATaCTTAAGGAAATATGACAAATGGCAAAG
TGATTGTTATGGATGGAATGTTTGTATCCTCCCAAAATTCACATGTTGAGACCCTAATTC
CAATATG (SEQ ID NO: 295)

| OLIGO | start | len | tm | gc % | any | 3' | seq (SEQ ID NOs: 296, 297) |
|---|---|---|---|---|---|---|---|
| LEFT PRIMER | 33 | 20 | 54.84 | 35.00 | 5.00 | 2.00 | ATTTTCACAAAAGCAAGAGC |
| RIGHT PRIMER | 155 | 20 | 54.97 | 40.00 | 3.00 | 0.00 | TTGGGAGGATACAAACATTC |

SEQUENCE SIZE: 187
INCLUDED REGION SIZE: 187

PRODUCT SIZE: 123, PAIR ANY COMPL: 4.00, PAIR 3' COMPL: 0.00
```
  1 ACATCTTTCTCAAATAAAGATAACAGCGATGTATTTTCACAAAAGCAAGAGCTTAGAAAG
                                     >>>>>>>>>>>>>>>>>>>>

61 TACTcCACCCAGGTATCCCTCTTGGAAAAAATaCTTAAGGAAATATGACAAATGGCAAAG
```

TABLE 2-continued

```
121 TGATTGTTATGGATGGAATGTTTGTATCCTCCCAAAATTCACATGTTGAGACCCTAATTC
               <<<<<<<<<<<<<<<<<<

181 CAATATG

103) Whole sequence ::: rs425667-rs382478

AGGGGCATTCTACAAAACACCCAACCGGTCAAGGTCGCTGAGGCCAAGGAGAGATTGGGC
AACCGTCACAAACCAGAGAAGcCGAGGAGAcCTTTCAGCCAACGCCATGTGGGGTCCTGA
GCAGGACCCACCGGAAGTTGGTGCAGCTGCCTAAAGACCGTCCTGGCTGAGAAGAAACAG
(SEQ ID NO: 298)

OLIGO          start len   tm    gc %  any  3'   seq (SEQ ID NOs: 299, 300)

LEFT PRIMER     46    18  55.06 50.00 4.00 2.00 AAGGAGAGATTGGGCAAC
RIGHT PRIMER   178    19  54.85 52.63 3.00 1.00 GTTTCTTCTCAGCCAGGAC
SEQUENCE SIZE: 180
INCLUDED REGION SIZE: 180

PRODUCT SIZE: 133, PAIR ANY COMPL: 4.00, PAIR 3' COMPL: 0.00
   1 AGGGGCATTCTACAAAACACCCAACCGGTCAAGGTCGCTGAGGCCAAGGAGAGATTGGGC
                                                  >>>>>>>>>>>>>>>>>>

61 AACCGTCACAAACCAGAGAAGcCGAGGAGAcCTTTCAGCCAACGCCATGTGGGGTCCTGA
     >>>

121 GCAGGACCCACCGGAAGTTGGTGCAGCTGCCTAAAGACCGTCCTGGCTGAGAAGAAACAG
                                        <<<<<<<<<<<<<<<<<<<

104) Whole sequence ::: rs2838650-rs2838651

TGGCCCTGACCTGCCAGAGCTGTTGGCCTCCAGCTGGCGGGTAAAACCCACGGCCTTCTC
AGAACAGGTTTCTCAACACATGAGACAGAACACACCAGACTTCCaAGGGGAACACCTGGA
TGGAGCTGGTTACCCAGATcGTTCAACACCGAGGGGCAGCGGCTTGAGGGTCTTTCCACG
AAGGCTTGGATTAACAAGAGGAGCASRGGTCTCTCCAGGATGGGCCCA
(SEQ ID NO: 301)

OLIGO          start len   tm    gc %  any  3'   seq (SEQ ID NOs: 302, 303)

LEFT PRIMER     79    20  54.89 50.00 4.00 1.00 CATGAGACAGAACACACCAG
RIGHT PRIMER   199    20  54.61 40.00 5.00 3.00 TCTTGTTAATCCAAGCCTTC
SEQUENCE SIZE: 228
INCLUDED REGION SIZE: 228

PRODUCT SIZE: 121, PAIR ANY COMPL: 4.00, PAIR 3' COMPL: 1.00
   1 TGGCCCTGACCTGCCAGAGCTGTTGGCCTCCAGCTGGCGGGTAAAACCCACGGCCTTCTC

61 AGAACAGGTTTCTCAACACATGAGACAGAACACACCAGACTTCCaAGGGGAACACCTGGA
                       >>>>>>>>>>>>>>>>>>>>

121 TGGAGCTGGTTACCCAGATcGTTCAACACCGAGGGGCAGCGGCTTGAGGGTCTTTCCACG
                                                                <

181 AAGGCTTGGATTAACAAGAGGAGCASRGGTCTCTCCAGGATGGGCCCA
        <<<<<<<<<<<<<<<<<<<

105) Whole sequence ::: rs2838654-rs1296489

CCACCCAGTGTCACGTCACGGCCCCGGCACGCCATCCACGGACCCTGGATGGAGCCCAGC
TGCCTCCaGGAGCGCAGTTTAACTACAAAGGAGCCCTGGCTGCCCGCCCCGCCCAGACGC
ACTGACCTGTTGTTCTCTGTGGCTGCTGATGGCCcATCCCCAACCACTGGTGACTCTTCC
CTGGGGCCCCAAGCTCAGCCCCTAACCCCCTGTTGCTGGAAGT (SEQ ID NO: 304)

OLIGO          start len   tm    gc %  any  3'   seq (SEQ ID NOs: 305, 306)

LEFT PRIMER     37    18  62.56 66.67 5.00 2.00 CACGGACCCTGGATGGAG
RIGHT PRIMER   183    18  53.14 55.56 3.00 2.00 CAGGGAAGAGTCACCAGT
SEQUENCE SIZE: 223
INCLUDED REGION SIZE: 223

PRODUCT SIZE: 147, PAIR ANY COMPL: 5.00, PAIR 3' COMPL: 2.00
   1 CCACCCAGTGTCACGTCACGGCCCCGGCACGCCATCCACGGACCCTGGATGGAGCCCAGC
                                           >>>>>>>>>>>>>>>>>>

61 TGCCTCCaGGAGCGCAGTTTAACTACAAAGGAGCCCTGGCTGCCCGCCCCGCCCAGACGC

121 ACTGACCTGTTGTTCTCTGTGGCTGCTGATGGCCcATCCCCAACCACTGGTGACTCTTCC
                                              <<<<<<<<<<<<<<<<<<
```

TABLE 2-continued

```
181 CTGGGGCCCCAAGCTCAGCCCCTAACCCCCTGTTGCTGGAAGT
        <<<
```

106) Whole sequence ::: rs2838659-rs1108261

```
CAGAGGACTGGGCTGCGGGGTCAGGAATGGGCACACTTCCTAACTGCAGGACACTCTAAG
GGCTTTGGTCATGCACACgCAGCCAAGAGAAGGTGTCGCTGaCACACAGCCTTCCAGGAG
CGGACTTGGAGACCTCGCCAAGGACCAGGACTCCCCAGCACTCACACTCCCTTAGGCGCT
GAAGTC (SEQ ID NO: 307)
```

| OLIGO | start | len | tm | gc % | any | 3' | seq (SEQ ID NOs: 308, 309) |
|---|---|---|---|---|---|---|---|
| LEFT PRIMER | 53 | 20 | 55.48 | 45.00 | 4.00 | 2.00 | ACTCTAAGGGCTTTGGTCAT |
| RIGHT PRIMER | 175 | 20 | 56.02 | 55.00 | 3.00 | 1.00 | CTAAGGGAGTGTGAGTGCTG |

SEQUENCE SIZE: 186
INCLUDED REGION SIZE: 186

PRODUCT SIZE: 123, PAIR ANY COMPL: 4.00, PAIR 3' COMPL: 1.00

```
  1 CAGAGGACTGGGCTGCGGGGTCAGGAATGGGCACACTTCCTAACTGCAGGACACTCTAAG
                                                          >>>>>>>

61 GGCTTTGGTCATGCACACgCAGCCAAGAGAAGGTGTCGCTGaCACACAGCCTTCCAGGAG
    >>>>>>>>>>>>>

121 CGGACTTGGAGACCTCGCCAAGGACCAGGACTCCCCAGCACTCACACTCCCTTAGGCGCT
                                              <<<<<<<<<<<<<<<<<<<<

181 GAAGTC
```

107) Whole sequence ::: rs585587-rs585601

```
GAAGAGGACAACACGGGGCTGTCTGCAGAGCACCTGCCACGCGCCAGGCTCTGTGTCCAC
AAGCACGGCGGCTGCTCCCACATGACaGAGCTCGTGcGGCAGCTCCAGGACTGTCTGGTG
CCAGAGCCCCAGCTCTCCGCCAGCCCCAGGCCACTGTGCGAGGCCCTCAGTGAAGAGGGG
GCCGT (SEQ ID NO: 310)
```

| OLIGO | start | len | tm | gc % | any | 3' | seq (SEQ ID NOs: 311, 312) |
|---|---|---|---|---|---|---|---|
| LEFT PRIMER | 42 | 18 | 64.78 | 66.67 | 5.00 | 2.00 | CGCCAGGCTCTGTGTCCA |
| RIGHT PRIMER | 183 | 18 | 60.76 | 66.67 | 5.00 | 3.00 | GGCCCCCTCTTCACTGAG |

SEQUENCE SIZE: 185
INCLUDED REGION SIZE: 185

PRODUCT SIZE: 142, PAIR ANY COMPL: 5.00, PAIR 3' COMPL: 3.00

```
  1 GAAGAGGACAACACGGGGCTGTCTGCAGAGCACCTGCCACGCGCCAGGCTCTGTGTCCAC
                                               >>>>>>>>>>>>>>>>>>

61 AAGCACGGCGGCTGCTCCCACATGACaGAGCTCGTGcGGCAGCTCCAGGACTGTCTGGTG

121 CCAGAGCCCCAGCTCTCCGCCAGCCCCAGGCCACTGTGCGAGGCCCTCAGTGAAGAGGGG
                                                    <<<<<<<<<<<<<

181 GCCGT
        <<<
```

108) Whole sequence ::: rs9981033-rs4818998

```
TCTAAATAATGTTAATGATCAAATTTAGTCAGATCTCAATCTTCATATGTTAGTTGCCTT
CTTAaTAAATATTCTGTTTTCTTTATCGTTCTTTATTTGTATCTCcACCTTCATTTCTGA
TTAAATTAAGAAGTTTTGTCTCTTCCATTTAATAATTAATGTATTTAATAACC
(SEQ ID NO: 313)
```

| OLIGO | start | len | tm | gc % | any | 3' | seq (SEQ ID NOs: 314, 315) |
|---|---|---|---|---|---|---|---|
| LEFT PRIMER | 24 | 22 | 51.86 | 31.82 | 6.00 | 2.00 | TTTAGTCAGATCTCAATCTTCA |
| RIGHT PRIMER | 149 | 22 | 54.02 | 31.82 | 4.00 | 3.00 | AATGGAAGAGACAAAACTTCTT |

SEQUENCE SIZE: 173
INCLUDED REGION SIZE: 173

PRODUCT SIZE: 126, PAIR ANY COMPL: 5.00, PAIR 3' COMPL: 1.00

```
  1 TCTAAATAATGTTAATGATCAAATTTAGTCAGATCTCAATCTTCATATGTTAGTTGCCTT
                            >>>>>>>>>>>>>>>>>>>>>>

61 CTTAaTAAATATTCTGTTTTCTTTATCGTTCTTTATTTGTATCTCcACCTTCATTTCTGA

121 TTAAATTAAGAAGTTTTGTCTCTTCCATTTAATAATTAATGTATTTAATAACC
         <<<<<<<<<<<<<<<<<<<<<<
```

TABLE 2-continued

109) Whole sequence ::: rs2838802-rs2838803

CACACTCCACACTGGCCCCACGCGGGTGGCGAAGGACTCAGCCAGAGCCTGGCAGGATCC
TGGGGTGTCTaTTTCCAAGGAATGTTCTGGAAGAAACATACACACATACTTGTTTGCCAG
ATTTACCTGTGTGGTcTTCCAGATGAGAAGCAGCCTGTGTCACTCCATAAGGGAGAGTGC
GTGCAGCATTGAGA (SEQ ID NO: 316)

OLIGO          start len   tm    gc %   any   3'   seq (SEQ ID NOs: 317, 318)

LEFT PRIMER     31   18  55.96  61.11  5.00  3.00 GAAGGACTCAGCCAGAGC
RIGHT PRIMER   177   20  55.20  50.00  7.00  3.00 CTCTCCCTTATGGAGTGACA
SEQUENCE SIZE: 194
INCLUDED REGION SIZE: 194

PRODUCT SIZE: 147, PAIR ANY COMPL: 4.00, PAIR 3' COMPL: 0.00
  1 CACACTCCACACTGGCCCCACGCGGGTGGCGAAGGACTCAGCCAGAGCCTGGCAGGATCC
                                  >>>>>>>>>>>>>>>>>>

61 TGGGGTGTCTaTTTCCAAGGAATGTTCTGGAAGAAACATACACACATACTTGTTTGCCAG

121 ATTTACCTGTGTGGTcTTCCAGATGAGAAGCAGCCTGTGTCACTCCATAAGGGAGAGTGC
                                           <<<<<<<<<<<<<<<<<<<<

181 GTGCAGCATTGAGA

110) Whole sequence ::: rs2183596-rs2150452

AAGAAACTCCCAAGGAACGCATTGTCCCAAGTTGCTGCACCAGTCAGTGTACATTCCCAC
AAaCAGTGCATGAGAGTTCCTGTTGCTTGTGAAATAAATGGTCAGCATTCAGTGTTGTCA
GCTTTTAAAATTTTCTCCTTTCTAGTGGGCATGTAATGGTCTCACATTATAGTTTTAATT
TGCATTTTCCTGGTGACATGTGATACGGAACCTTCCTCCCATGCT (SEQ ID NO: 319)

OLIGO          start len   tm    gc %   any   3'   seq (SEQ ID NOs: 320, 321)

LEFT PRIMER     39   19  50.19  47.37  6.00  2.00 ACCAGTCAGTGTACATTCC
RIGHT PRIMER   190   19  50.12  26.32  4.00  0.00 GGAAAATGCAAATTAAAAC
SEQUENCE SIZE: 225
INCLUDED REGION SIZE: 225

PRODUCT SIZE: 152, PAIR ANY COMPL: 4.00, PAIR 3' COMPL: 1.00
  1 AAGAAACTCCCAAGGAACGCATTGTCCCAAGTTGCTGCACCAGTCAGTGTACATTCCCAC
                                             >>>>>>>>>>>>>>>>>>>

61 AAaCAGTGCATGAGAGTTCCTGTTGCTTGTGAAATAAATGGTCAGCATTCAGTGTTGTCA

121 GCTTTTAAAATTTTCTCCTTTCTAGTGGGCATGTAATGGTcTCACATTATAGTTTTAATT
                                                        <<<<<<<<

181 TGCATTTTCCTGGTGACATGTGATACGGAACCTTCCTCCCATGCT
    <<<<<<<<<

111) Whole sequence ::: rs4599218-rs9978646

GTGCAATTTAATTACAAACGCTTAAATGGGGAGGTCAGGGGCAGAGGGATGATGTCACAA
ACACACCCAcGTGTGCTTGGTGCAAAACAGTAAAACAAACAGCAAGAAGgTCCATGAAGG
AAAGATCGCCTCTGTCAGTGGGAGTAATGAGAGTGGCTGATGGACAGGTG
(SEQ ID NO: 322)

OLIGO          start len   tm    gc %   any   3'   seq (SEQ ID NOs: 323, 324)

LEFT PRIMER     19   20  61.86  55.00  4.00  1.00 CGCTTAAATGGGGAGGTCAG
RIGHT PRIMER   168   20  60.83  60.00  3.00  0.00 CCTGTCCATCAGCCACTCTC
SEQUENCE SIZE: 170
INCLUDED REGION SIZE: 170

PRODUCT SIZE: 150, PAIR ANY COMPL: 5.00, PAIR 3' COMPL: 2.00
  1 GTGCAATTTAATTACAAACGCTTAAATGGGGAGGTCAGGGGCAGAGGGATGATGTCACAA
                        >>>>>>>>>>>>>>>>>>>>

61 ACACACCCAcGTGTGCTTGGTGCAAAACAGTAAAACAAACAGCAAGAAGgTCCATGAAGG

121 AAAGATCGCCTCTGTCAGTGGGAGTAATGAGAGTGGCTGATGGACAGGTG
                                  <<<<<<<<<<<<<<<<<<<<

112) Whole sequence ::: rs11702503-rs3827270

ACGCCAAGCAGGAGATGCCAGACACAGAGTCCATCCTGAGAGAGTCTGTTCCTGTCCAAG
CTCAGAAACACAGGAAGCcACCTGTGCTGTAGCAGCACaCGGAGATGCATCCTTTCTGGT

TABLE 2-continued

```
CCACCCCACGGCCCTCATTGCAGTCAGGGATCCTCTCCCAGAAAGTCCCTGCTGCCAGCC
CCTGCCCTT (SEQ ID NO: 325)

OLIGO          start  len   tm    gc %   any   3'   seq (SEQ ID NOs: 326, 327)

LEFT PRIMER       7    20  62.02  55.00  3.00  0.00 AGCAGGAGATGCCAGACACA
RIGHT PRIMER    125    20  63.37  55.00  5.00  4.00 GGTGGACCAGAAAGGATGCA
SEQUENCE SIZE: 189
INCLUDED REGION SIZE: 189

PRODUCT SIZE: 119, PAIR ANY COMPL: 3.00, PAIR 3' COMPL: 0.00
    1 ACGCCAAGCAGGAGATGCCAGACACAGAGTCCATCCTGAGAGAGTCTGTTCCTGTCCAAG
            >>>>>>>>>>>>>>>>>>>>

61 CTCAGAAACACAGGAAGCcACCTGTGCTGTAGCAGCACaCGGAGATGCATCCTTTCTGGT
                                            <<<<<<<<<<<<<<<<<<<<

121 CCACCCCACGGCCCTCATTGCAGTCAGGGATCCTCTCCCAGAAAGTCCCTGCTGCCAGCC
          <<<<<

181 CCTGCCCTT

113) Whole sequence ::: rs2839084-rs9984302

CATGAGAAAGACTTTGTTCCCATGAGAACAACAAGAGAAACTCAAACAAAATTAAAATTG
TACTTTTCTAAAAGACcGGGGTGGGGGTCGTGGTCAGGCAGCaGCATGAAGAAAGCCTTG
AGAACTGAATTCCAGAAAGAAACAAGCATAGGCAAGAAAGAGAGATGACA
(SEQ ID NO: 328)

OLIGO          start  len   tm    gc %   any   3'   seq (SEQ ID NOs: 329, 330)

LEFT PRIMER      19    22  59.21  40.91  4.00  0.00 CCCATGAGAACAACAAGAGAAA
RIGHT PRIMER    162    20  55.46  45.00  4.00  2.00 CTCTTTCTTGCCTATGCTTG
SEQUENCE SIZE: 170
INCLUDED REGION SIZE: 170

PRODUCT SIZE: 144, PAIR ANY COMPL: 5.00, PAIR 3' COMPL: 3.00
    1 CATGAGAAAGACTTTGTTCCCATGAGAACAACAAGAGAAACTCAAACAAAATTAAAATTG
                          >>>>>>>>>>>>>>>>>>>>>>

61 TACTTTTCTAAAAGACcGGGGTGGGGGTCGTGGTCAGGCAGCaGCATGAAGAAAGCCTTG

121 AGAACTGAATTCCAGAAAGAAACAAGCATAGGCAAGAAAGAGAGATGACA
                           <<<<<<<<<<<<<<<<<<<<

114) Whole sequence ::: rs2249057-rs2249060

AAGATTTAGAACAGCTGAAGCAGCGAGAAAAAACCCAGCATGAGTCaGAACTGGAGCAAC
TGAGGATTTATTTTGAAAAGAAGTTAAGGGATGCTGAGAAAACTTACCAAGAAGACCTAA
cCCTGTTACAGCAGAGGCTGCAGGGGGCGAGGGAAGATGCTCTTCTG
(SEQ ID NO: 331)

OLIGO          start  len   tm    gc %   any   3'   seq (SEQ ID NOs: 332, 333)

LEFT PRIMER      12    21  63.07  47.62  6.00  0.00 CAGCTGAAGCAGCGAGAAAAA
RIGHT PRIMER    146    19  66.33  68.42  6.00  3.00 CCCCTGCAGCCTCTGCTGT
SEQUENCE SIZE: 167
INCLUDED REGION SIZE: 167

PRODUCT SIZE: 135, PAIR ANY COMPL: 7.00, PAIR 3' COMPL: 1.00
    1 AAGATTTAGAACAGCTGAAGCAGCGAGAAAAAACCCAGCATGAGTCaGAACTGGAGCAAC
                  >>>>>>>>>>>>>>>>>>>>>

61 TGAGGATTTATTTTGAAAAGAAGTTAAGGGATGCTGAGAAAACTTACCAAGAAGACCTAA 121 cCCTGTTACAGCAGAGGCTGCAGGGGGCGAGGGAAGATGCTCTTCTG
                 <<<<<<<<<<<<<<<<<<<

115) Whole sequence ::: rs2839226-rs2839227

GGGAAACTGACTTGGCTTTTGCAAGGGTCATTGCTTCCTGATGCATGTTTAACTGTCCTG
TGTTCACTTTGTTGCcGCAGGTTTTTAGAGGAACGTAAAGAGATCaCCGAGAAATTCAGT
GCGGAACAAGATGCCTTCCTGCAGGAGGCCCAGGAGCAGCATGCCCGTGAGCTG
(SEQ ID NO: 334)

OLIGO          start  len   tm    gc %   any   3'   seq (SEQ ID NOs: 335, 336)

LEFT PRIMER       1    22  64.29  50.00  3.00  2.00 GGGAAACTGACTTGGCTTTTGC
RIGHT PRIMER    135    20  64.63  55.00  3.00  2.00 GGCATCTTGTTCCGCACTGA
```

TABLE 2-continued

```
SEQUENCE SIZE: 174
INCLUDED REGION SIZE: 174

PRODUCT SIZE: 135, PAIR ANY COMPL: 4.00, PAIR 3' COMPL: 0.00
   1 GGGAAACTGACTTGGCTTTTGCAAGGGTCATTGCTTCCTGATGCATGTTTAACTGTCCTG
     >>>>>>>>>>>>>>>>>>>>

61 TGTTCACTTTGTTGCcGCAGGTTTTTAGAGGAACGTAAAGAGATCaCCGAGAAATTCAGT
                                                           <<<<<

121 GCGGAACAAGATGCCTTCCTGCAGGAGGCCCAGGAGCAGCATGCCCGTGAGCTG
     <<<<<<<<<<<<<<<

116) Whole sequence ::: rs10854482-rs2839261
```

CCCTGCACACTGACCTGCATGCCCTCGTCACCTGCACTCTGCATGCTCACCATCTGACGG
ACTCCTGCGAcGGGCATGGGAAGGTCGCCGCCGCCGGCAGCCtTGCGAGCACTTTGGATG
TGTGCACCCGGCATGCCAGGCCCGAGTCAACAGACTGGCCGACCTTGGCGTCCTG
(SEQ ID NO: 337)

```
OLIGO          start len   tm   gc %  any  3'  seq (SEQ ID NOs: 338, 339)

LEFT PRIMER      21   20 65.22 65.00 4.00 0.00 GCCCTCGTCACCTGCACTCT
RIGHT PRIMER    168   20 64.77 60.00 5.00 1.00 CCAAGGTCGGCCAGTCTGTT
SEQUENCE SIZE: 175
INCLUDED REGION SIZE: 175

PRODUCT SIZE: 148, PAIR ANY COMPL: 4.00, PAIR 3' COMPL: 0.00
   1 CCCTGCACACTGACCTGCATGCCCTCGTCACCTGCACTCTGCATGCTCACCATCTGACGG
                           >>>>>>>>>>>>>>>>>>>>

61 ACTCCTGCGAcGGGCATGGGAAGGTCGCCGCCGCCGGCAGCCtTGCGAGCACTTTGGATG

121 TGTGCACCCGGCATGCCAGGCCCGAGTCAACAGACTGGCCGACCTTGGCGTCCTG
                             <<<<<<<<<<<<<<<<<<<<

117) Whole sequence ::: rs2032111-rs718496
```

TTTATTGCTGAGTGGTATTCCATTTTATGGGTCCATTATAGTTTATTTGTCCAGACACTT
CATGGAAaGACATCAGTGTTTCCtGTTTTTCAATCATAAATTGATGTTTAATTTTAAAAT
TTTGGAATTGTAGAAGAAATGCAATTCTTTTTTCC (SEQ ID NO: 340)

```
OLIGO          start len   tm   gc %  any  3'  seq (SEQ ID NOs: 341, 342)

LEFT PRIMER      28   22 53.65 31.82 4.00 3.00 TGGGTCCATTATAGTTTATTTG
RIGHT PRIMER    143   22 57.46 31.82 4.00 2.00 TGCATTTCTTCTACAATTCCAA
SEQUENCE SIZE: 155
INCLUDED REGION SIZE: 155

PRODUCT SIZE: 116, PAIR ANY COMPL: 5.00, PAIR 3' COMPL: 3.00
   1 TTTATTGCTGAGTGGTATTCCATTTTATGGGTCCATTATAGTTTATTTGTCCAGACACTT
                                 >>>>>>>>>>>>>>>>>>>>>>

61 CATGGAAaGACATCAGTGTTTCCtGTTTTTCAATCATAAATTGATGTTTAATTTTAAAAT

121 TTTGGAATTGTAGAAGAAATGCAATTCTTTTTTCC
     <<<<<<<<<<<<<<<<<<<<<<

118) Whole sequence ::: rs2070434-rs2070435
```

CTTTGGTGCAGAATCATGCTGCAGGCAAGGTGGGCCCACCTCCCTGGAATTTCATCCCCC
cCGTCAGTTAAACCCATGGTGGTTTTATTTTCTAGGCCACCTGATCTGGGAGGACCACCT
CCAAGAAAAGCAGTCCTaTCGATGAACGGTCTAAGTTATGGTGTTATCAGAGTGGATACT
GAAGAAAAGTTGTCAGTCCTTACTGTTC (SEQ ID NO: 343)

```
OLIGO          start len   tm   gc %  any  3'  seq (SEQ ID NOs: 344, 345)

LEFT PRIMER      33   20 66.57 60.00 4.00 3.00 GGCCCACCTCCCTGGAATTT
RIGHT PRIMER    176   22 54.26 40.91 4.00 0.00 TCCACTCTGATAACACCATAAC
SEQUENCE SIZE: 208
INCLUDED REGION SIZE: 208

PRODUCT SIZE: 144, PAIR ANY COMPL: 4.00, PAIR 3' COMPL: 1.00
   1 CTTTGGTGCAGAATCATGCTGCAGGCAAGGTGGGCCCACCTCCCTGGAATTTCATCCCCC
                                       >>>>>>>>>>>>>>>>>>>>
```

TABLE 2-continued

```
 61 cCGTCAGTTAAACCCATGGTGGTTTTATTTTCTAGGCCACCTGATCTGGGAGGACCACCT

121 CCAAGAAAAGCAGTCCTaTCGATGAACGGTCTAAGTTATGGTGTTATCAGAGTGGATACT
                                   <<<<<<<<<<<<<<<<<<<<

181 GAAGAAAAGTTGTCAGTCCTTACTGTTC
```

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for determining whether a fetus has at least one chromosomal abnormality, said method comprising:
   (a) detecting at least three alleles of at least one tandem single nucleotide polymorphism (SNP) in a maternal sample, wherein each of said at least one tandem SNP is a pair of SNPs and each of said at least three alleles is a different haplotype of each of said at least one tandem SNP, and wherein one of said alleles is not present in the maternal genome; and
   (b) comparing said at least three alleles, wherein said comparing comprises comparing relative copy number of each of said at least three alleles to relative copy number of each other, wherein said comparing identifies said at least one chromosomal abnormality, thereby determining whether the fetus has at least one chromosomal abnormality.

2. A method according to claim 1, wherein said maternal genome is heterozygous for said tandem single nucleotide polymorphism.

3. A method according to claim 1, wherein said maternal sample is obtained from a member selected from: maternal blood, maternal plasma and maternal serum.

4. A method according to claim 1, wherein said detecting step (a) comprises detecting at least three alleles of multiple tandem SNPs.

5. A method according to claim 4, wherein said detecting step (a) comprises detecting at least three alleles of at least 96 tandem SNPs.

6. A method according to claim 4, wherein at least one of said multiple tandem SNPs is located on the p arm or the q arm of chromosome 21.

7. A method according to claim 6, wherein at least one of said multiple tandem SNPs is located on the p arm of chromosome 21 and at least one of said multiple tandem SNPs is located on the q arm of chromosome 21.

8. A method according to claim 1, wherein said at least one chromosomal abnormality is chromosomal aneuploidy.

9. A method according to claim 8, wherein said chromosomal abnormality is a member selected from trisomy 13, trisomy 18, and trisomy 21.

10. A method according to claim 1, wherein said at least one chromosomal abnormality is a member selected from: a deletion mutation, an insertion mutation, a copy number polymorphism, a copy number variant, chromosome 22q11 deletion syndrome, 11q deletion syndrome on chromosome 11, and 8p deletion syndrome on chromosome 8.

11. A method for determining whether a fetus has at least one chromosomal abnormality, said method comprising:
   (a) detecting at least a first haplotype, a second haplotype and a third haplotype of at least one tandem SNP in a sample comprising both maternal DNA and fetal DNA, wherein said maternal DNA is heterozygous for each of said at least one tandem SNP and wherein one of said first, second and third haplotypes detected in said sample is a paternal haplotype; and
   (b) comparing said alleles haplotypes detected in said sample, wherein said comparing comprises comparing copy numbers of said at least first, second and third haplotypes to each other,
   wherein said comparing identifies said at least one chromosomal abnormality, thereby determining whether the fetus has at least one chromosomal abnormality.

12. A method according to claim 11, wherein said comparing step (b) comprises comparing a first signal indicative of the number of copies of said first haplotype, a second signal indicative of the number of copies of said second haplotype, and a third signal indicative of the number of copies of said third haplotype, and wherein the ratio of said first, second and third signals indicates whether said fetus has at least one chromosomal abnormality.

13. A method according to claim 12, wherein the first, second and third haplotypes are detected using constant denaturant capillary electrophoresis (CDCE) and a CDCE electropherogram output is generated comprising a first, second and third peak indicative of the first, second and third signals, respectively.

14. A method according to claim 11, wherein said paternal allele is not present in said maternal DNA.

15. A method according to claim 11, wherein said at least one chromosomal abnormality is chromosomal aneuploidy.

16. A method according to claim 11, wherein said chromosomal abnormality is a member selected from trisomy 13, trisomy 18, and trisomy 21.

17. A method according to claim 11, wherein said sample is obtained from a member selected from: maternal blood, maternal plasma and maternal serum.

18. A method according to claim 11, wherein said at least one chromosomal abnormality is a member selected from: a deletion mutation, an insertion mutation, a copy number polymorphism, a copy number variant, chromosome 22q11 deletion syndrome, 11q deletion syndrome on chromosome 11, and 8p deletion syndrome on chromosome 8.

19. A method according to claim 11, wherein said detecting step (a) comprises detecting first, second and third haplotypes for each of multiple tandem SNPs.

20. A method according to claim 19, wherein said detecting step (a) comprises detecting first, second and third haplotypes for each of at least 96 tandem SNPs.

21. A method according to claim 3, wherein said maternal sample is maternal blood.

22. A method according to claim 3, wherein said maternal sample is maternal plasma.

23. A method according to claim 3, wherein said maternal sample is maternal serum.

24. A method according to claim 9, wherein said chromosomal abnormality is trisomy 13.

25. A method according to claim 9, wherein said chromosomal abnormality is trisomy 18.

26. A method according to claim 9, wherein said chromosomal abnormality is trisomy 21.

27. A method according to claim 10, wherein said at least one chromosomal abnormality is a deletion mutation.

28. A method according to claim 10, wherein said at least one chromosomal abnormality is an insertion mutation.

29. A method according to claim 10, wherein said at least one chromosomal abnormality is a copy number polymorphism.

30. A method according to claim 10, wherein said at least one chromosomal abnormality is a copy number variant.

31. A method according to claim 10, wherein said at least one chromosomal abnormality is chromosome 22q11 deletion syndrome.

32. A method according to claim 10, wherein said at least one chromosomal abnormality is 11q deletion syndrome on chromosome 11.

33. A method according to claim 10, wherein said at least one chromosomal abnormality is 8p deletion syndrome on chromosome 8.

34. A method according to claim 16, wherein said chromosomal abnormality is trisomy 13.

35. A method according to claim 16, wherein said chromosomal abnormality is trisomy 18.

36. A method according to claim 16, wherein said chromosomal abnormality is trisomy 21.

37. A method according to claim 17, wherein said maternal sample is maternal blood.

38. A method according to claim 17, wherein said maternal sample is maternal plasma.

39. A method according to claim 17, wherein said maternal sample is maternal serum.

40. A method according to claim 18, wherein said at least one chromosomal abnormality is a deletion mutation.

41. A method according to claim 18, wherein said at least one chromosomal abnormality is an insertion mutation.

42. A method according to claim 18, wherein said at least one chromosomal abnormality is a copy number polymorphism.

43. A method according to claim 18, wherein said at least one chromosomal abnormality is a copy number variant.

44. A method according to claim 18, wherein said at least one chromosomal abnormality is chromosome 22q11 deletion syndrome.

45. A method according to claim 18, wherein said at least one chromosomal abnormality is 11q deletion syndrome on chromosome 11.

46. A method according to claim 18, wherein said at least one chromosomal abnormality is 8p deletion syndrome on chromosome 8.

* * * * *

SEQUENCE LISTING

```
<160> NUMBER OF SEQ ID NOS: 357

<210> SEQ ID NO 1
<211> LENGTH: 127
<212> TYPE: DNA
<213> ORGANISM: Homo sapiens

<400> SEQUENCE: 1
aacaaatctt catcttggaa tagcctgtga gaatgcctaa tcatctacga atgttacttt      60
ggcaccatct actggacaga ttaaataaca accaactcac tgtggattag acctacttct    120
atttcag                                                              127

<210> SEQ ID NO 2
<211> LENGTH: 20
<212> TYPE: DNA
<213> ORGANISM: Homo sapiens

<400> SEQUENCE: 2
atagcctgtg agaatgccta                                                 20

<210> SEQ ID NO 3
<211> LENGTH: 20
<212> TYPE: DNA
<213> ORGANISM: Homo sapiens

<400> SEQUENCE: 3
atccacagtg agttggttgt                                                 20
```

```
<210> SEQ ID NO 4
<211> LENGTH: 84
<212> TYPE: DNA
<213> ORGANISM: Homo sapiens

<400> SEQUENCE: 4
ttcctggaaa acaaaagtat ttctttcata gcccagctag catgataaat cagcgagtca      60
gaattctagc tttgttgtaa ggtt                                             84

<210> SEQ ID NO 5
<211> LENGTH: 20
<212> TYPE: DNA
<213> ORGANISM: Homo sapiens

<400> SEQUENCE: 5
tcctggaaaa caaaagtatt                                                  20

<210> SEQ ID NO 6
<211> LENGTH: 21
<212> TYPE: DNA
<213> ORGANISM: Homo sapiens

<400> SEQUENCE: 6
aaccttacaa caaagctaga a                                                21

<210> SEQ ID NO 7
<211> LENGTH: 71
<212> TYPE: DNA
<213> ORGANISM: Homo sapiens

<400> SEQUENCE: 7
cactaagcct tggggatcca gctgcttaag gactaagacc gtatctagct cctttagta       60 tttccacagc a                                                           71

<210> SEQ ID NO 8
<211> LENGTH: 20
<212> TYPE: DNA
<213> ORGANISM: Homo sapiens

<400> SEQUENCE: 8
actaagcctt ggggatccag                                                  20

<210> SEQ ID NO 9
<211> LENGTH: 21
<212> TYPE: DNA
<213> ORGANISM: Homo sapiens

<400> SEQUENCE: 9
tgctgtggaa atactaaaag g                                                21

<210> SEQ ID NO 10
<211> LENGTH: 155
<212> TYPE: DNA
<213> ORGANISM: Homo sapiens

<400> SEQUENCE: 10
tcctccagag gtaatcctgt gatcagcact aacaccacat accagccctt tcatcagctt      60
gttggagaag catctttact tcccgccaag cagtgaccta gataccatct cacaccagtt     120
agaatcagga tcattaaaaa gtcaagaaaa aacag                                155
```

```
<210> SEQ ID NO 11
<211> LENGTH: 20
<212> TYPE: DNA
<213> ORGANISM: Homo sapiens

<400> SEQUENCE: 11
ctccagaggt aatcctgtga                                                   20

<210> SEQ ID NO 12
<211> LENGTH: 21
<212> TYPE: DNA
<213> ORGANISM: Homo sapiens

<400> SEQUENCE: 12
tggtgtgaga tggtatctag g                                                 21

<210> SEQ ID NO 13
<211> LENGTH: 146
<212> TYPE: DNA
<213> ORGANISM: Homo sapiens

<400> SEQUENCE: 13
tccaagtata atccatgaat cttgtttaaa tatagatcaa ataaaccact ataccaaaaa       60
catcaaaaga caactgggta aattttttaa atgactagct atttgatgtt aaggaagtaa      120
tgttactctc ttatatacaa tttgaa                                           146

<210> SEQ ID NO 14
<211> LENGTH: 22
<212> TYPE: DNA
<213> ORGANISM: Homo sapiens

<400> SEQUENCE: 14
gtataatcca tgaatcttgt tt                                                22

<210> SEQ ID NO 15
<211> LENGTH: 22
<212> TYPE: DNA
<213> ORGANISM: Homo sapiens

<400> SEQUENCE: 15
ttcaaattgt atataagaga gt                                                22

<210> SEQ ID NO 16
<211> LENGTH: 132
<212> TYPE: DNA
<213> ORGANISM: Homo sapiens

<400> SEQUENCE: 16
atggaaccga aacttcaagt agtttcatac gtatcacatt gacagttttc tctaagtttt       60
ctggtcttat gactcgttgt ttcattatta aaactgtgcc agtgtatgca tagggcttag      120 aaattttta at                                                           132

<210> SEQ ID NO 17
<211> LENGTH: 18
<212> TYPE: DNA
<213> ORGANISM: Homo sapiens

<400> SEQUENCE: 17
atggaaccga aacttcaa                                                     18
```

```
<210> SEQ ID NO 18
<211> LENGTH: 22
<212> TYPE: DNA
<213> ORGANISM: Homo sapiens

<400> SEQUENCE: 18
ttaataatga aacaacgagt ca                                         22

<210> SEQ ID NO 19
<211> LENGTH: 157
<212> TYPE: DNA
<213> ORGANISM: Homo sapiens

<400> SEQUENCE: 19
acaggatcct tcctgaagac accaccttgg ggagggtgaa ggataaagaa tttgatcaga    60
aatcaagggt ggtgagatac atgttaagga tgaataaact ggccttttag gattcttgct   120
aaaattagac aatgcagagg caaccacaga gtccaag                            157

<210> SEQ ID NO 20
<211> LENGTH: 19
<212> TYPE: DNA
<213> ORGANISM: Homo sapiens

<400> SEQUENCE: 20
ttcctgaaga caccacctt                                              19

<210> SEQ ID NO 21
<211> LENGTH: 18
<212> TYPE: DNA
<213> ORGANISM: Homo sapiens

<400> SEQUENCE: 21
cttggactct gtggttgc                                               18

<210> SEQ ID NO 22
<211> LENGTH: 173
<212> TYPE: DNA
<213> ORGANISM: Homo sapiens

<400> SEQUENCE: 22
aatttccatt aaatcttgtt cgttgcttta ctgaggcact gaagttacca atgttccact    60
ggttgacctg cggggctatc tctaggttat gttactccag aaaatgaatt gtgtataaaa   120
gaggccttgg aggaaggcgt tttattcaca tcagttgttt tgcacattgc tta          173

<210> SEQ ID NO 23
<211> LENGTH: 20
<212> TYPE: DNA
<213> ORGANISM: Homo sapiens

<400> SEQUENCE: 23
actgaggcac tgaagttacc                                             20

<210> SEQ ID NO 24
<211> LENGTH: 20
<212> TYPE: DNA
<213> ORGANISM: Homo sapiens

<400> SEQUENCE: 24
taagcaatgt gcaaaacaac                                             20

<210> SEQ ID NO 25
```

```
<211> LENGTH: 191
<212> TYPE: DNA
<213> ORGANISM: Homo sapiens

<400> SEQUENCE: 25
tcggtttcag caggaaagtt attttaata acttccctgt atttcttggt ttcagttatt     60
aattaactca ttaatgctaa actttgtgat cctaggttaa aaacatatt caagatagct    120 tcagaatgtt tggtatacaa gtaggtctgg ctaaatataa gtgttagctt tctcaagcat    180
ctaaatgctg g                                                         191

<210> SEQ ID NO 26
<211> LENGTH: 20
<212> TYPE: DNA
<213> ORGANISM: Homo sapiens

<400> SEQUENCE: 26
gcaggaaagt tattttaat                                                  20

<210> SEQ ID NO 27
<211> LENGTH: 21
<212> TYPE: DNA
<213> ORGANISM: Homo sapiens

<400> SEQUENCE: 27
tgcttgagaa agctaacact t                                               21

<210> SEQ ID NO 28
<211> LENGTH: 166
<212> TYPE: DNA
<213> ORGANISM: Homo sapiens

<400> SEQUENCE: 28
aagttatttt taataacttc cctgtatttc ttggtttcag ttattaatta actcattaat     60
gctaaacttt gtgatcctag gttaaaaaac atattcaaga tagcttcaga atgtttggta    120
tacaagtagg tctggctaaa tataagtgtt agctttctca agcatc                   166

<210> SEQ ID NO 29
<211> LENGTH: 20
<212> TYPE: DNA
<213> ORGANISM: Homo sapiens

<400> SEQUENCE: 29 attttaata acttccctgt                                                  20

<210> SEQ ID NO 30
<211> LENGTH: 20
<212> TYPE: DNA
<213> ORGANISM: Homo sapiens

<400> SEQUENCE: 30
cacttatatt tagccagacc                                                 20

<210> SEQ ID NO 31
<211> LENGTH: 152
<212> TYPE: DNA
<213> ORGANISM: Homo sapiens

<400> SEQUENCE: 31
attcattgtg tagaaagtgc ctgactcagt gtttggaaat tgtctgactt ttcctcatat     60
atagtgtggt ttcatgttat tgtatataag aactgacatg aactctgttt acaataatct    120
```

-continued cccagtgcca taaagaccat aataataat at                                      152

<210> SEQ ID NO 32
<211> LENGTH: 20
<212> TYPE: DNA
<213> ORGANISM: Homo sapiens

<400> SEQUENCE: 32
cagtgtttgg aaattgtctg                                                    20

<210> SEQ ID NO 33
<211> LENGTH: 20
<212> TYPE: DNA
<213> ORGANISM: Homo sapiens

<400> SEQUENCE: 33
ggcactggga gattattgta                                                    20

<210> SEQ ID NO 34
<211> LENGTH: 163
<212> TYPE: DNA
<213> ORGANISM: Homo sapiens

<400> SEQUENCE: 34
cactgggtcc tgttgttaag tacacataat accacacagg agaaaatcag gctaattgta        60
aatgggcaac ctacttaatt gtttcattaa aaagcataca gattacattt acactatagc       120
tagtcttgtt tgtttttta ttttgcaaaa gtaattacgg ccc                          163

<210> SEQ ID NO 35
<211> LENGTH: 20
<212> TYPE: DNA
<213> ORGANISM: Homo sapiens

<400> SEQUENCE: 35
tcctgttgtt aagtacacat                                                    20

<210> SEQ ID NO 36
<211> LENGTH: 18
<212> TYPE: DNA
<213> ORGANISM: Homo sapiens

<400> SEQUENCE: 36
gggccgtaat tacttttg                                                      18

<210> SEQ ID NO 37
<211> LENGTH: 108
<212> TYPE: DNA
<213> ORGANISM: Homo sapiens

<400> SEQUENCE: 37
ctactcagta ggcactttgt gtctagaaac ttctgtgtca acggttttcc ctctctctgg        60
aattcatcag gacagaagtg attggtgtgg tggaagaggg ttgtgsta                    108

<210> SEQ ID NO 38
<211> LENGTH: 21
<212> TYPE: DNA
<213> ORGANISM: Homo sapiens

<400> SEQUENCE: 38
actcagtagg cactttgtgt c                                                  21

```
<210> SEQ ID NO 39
<211> LENGTH: 18
<212> TYPE: DNA
<213> ORGANISM: Homo sapiens

<400> SEQUENCE: 39
tcttccacca caccaatc                                                   18

<210> SEQ ID NO 40
<211> LENGTH: 144
<212> TYPE: DNA
<213> ORGANISM: Homo sapiens

<400> SEQUENCE: 40
tggcttttca aggtaaaat ttactaagtg tattaatatt ttaccaattt ccagccagga      60
gagtatgaat gttgcattat tacattgctt tgaaacaaag cattagtctt aattcagaag    120
tttaaattca gatgttaacg ttgc                                           144

<210> SEQ ID NO 41
<211> LENGTH: 19
<212> TYPE: DNA
<213> ORGANISM: Homo sapiens

<400> SEQUENCE: 41
tggcttttca aggtaaaa                                                   19

<210> SEQ ID NO 42
<211> LENGTH: 21
<212> TYPE: DNA
<213> ORGANISM: Homo sapiens

<400> SEQUENCE: 42
gcaacgttaa catctgaatt t                                               21

<210> SEQ ID NO 43
<211> LENGTH: 110
<212> TYPE: DNA
<213> ORGANISM: Homo sapiens

<400> SEQUENCE: 43
taagtattga agaaaggaga atttaaatta cttcatatac ctgataaagg aaaacatata     60
caaggcaaat aaacatctta gatcatgaca tataaaataa tagattatta               110

<210> SEQ ID NO 44
<211> LENGTH: 20
<212> TYPE: DNA
<213> ORGANISM: Homo sapiens

<400> SEQUENCE: 44
ttgaagaaag gagaatttaa                                                 20

<210> SEQ ID NO 45
<211> LENGTH: 22
<212> TYPE: DNA
<213> ORGANISM: Homo sapiens

<400> SEQUENCE: 45
attttatatg tcatgatcta ag                                              22

<210> SEQ ID NO 46
<211> LENGTH: 165
```

```
<212> TYPE: DNA
<213> ORGANISM: Homo sapiens

<400> SEQUENCE: 46
tgcagagatt acaggtgtga gccaccgtgc ccagcctcat aaccgtttca actactttt      60 cacttgacaa gcagatgtga agttaacaaa gtcacccata tttgaaataa agatagtata   120
ttcctggggt aggcagaggc agttgaggat catgaaataa ctatg                    165

<210> SEQ ID NO 47
<211> LENGTH: 19
<212> TYPE: DNA
<213> ORGANISM: Homo sapiens

<400> SEQUENCE: 47
agagattaca ggtgtgagc                                                  19

<210> SEQ ID NO 48
<211> LENGTH: 19
<212> TYPE: DNA
<213> ORGANISM: Homo sapiens

<400> SEQUENCE: 48
atgatcctca actgcctct                                                  19

<210> SEQ ID NO 49
<211> LENGTH: 178
<212> TYPE: DNA
<213> ORGANISM: Homo sapiens

<400> SEQUENCE: 49
tgcaatgaaa ctcaaaagag aaaagttaac aggtgcaaaa ggtagtttta ttataaaagg     60
agggtaggca acaagaatat gtttaatttt tcttcctttt catgagtaag gacaagagtg   120
tcatatatgt gaatatttt atttaattt aagtagaaat ctgtttttaa aatatggg       178

<210> SEQ ID NO 50
<211> LENGTH: 20
<212> TYPE: DNA
<213> ORGANISM: Homo sapiens

<400> SEQUENCE: 50
tgaaactcaa aagagaaaag                                                 20

<210> SEQ ID NO 51
<211> LENGTH: 20
<212> TYPE: DNA
<213> ORGANISM: Homo sapiens

<400> SEQUENCE: 51
acagatttct acttaaaatt                                                 20

<210> SEQ ID NO 52
<211> LENGTH: 102
<212> TYPE: DNA
<213> ORGANISM: Homo sapiens

<400> SEQUENCE: 52
ccaccattca tcaaaacttt gatactggac tcaattgtga atttgacttg aaatttgata    60
atgcttttgt tttactgttc tgctcagcaa aatagtacat gt                      102

<210> SEQ ID NO 53
```

```
<211> LENGTH: 20
<212> TYPE: DNA
<213> ORGANISM: Homo sapiens

<400> SEQUENCE: 53
caaaactttg atactggact                                                 20

<210> SEQ ID NO 54
<211> LENGTH: 19
<212> TYPE: DNA
<213> ORGANISM: Homo sapiens

<400> SEQUENCE: 54
acatgtacta ttttgctga                                                  19

<210> SEQ ID NO 55
<211> LENGTH: 166
<212> TYPE: DNA
<213> ORGANISM: Homo sapiens

<400> SEQUENCE: 55
gcctgcataa agtgaggatg gtgtagtaat tgggtatctc cagttataaa cacaaaaagc     60
atgatagagc tgggactgtg attgcaggaa agcaatagtc actccaaaag gagatcctca   120
tgatatgaat acggaagaaa caatatttcc tgctaatgta gtagcc                   166

<210> SEQ ID NO 56
<211> LENGTH: 20
<212> TYPE: DNA
<213> ORGANISM: Homo sapiens

<400> SEQUENCE: 56
cctgcataaa gtgaggatgg                                                 20

<210> SEQ ID NO 57
<211> LENGTH: 21
<212> TYPE: DNA
<213> ORGANISM: Homo sapiens

<400> SEQUENCE: 57
tgaggatctc cttttggagt g                                               21

<210> SEQ ID NO 58
<211> LENGTH: 154
<212> TYPE: DNA
<213> ORGANISM: Homo sapiens

<400> SEQUENCE: 58 gcaaagggt actctatgta atgaacatga cctggcagta ctgacatctc ctgagggact      60
gttagaagtg cagactcttg tatcttttct caagtctatg aaatctagac ttcattttaa    120
caagatgacc cgatatttac atacacatta aagt                                154

<210> SEQ ID NO 59
<211> LENGTH: 20
<212> TYPE: DNA
<213> ORGANISM: Homo sapiens

<400> SEQUENCE: 59 gcaaagggt actctatgta                                                  20

<210> SEQ ID NO 60
<211> LENGTH: 20
```

```
<212> TYPE: DNA
<213> ORGANISM: Homo sapiens

<400> SEQUENCE: 60
tatcgggtca tcttgttaaa                                                 20

<210> SEQ ID NO 61
<211> LENGTH: 174
<212> TYPE: DNA
<213> ORGANISM: Homo sapiens

<400> SEQUENCE: 61
gtatctaaca aagctctgtc caaaattttg aatttctcgt taaaagcatc atgattatag     60
aacagaggtt acaatcaatt attcagtcac acaatcactc tcatcagtca ttaaggtgcg    120
tacctggtgt tccagttatt cagtgtggta taacaaacta cctggaactt aatg          174

<210> SEQ ID NO 62
<211> LENGTH: 22
<212> TYPE: DNA
<213> ORGANISM: Homo sapiens

<400> SEQUENCE: 62
tctaacaaag ctctgtccaa aa                                              22

<210> SEQ ID NO 63
<211> LENGTH: 21
<212> TYPE: DNA
<213> ORGANISM: Homo sapiens

<400> SEQUENCE: 63
ccacactgaa taactggaac a                                               21

<210> SEQ ID NO 64
<211> LENGTH: 202
<212> TYPE: DNA
<213> ORGANISM: Homo sapiens

<400> SEQUENCE: 64
agagtggtta agtgacttga tcaattcctc aggtggggat tcaagctctt aaagctgtag     60
actatgtcgt ccaaacaaac actgacatga atatgacttc caataggcaa gaaaagaggc    120
ctaggtcgag atactgcaag acatgcaagc aatctagtaa tggcataaaa cctgctatcc    180
gaattggcta aaattatgta tt                                             202

<210> SEQ ID NO 65
<211> LENGTH: 20
<212> TYPE: DNA
<213> ORGANISM: Homo sapiens

<400> SEQUENCE: 65
ggtggggatt caagctctta                                                 20

<210> SEQ ID NO 66
<211> LENGTH: 22
<212> TYPE: DNA
<213> ORGANISM: Homo sapiens

<400> SEQUENCE: 66
ggatagcagg ttttatgcca tt                                              22

<210> SEQ ID NO 67
```

```
<211> LENGTH: 156
<212> TYPE: DNA
<213> ORGANISM: Homo sapiens

<400> SEQUENCE: 67
ttctttctca cacaatgggt tccattccca ctactactcc attcaaattg aagtgccttc      60
aatgattatt aaaaaactct ctttaaaata gctcacgtaa ccttacatcc tttgactgag     120
gctcaactca tgtcaatgct tcagtatcaa cttttc                              156

<210> SEQ ID NO 68
<211> LENGTH: 21
<212> TYPE: DNA
<213> ORGANISM: Homo sapiens

<400> SEQUENCE: 68
aatgggttcc attcccacta c                                               21

<210> SEQ ID NO 69
<211> LENGTH: 20
<212> TYPE: DNA
<213> ORGANISM: Homo sapiens

<400> SEQUENCE: 69
tgagcctcag tcaaaggatg                                                 20

<210> SEQ ID NO 70
<211> LENGTH: 202
<212> TYPE: DNA
<213> ORGANISM: Homo sapiens

<400> SEQUENCE: 70
atttgtaata acatttagta agtatttatt tgaggagttt gaattttgtt cttgtttatc      60
ttgttctctt tcttcgtaga ttagttggtg ttaacatcaa taggataacc ctttctttca     120
gcatatgtga atgaaataaa ccaattattg ccactttcca ggttaaccag aatatacata     180
gatacgagga cagtggactg tt                                              202

<210> SEQ ID NO 71
<211> LENGTH: 22
<212> TYPE: DNA
<213> ORGANISM: Homo sapiens

<400> SEQUENCE: 71
ttgaggagtt tgaattttgt tc                                              22

<210> SEQ ID NO 72
<211> LENGTH: 20
<212> TYPE: DNA
<213> ORGANISM: Homo sapiens

<400> SEQUENCE: 72
aacctggaaa gtggcaataa                                                 20

<210> SEQ ID NO 73
<211> LENGTH: 171
<212> TYPE: DNA
<213> ORGANISM: Homo sapiens

<400> SEQUENCE: 73
tagggcagag agagcaagca agctctctac cttctcatat aagggcacta atcccaccat      60
gaaggcgcca ctgtcatgac ctgattatgt cacaaagacc ccggggcaaa tattaccact     120
```
gtgaggagta cagttttagc atgtgaattt tggaagaaca caaacattta g         171

<210> SEQ ID NO 74
<211> LENGTH: 21
<212> TYPE: DNA
<213> ORGANISM: Homo sapiens

<400> SEQUENCE: 74
gcaagcaagc tctctacctt c                                          21

<210> SEQ ID NO 75
<211> LENGTH: 22
<212> TYPE: DNA
<213> ORGANISM: Homo sapiens

<400> SEQUENCE: 75
tgttcttcca aaattcacat gc                                         22

<210> SEQ ID NO 76
<211> LENGTH: 195
<212> TYPE: DNA
<213> ORGANISM: Homo sapiens

<400> SEQUENCE: 76
attctaattt taaatatcat tgatgtagaa cattctattt cactattcct tcattttatt    60
attatgggaa attatataca gttctccaga tttttaaagc cttgctaaca tgttttaagt   120
cacacaaata ttctcctgtg ggaaaatgac agtaatttag tgtgcaacaa ttatatagaa   180 ctattttca aactt                                                   195

<210> SEQ ID NO 77
<211> LENGTH: 21
<212> TYPE: DNA
<213> ORGANISM: Homo sapiens

<400> SEQUENCE: 77
atttcactat tccttcattt t                                          21

<210> SEQ ID NO 78
<211> LENGTH: 22
<212> TYPE: DNA
<213> ORGANISM: Homo sapiens

<400> SEQUENCE: 78
taattgttgc acactaaatt ac                                         22

<210> SEQ ID NO 79
<211> LENGTH: 138
<212> TYPE: DNA
<213> ORGANISM: Homo sapiens

<400> SEQUENCE: 79
actgtcatgg acttaaacaa ttgtctttga attgtctttt ttcatacttt tatttgcatc    60
tttccactaa aaagatggca caaagtaatc ctagtttaca tttttacca tgtaattcca    120 tattactttt tcctgaaa                                                138

<210> SEQ ID NO 80
<211> LENGTH: 20
<212> TYPE: DNA
<213> ORGANISM: Homo sapiens

```
<400> SEQUENCE: 80
actgtcatgg acttaaacaa                                              20

<210> SEQ ID NO 81
<211> LENGTH: 22
<212> TYPE: DNA
<213> ORGANISM: Homo sapiens

<400> SEQUENCE: 81
ttcaggaaaa agtaatatgg aa                                           22

<210> SEQ ID NO 82
<211> LENGTH: 119
<212> TYPE: DNA
<213> ORGANISM: Homo sapiens

<400> SEQUENCE: 82
aaagaaaaaa aagccacaga aatcagtcct agagaaaacc gatctatgag ctgcctgaaa    60
ataattataa aataactatc ataaaaatgc ccagtgagat ataagaaaac acagacaac    119

<210> SEQ ID NO 83
<211> LENGTH: 21
<212> TYPE: DNA
<213> ORGANISM: Homo sapiens

<400> SEQUENCE: 83
aaaaagccac agaaatcagt c                                            21

<210> SEQ ID NO 84
<211> LENGTH: 22
<212> TYPE: DNA
<213> ORGANISM: Homo sapiens

<400> SEQUENCE: 84
ttcttatatc tcactgggca tt                                           22

<210> SEQ ID NO 85
<211> LENGTH: 143
<212> TYPE: DNA
<213> ORGANISM: Homo sapiens

<400> SEQUENCE: 85
caaggtcaga gaagttatct tggatggtag aagagaagaa aggagaagaa aggataagca    60
gaaaatcaaa aagggcataa aaaaattact ggggaaaata attcttagtc actcaccatt   120
tcttatgttt gtgaaaacag aaa                                          143

<210> SEQ ID NO 86
<211> LENGTH: 22
<212> TYPE: DNA
<213> ORGANISM: Homo sapiens

<400> SEQUENCE: 86
ggatggtaga agagaagaaa gg                                           22

<210> SEQ ID NO 87
<211> LENGTH: 22
<212> TYPE: DNA
<213> ORGANISM: Homo sapiens

<400> SEQUENCE: 87
tcacaaacat aagaaatggt ga                                           22
```

```
<210> SEQ ID NO 88
<211> LENGTH: 136
<212> TYPE: DNA
<213> ORGANISM: Homo sapiens

<400> SEQUENCE: 88
gaccacaatt cacaaatgca aagatgcaga accaacctaa gtggccactg actaatgaga    60
ggataaagaa gatgtggcat atatatatca gggactacta ctcagccatt acaaggaaca   120
aaataatgtc ttttgc                                                   136

<210> SEQ ID NO 89
<211> LENGTH: 20
<212> TYPE: DNA
<213> ORGANISM: Homo sapiens

<400> SEQUENCE: 89
tgcaaagatg cagaaccaac                                                20

<210> SEQ ID NO 90
<211> LENGTH: 22
<212> TYPE: DNA
<213> ORGANISM: Homo sapiens

<400> SEQUENCE: 90
ttttgttcct tgtaatggct ga                                             22

<210> SEQ ID NO 91
<211> LENGTH: 160
<212> TYPE: DNA
<213> ORGANISM: Homo sapiens

<400> SEQUENCE: 91
gaccacaatt cacaaatgca aagatgcaga accaacctaa gtggccactg actaatgaga    60
ggataaagaa gatgtggcat atatacatca gggactactt ctcagccatt acaaggaaca   120
aaataatgtc ttttgcaaca acttggatag agctggaggc                         160

<210> SEQ ID NO 92
<211> LENGTH: 20
<212> TYPE: DNA
<213> ORGANISM: Homo sapiens

<400> SEQUENCE: 92
tgcaaagatg cagaaccaac                                                20

<210> SEQ ID NO 93
<211> LENGTH: 21
<212> TYPE: DNA
<213> ORGANISM: Homo sapiens

<400> SEQUENCE: 93
gcctccagct ctatccaagt t                                              21

<210> SEQ ID NO 94
<211> LENGTH: 160
<212> TYPE: DNA
<213> ORGANISM: Homo sapiens

<400> SEQUENCE: 94
aatcctagac cttggattgc aagagactcc ttaatatctt cccatgtcca catttccttc    60
```

```
acatagtttg aatgtggctt ctattatata cagatacaag attcaaatcc aacctctatg    120
atgactggtc ttgtgaataa gcagaagagg cactaacaat                          160
```

<210> SEQ ID NO 95
<211> LENGTH: 22
<212> TYPE: DNA
<213> ORGANISM: Homo sapiens

<400> SEQUENCE: 95

```
ccttaatatc ttcccatgtc ca                                              22
```

<210> SEQ ID NO 96
<211> LENGTH: 22
<212> TYPE: DNA
<213> ORGANISM: Homo sapiens

<400> SEQUENCE: 96

```
attgttagtg cctcttctgc tt                                              22
```

<210> SEQ ID NO 97
<211> LENGTH: 162
<212> TYPE: DNA
<213> ORGANISM: Homo sapiens

<400> SEQUENCE: 97

```
aagagaagtg aggtcagcag ctgcaagcca cctccgtcat ttagaaaagc ttcatgatgt    60
agtgtgtcgt ttcgatgtga cactgtctca cagagttaaa atgatgttaa ggaactgttc   120
aatggaaatt tagaaatttc tcttttctc aattttagtg ta                       162
```

<210> SEQ ID NO 98
<211> LENGTH: 20
<212> TYPE: DNA
<213> ORGANISM: Homo sapiens

<400> SEQUENCE: 98

```
gagaagtgag gtcagcagct                                                 20
```

<210> SEQ ID NO 99
<211> LENGTH: 22
<212> TYPE: DNA
<213> ORGANISM: Homo sapiens

<400> SEQUENCE: 99

```
tttctaaatt tccattgaac ag                                              22
```

<210> SEQ ID NO 100
<211> LENGTH: 160
<212> TYPE: DNA
<213> ORGANISM: Homo sapiens

<400> SEQUENCE: 100

```
atggctgaat agtattccct tgtgtatata tctatttatc cttttattca ttgatggaca    60
cttaggctga ttttctctct tctcatggct ggcttctcat cacccttggg tcctcctgta   120
tcctcgtgta ataaagctct tccccaatat ctcgatagat                          160
```

<210> SEQ ID NO 101
<211> LENGTH: 22
<212> TYPE: DNA
<213> ORGANISM: Homo sapiens

<400> SEQUENCE: 101
ggctgaatag tattcccttg tg                                        22

<210> SEQ ID NO 102
<211> LENGTH: 20
<212> TYPE: DNA
<213> ORGANISM: Homo sapiens

<400> SEQUENCE: 102
tcgagatatt ggggaagagc                                           20

<210> SEQ ID NO 103
<211> LENGTH: 199
<212> TYPE: DNA
<213> ORGANISM: Homo sapiens

<400> SEQUENCE: 103
cattttaact tgattacctc cacaaagact attccagaat aaggttatgt tctgaggtat    60
taggggttac aacttcaaca tatgaatttt gagtggacac aattcaaccc atagcacctc   120
cgtgtaagag ctgggaaggg aaagtggcta agttgtgcaa atgtgcacat tggttggaga   180
tgattaactt ctggcatgt                                              199

<210> SEQ ID NO 104
<211> LENGTH: 22
<212> TYPE: DNA
<213> ORGANISM: Homo sapiens

<400> SEQUENCE: 104
cctccacaaa gactattcca ga                                        22

<210> SEQ ID NO 105
<211> LENGTH: 20
<212> TYPE: DNA
<213> ORGANISM: Homo sapiens

<400> SEQUENCE: 105
cactttccct tcccagctct                                           20

<210> SEQ ID NO 106
<211> LENGTH: 157
<212> TYPE: DNA
<213> ORGANISM: Homo sapiens

<400> SEQUENCE: 106 aggggggaaat tgcaatctg attctaaaat tcatacggaa aaaacaatg gagttagaat    60 aactaaaaca agtccgaaaa agaaaaagaa atggaggact aatgctacct gatttcaagt   120
cttatcttat aaatctacat caataaagga caagttg                          157

<210> SEQ ID NO 107
<211> LENGTH: 20
<212> TYPE: DNA
<213> ORGANISM: Homo sapiens

<400> SEQUENCE: 107
gaaattggca atctgattct                                           20

<210> SEQ ID NO 108
<211> LENGTH: 21
<212> TYPE: DNA
<213> ORGANISM: Homo sapiens

```
<400> SEQUENCE: 108
caacttgtcc tttattgatg t                                              21

<210> SEQ ID NO 109
<211> LENGTH: 173
<212> TYPE: DNA
<213> ORGANISM: Homo sapiens

<400> SEQUENCE: 109
tctgtgtttg tctatgttga taaaacattg aaatgccaaa tagctcaaag gtcattcact    60
taagaaatct aagtactgat aacatcttag ccccgattct tcataggcat tgttaagcct   120
attataattt tggttcagag agaaggtaaa ctatattcca gacaggcata taa          173

<210> SEQ ID NO 110
<211> LENGTH: 22
<212> TYPE: DNA
<213> ORGANISM: Homo sapiens

<400> SEQUENCE: 110
ctatgttgat aaaacattga aa                                             22

<210> SEQ ID NO 111
<211> LENGTH: 20
<212> TYPE: DNA
<213> ORGANISM: Homo sapiens

<400> SEQUENCE: 111
gcctgtctgg aatatagttt                                                20

<210> SEQ ID NO 112
<211> LENGTH: 126
<212> TYPE: DNA
<213> ORGANISM: Homo sapiens

<400> SEQUENCE: 112
tgcagggcat ataatctaag ctgtaaacgt cctgtcagaa gacaacatat tcatcttgct    60
aaggtttaag ctatatgact ggcactgtgc tcaactcaga gtcattgaat gaacagtatt   120
tattta                                                              126

<210> SEQ ID NO 113
<211> LENGTH: 22
<212> TYPE: DNA
<213> ORGANISM: Homo sapiens

<400> SEQUENCE: 113
cagggcatat aatctaagct gt                                             22

<210> SEQ ID NO 114
<211> LENGTH: 21
<212> TYPE: DNA
<213> ORGANISM: Homo sapiens

<400> SEQUENCE: 114
caatgactct gagttgagca c                                              21

<210> SEQ ID NO 115
<211> LENGTH: 132
<212> TYPE: DNA
<213> ORGANISM: Homo sapiens

<400> SEQUENCE: 115
```

```
ttcacattat tcccttaaaa taaactctct ccctcccctc tcccgtctca accttgtccc    60
tttctttata taatgggtaa ttcgttaatg tcagcagaat agttttgggg ccataatggc   120
aagtatcacg tg                                                       132

<210> SEQ ID NO 116
<211> LENGTH: 19
<212> TYPE: DNA
<213> ORGANISM: Homo sapiens

<400> SEQUENCE: 116
aactctctcc ctccctct                                                  19

<210> SEQ ID NO 117
<211> LENGTH: 20
<212> TYPE: DNA
<213> ORGANISM: Homo sapiens

<400> SEQUENCE: 117
tatggcccca aaactattct                                                20

<210> SEQ ID NO 118
<211> LENGTH: 110
<212> TYPE: DNA
<213> ORGANISM: Homo sapiens

<400> SEQUENCE: 118
tcaggaagca acaagtactg ggcagattga tactgtagct aggctctagc tctatacctc    60
tagaataaat gttacaaact agcaacttga aagctaaacc tggcccacag              110

<210> SEQ ID NO 119
<211> LENGTH: 20
<212> TYPE: DNA
<213> ORGANISM: Homo sapiens

<400> SEQUENCE: 119
acaagtactg ggcagattga                                                20

<210> SEQ ID NO 120
<211> LENGTH: 20
<212> TYPE: DNA
<213> ORGANISM: Homo sapiens

<400> SEQUENCE: 120
gccaggttta gctttcaagt                                                20

<210> SEQ ID NO 121
<211> LENGTH: 106
<212> TYPE: DNA
<213> ORGANISM: Homo sapiens

<400> SEQUENCE: 121
tggttcttga gaattttata tcaggagaaa cactgtcagt ctgtattgaa aggaacagag    60
aaaattcgaa attaaagaag actattaaac ctccaaaatt ctggca                  106

<210> SEQ ID NO 122
<211> LENGTH: 22
<212> TYPE: DNA
<213> ORGANISM: Homo sapiens

<400> SEQUENCE: 122
```

```
ttttatatca ggagaaacac tg                                              22

<210> SEQ ID NO 123
<211> LENGTH: 21
<212> TYPE: DNA
<213> ORGANISM: Homo sapiens

<400> SEQUENCE: 123 ccagaattt ggaggtttaa t                                                21

<210> SEQ ID NO 124
<211> LENGTH: 171
<212> TYPE: DNA
<213> ORGANISM: Homo sapiens

<400> SEQUENCE: 124
gcatcaaact acacactgtc attcctcctt tatctccaaa agcttgaaaa ttcctcactt     60
gtatctcatt ctttctctct tagaaaactg atcacctctg atgaattaga acggaatgac    120
caagctttgg gagaggcaaa agaatctcgg tgttaaagac tcagagttta a             171

<210> SEQ ID NO 125
<211> LENGTH: 22
<212> TYPE: DNA
<213> ORGANISM: Homo sapiens

<400> SEQUENCE: 125
tgtcattcct cctttatctc ca                                              22

<210> SEQ ID NO 126
<211> LENGTH: 20
<212> TYPE: DNA
<213> ORGANISM: Homo sapiens

<400> SEQUENCE: 126
ttcttttgcc tctcccaaag                                                 20

<210> SEQ ID NO 127
<211> LENGTH: 163
<212> TYPE: DNA
<213> ORGANISM: Homo sapiens

<400> SEQUENCE: 127
ttgaaaatta agaaaccctg gcacagtgtt gactggagcc acttacctta atagaaaata     60
aagctcacat atatccataa tgaaaagcag agaccagcac aaccatagtc acctgacagt    120
tttaaaatcc aaggccagga tcttctcaac tcaggcccac tca                      163

<210> SEQ ID NO 128
<211> LENGTH: 20
<212> TYPE: DNA
<213> ORGANISM: Homo sapiens

<400> SEQUENCE: 128
accctggcac agtgttgact                                                 20

<210> SEQ ID NO 129
<211> LENGTH: 20
<212> TYPE: DNA
<213> ORGANISM: Homo sapiens

<400> SEQUENCE: 129
tgggcctgag ttgagaagat                                                 20
```

```
<210> SEQ ID NO 130
<211> LENGTH: 20
<212> TYPE: DNA
<213> ORGANISM: Homo sapiens

<400> SEQUENCE: 130
tttttcccat ttccaactct                                                   20

<210> SEQ ID NO 131
<211> LENGTH: 122
<212> TYPE: DNA
<213> ORGANISM: Homo sapiens

<400> SEQUENCE: 131
aaaaaaaaag atgagacagg caggtgcgaa agaaataaaa gtcaaaactg atccagttgg       60
gaaactcaga attgacagtt acgtgtcctt tcatttattg atattttgag attcacaggg      120
gt                                                                     122

<210> SEQ ID NO 132
<211> LENGTH: 20
<212> TYPE: DNA
<213> ORGANISM: Homo sapiens

<400> SEQUENCE: 132
aaaagatgag acaggcaggt                                                   20

<210> SEQ ID NO 133
<211> LENGTH: 20
<212> TYPE: DNA
<213> ORGANISM: Homo sapiens

<400> SEQUENCE: 133
acccctgtga atctcaaaat                                                   20

<210> SEQ ID NO 134
<211> LENGTH: 150
<212> TYPE: DNA
<213> ORGANISM: Homo sapiens

<400> SEQUENCE: 134
gagttaaata aagcacttgc ttctattgtt tgtacctaaa cttaacagaa cacagtaagt       60
aacaagtcat tgggatgcag aaaagaaaaa agagagtgaa ggaaggagaa aaggtgaagg      120
gagaatggaa gagaggaagg gagggaggaa                                       150

<210> SEQ ID NO 135
<211> LENGTH: 21
<212> TYPE: DNA
<213> ORGANISM: Homo sapiens

<400> SEQUENCE: 135
gcacttgctt ctattgtttg t                                                 21

<210> SEQ ID NO 136
<211> LENGTH: 20
<212> TYPE: DNA
<213> ORGANISM: Homo sapiens

<400> SEQUENCE: 136
cccttcctct cttccattct                                                   20
```

```
<210> SEQ ID NO 137
<211> LENGTH: 129
<212> TYPE: DNA
<213> ORGANISM: Homo sapiens

<400> SEQUENCE: 137
aaacgagcca ccagtgggag cactgcaggt atctgtgtga gacccgtact tcacaactcc      60
tgctttccct ccataaagta gcttgcattt tccacattga ctttgcagtt ctttggtatc     120
tgtattggt                                                             129

<210> SEQ ID NO 138
<211> LENGTH: 18
<212> TYPE: DNA
<213> ORGANISM: Homo sapiens

<400> SEQUENCE: 138
gtgggagcac tgcaggta                                                    18

<210> SEQ ID NO 139
<211> LENGTH: 21
<212> TYPE: DNA
<213> ORGANISM: Homo sapiens

<400> SEQUENCE: 139
acagatacca agaactgca a                                                 21

<210> SEQ ID NO 140
<211> LENGTH: 145
<212> TYPE: DNA
<213> ORGANISM: Homo sapiens

<400> SEQUENCE: 140
tggacacctt tcaacttaga aatcataaac agattcattt ccttaaagtt aatgaaaaga      60
attaacagac cctcctcaaa aaagacatat atgcagccta caatcatatg aaaaaaagtt    120
caacattact gttcagcaaa tcaaa                                          145

<210> SEQ ID NO 141
<211> LENGTH: 20
<212> TYPE: DNA
<213> ORGANISM: Homo sapiens

<400> SEQUENCE: 141
tggacacctt tcaacttaga                                                  20

<210> SEQ ID NO 142
<211> LENGTH: 22
<212> TYPE: DNA
<213> ORGANISM: Homo sapiens

<400> SEQUENCE: 142
gaacagtaat gttgaacttt tt                                               22

<210> SEQ ID NO 143
<211> LENGTH: 155
<212> TYPE: DNA
<213> ORGANISM: Homo sapiens

<400> SEQUENCE: 143
tggatacatt cctagaaata gatggaaact gctcttgcaa aaagcttagc acatgttaaa      60
aattttagaa acaatttgcc aaagtttatt tagtctagtg attttgacag gttaaatgga    120
```

-continued ccctttgaga tcttttttcc tcaagtacaa aggct          155

<210> SEQ ID NO 144
<211> LENGTH: 21
<212> TYPE: DNA
<213> ORGANISM: Homo sapiens

<400> SEQUENCE: 144
tcttgcaaaa agcttagcac a          21

<210> SEQ ID NO 145
<211> LENGTH: 21
<212> TYPE: DNA
<213> ORGANISM: Homo sapiens

<400> SEQUENCE: 145
aaaaagatct caaagggtcc a          21

<210> SEQ ID NO 146
<211> LENGTH: 119
<212> TYPE: DNA
<213> ORGANISM: Homo sapiens

<400> SEQUENCE: 146
gcttttgctg aacatcaagt ggtgagccag gactcaaagc cagatcttct tgtttccctg          60
ttaggtgttt gtagcacaac tggtatctgc agactatgct gctggaaggg ctagccgtc          119

<210> SEQ ID NO 147
<211> LENGTH: 20
<212> TYPE: DNA
<213> ORGANISM: Homo sapiens

<400> SEQUENCE: 147
gcttttgctg aacatcaagt          20

<210> SEQ ID NO 148
<211> LENGTH: 19
<212> TYPE: DNA
<213> ORGANISM: Homo sapiens

<400> SEQUENCE: 148
ccttccagca gcatagtct          19

<210> SEQ ID NO 149
<211> LENGTH: 161
<212> TYPE: DNA
<213> ORGANISM: Homo sapiens

<400> SEQUENCE: 149
actgtcctag aaaatccagg atgtgcagtg atcatgtatg aatgcatgga cctgcacaca          60
caggagtgaa caaaagaccc acccctgcca ggtcaccact catatctcac cccagcccac          120
gctagctcac actcctcccc acacaccact gacctcatca t          161

<210> SEQ ID NO 150
<211> LENGTH: 18
<212> TYPE: DNA
<213> ORGANISM: Homo sapiens

<400> SEQUENCE: 150
aaatccagga tgtgcagt          18

```
<210> SEQ ID NO 151
<211> LENGTH: 19
<212> TYPE: DNA
<213> ORGANISM: Homo sapiens

<400> SEQUENCE: 151
atgatgaggt cagtggtgt                                                    19

<210> SEQ ID NO 152
<211> LENGTH: 124
<212> TYPE: DNA
<213> ORGANISM: Homo sapiens

<400> SEQUENCE: 152
cacatcacag atcatagtaa atggctttaa tttttaacg aaatctcact actgcaaatg         60
cattgttgtc ctagctaatg aatgcataga gtattgcctg caaataata attgagattc       120 tatt                                                                   124

<210> SEQ ID NO 153
<211> LENGTH: 22
<212> TYPE: DNA
<213> ORGANISM: Homo sapiens

<400> SEQUENCE: 153
catcacagat catagtaaat gg                                                22

<210> SEQ ID NO 154
<211> LENGTH: 21
<212> TYPE: DNA
<213> ORGANISM: Homo sapiens

<400> SEQUENCE: 154
aattattatt ttgcaggcaa t                                                 21

<210> SEQ ID NO 155
<211> LENGTH: 151
<212> TYPE: DNA
<213> ORGANISM: Homo sapiens

<400> SEQUENCE: 155
ttatcctcca catcctcatg aggcaaacac ctttcctacc ttaccgctcc ccagtggcct        60
ccctgttgcc ttcttattca agactaagac tctctagaat gttctttatc ctgagtccag      120
ctgattgtct atactaatat cagtacgggg t                                     151

<210> SEQ ID NO 156
<211> LENGTH: 20
<212> TYPE: DNA
<213> ORGANISM: Homo sapiens

<400> SEQUENCE: 156
catgaggcaa acacctttcc                                                   20

<210> SEQ ID NO 157
<211> LENGTH: 22
<212> TYPE: DNA
<213> ORGANISM: Homo sapiens

<400> SEQUENCE: 157
gctggactca ggataaagaa ca                                                22
```

<210> SEQ ID NO 158
<211> LENGTH: 145
<212> TYPE: DNA
<213> ORGANISM: Homo sapiens

<400> SEQUENCE: 158
agggtgcagc actttattat ggaagcctga gctgactaat acaggtgtct ctatatctca    60
ctgagggaaa gtgacaggaa agtaagaacc atttatgtcc aagagtccag aggagtcaac   120
cagattctgg gggaaaagaa ggtac                                          145

<210> SEQ ID NO 159
<211> LENGTH: 20
<212> TYPE: DNA
<213> ORGANISM: Homo sapiens

<400> SEQUENCE: 159
tggaagcctg agctgactaa                                                 20

<210> SEQ ID NO 160
<211> LENGTH: 20
<212> TYPE: DNA
<213> ORGANISM: Homo sapiens

<400> SEQUENCE: 160
ccttcttttc ccccagaatc                                                 20

<210> SEQ ID NO 161
<211> LENGTH: 154
<212> TYPE: DNA
<213> ORGANISM: Homo sapiens

<400> SEQUENCE: 161
tgagaattta ggagaacaga agatcagagg gctgcacagg ctaaactaga caatgagccc    60
atgcaagtaa gttaagagga gaagcgggta agtatgcacc tgctttgtct aggtgaccag   120
caagcattta gcaatagtct tttcaaaaca acag                                154

<210> SEQ ID NO 162
<211> LENGTH: 22
<212> TYPE: DNA
<213> ORGANISM: Homo sapiens

<400> SEQUENCE: 162
ttaggagaac agaagatcag ag                                              22

<210> SEQ ID NO 163
<211> LENGTH: 22
<212> TYPE: DNA
<213> ORGANISM: Homo sapiens

<400> SEQUENCE: 163
aaagactatt gctaaatgct tg                                              22

<210> SEQ ID NO 164
<211> LENGTH: 106
<212> TYPE: DNA
<213> ORGANISM: Homo sapiens

<400> SEQUENCE: 164
aaacaggcaa aataagcgta gggctgtgtg tgcaacagtt aatcataaag ccatcaccag    60
gagacgtcac tgggcgcctt ctggagtcta tccgtcctaa ctttgc                   106

```
<210> SEQ ID NO 165
<211> LENGTH: 20
<212> TYPE: DNA
<213> ORGANISM: Homo sapiens

<400> SEQUENCE: 165
taagcgtagg gctgtgtgtg                                          20

<210> SEQ ID NO 166
<211> LENGTH: 21
<212> TYPE: DNA
<213> ORGANISM: Homo sapiens

<400> SEQUENCE: 166
ggacggatag actccagaag g                                        21

<210> SEQ ID NO 167
<211> LENGTH: 105
<212> TYPE: DNA
<213> ORGANISM: Homo sapiens

<400> SEQUENCE: 167
gaatgacctt ggcactttta tcaaacatca actggccaca cacaggtgag tctacttctg   60
gacacttatc ctgttccatt catctgtata tctctatcct tacac                  105

<210> SEQ ID NO 168
<211> LENGTH: 23
<212> TYPE: DNA
<213> ORGANISM: Homo sapiens

<400> SEQUENCE: 168
gaatgacctt ggcactttta tca                                      23

<210> SEQ ID NO 169
<211> LENGTH: 27
<212> TYPE: DNA
<213> ORGANISM: Homo sapiens

<400> SEQUENCE: 169
aaggatagag atatacagat gaatgga                                  27

<210> SEQ ID NO 170
<211> LENGTH: 129
<212> TYPE: DNA
<213> ORGANISM: Homo sapiens

<400> SEQUENCE: 170
ctgctggaat aggctgcttg gccatgttct tggaagctac caccatatca aggtaatttc   60
ccacacaaca ttccagcccc tgctttcctc tctggcctta tctagggcca ttccccaact  120
caggtgaat                                                         129

<210> SEQ ID NO 171
<211> LENGTH: 20
<212> TYPE: DNA
<213> ORGANISM: Homo sapiens

<400> SEQUENCE: 171
ggccatgttc ttggaagcta                                          20

<210> SEQ ID NO 172
<211> LENGTH: 20
```

<212> TYPE: DNA
<213> ORGANISM: Homo sapiens

<400> SEQUENCE: 172
ttcacctgag ttggggaatg                                            20

<210> SEQ ID NO 173
<211> LENGTH: 138
<212> TYPE: DNA
<213> ORGANISM: Homo sapiens

<400> SEQUENCE: 173
acctttgttc catgcaccgc gcaaatacct gggaacccett attgcccaac tcaagagcca    60
gagtcctctg tcatcatttt gcctctctcc taagtgagag gactgagtgc agacttggtg   120
tttgtgggtg aggcatgt                                                 138

<210> SEQ ID NO 174
<211> LENGTH: 18
<212> TYPE: DNA
<213> ORGANISM: Homo sapiens

<400> SEQUENCE: 174
catgcaccgc gcaaatac                                              18

<210> SEQ ID NO 175
<211> LENGTH: 19
<212> TYPE: DNA
<213> ORGANISM: Homo sapiens

<400> SEQUENCE: 175
atgcctcacc cacaaacac                                             19

<210> SEQ ID NO 176
<211> LENGTH: 159
<212> TYPE: DNA
<213> ORGANISM: Homo sapiens

<400> SEQUENCE: 176
ctcctgagtc caagcccttc tcactcacct cttcttgaa ctaatttctt cctgtttttt    60
tccagtcctc ccttctgttc atgtctctcc tctgcacact tccattttgt ggttcagaaa   120
atgtcaccgt cccagtcaca cttgccttat ggctgttgt                          159

<210> SEQ ID NO 177
<211> LENGTH: 20
<212> TYPE: DNA
<213> ORGANISM: Homo sapiens

<400> SEQUENCE: 177
tccaagccct tctcactcac                                            20

<210> SEQ ID NO 178
<211> LENGTH: 20
<212> TYPE: DNA
<213> ORGANISM: Homo sapiens

<400> SEQUENCE: 178
ctgggacggt gacattttct                                            20

<210> SEQ ID NO 179
<211> LENGTH: 132
<212> TYPE: DNA

<213> ORGANISM: Homo sapiens

<400> SEQUENCE: 179

```
cccaggaaga gtggaaagat taacctttgt gagccaaacc agtgacactt gattacttga    60
cagaactaat ccttctgtcc tgatgacaga acttcaacta cacaggtaca tgcaagctaa   120
tatctgttgt aa                                                       132
```

<210> SEQ ID NO 180
<211> LENGTH: 21
<212> TYPE: DNA
<213> ORGANISM: Homo sapiens

<400> SEQUENCE: 180

```
cccaggaaga gtggaaagat t                                              21
```

<210> SEQ ID NO 181
<211> LENGTH: 21
<212> TYPE: DNA
<213> ORGANISM: Homo sapiens

<400> SEQUENCE: 181

```
ttagcttgca tgtacctgtg t                                              21
```

<210> SEQ ID NO 182
<211> LENGTH: 165
<212> TYPE: DNA
<213> ORGANISM: Homo sapiens

<400> SEQUENCE: 182

```
gcctggcaag ctagatgggg tgaattttca cctgccacag ccgcaagtca aagccaccgg    60
cttctctctt ctccctccca ttgctcctga cagccagggt taatattttg cctcatgtaa   120
acagggaggc atccacccga gaatctcccc tcagcccaca taagc                   165
```

<210> SEQ ID NO 183
<211> LENGTH: 20
<212> TYPE: DNA
<213> ORGANISM: Homo sapiens

<400> SEQUENCE: 183

```
agctagatgg ggtgaatttt                                                20
```

<210> SEQ ID NO 184
<211> LENGTH: 18
<212> TYPE: DNA
<213> ORGANISM: Homo sapiens

<400> SEQUENCE: 184

```
tgggctgagg ggagattc                                                  18
```

<210> SEQ ID NO 185
<211> LENGTH: 160
<212> TYPE: DNA
<213> ORGANISM: Homo sapiens

<400> SEQUENCE: 185

```
atcaagctaa ttaatgttat ctatcacttc acatagttca accttttttt gtggtgagag    60
tactgaagat ctactctctt agcaattttc aaatctaaaa tacattatta ttaacacagt   120
cactgtgccg tacgttagct ctgaggacct tattcatttt                         160
```

```
<210> SEQ ID NO 186
<211> LENGTH: 22
<212> TYPE: DNA
<213> ORGANISM: Homo sapiens

<400> SEQUENCE: 186
atcaagctaa ttaatgttat ct                                          22

<210> SEQ ID NO 187
<211> LENGTH: 20
<212> TYPE: DNA
<213> ORGANISM: Homo sapiens

<400> SEQUENCE: 187
aatgaataag gtcctcagag                                             20

<210> SEQ ID NO 188
<211> LENGTH: 124
<212> TYPE: DNA
<213> ORGANISM: Homo sapiens

<400> SEQUENCE: 188
tttaatctga tcattgccct atgaggtagg gagtattctg attcccattt tataaataag  60
gaacccgagg cttagagagc atcagtgact tgttcaaggt cacccacagc tgtcaagtga 120
caga                                                             124

<210> SEQ ID NO 189
<211> LENGTH: 21
<212> TYPE: DNA
<213> ORGANISM: Homo sapiens

<400> SEQUENCE: 189
tttaatctga tcattgccct a                                           21

<210> SEQ ID NO 190
<211> LENGTH: 18
<212> TYPE: DNA
<213> ORGANISM: Homo sapiens

<400> SEQUENCE: 190
agctgtgggt gaccttga                                               18

<210> SEQ ID NO 191
<211> LENGTH: 128
<212> TYPE: DNA
<213> ORGANISM: Homo sapiens

<400> SEQUENCE: 191
tgtcccacca ttgtgtatta ggtttgtaga gcgtagacaa cttgcctttt tagtttgtag  60
gtttctgtat caagagaaga tgtgtgtggg cctaacctag attacaggat cctggacttc 120
aagtctga                                                         128

<210> SEQ ID NO 192
<211> LENGTH: 20
<212> TYPE: DNA
<213> ORGANISM: Homo sapiens

<400> SEQUENCE: 192
tgtcccacca ttgtgtatta                                             20

<210> SEQ ID NO 193
```

```
<211> LENGTH: 20
<212> TYPE: DNA
<213> ORGANISM: Homo sapiens

<400> SEQUENCE: 193
tcagacttga agtccaggat                                                  20

<210> SEQ ID NO 194
<211> LENGTH: 128
<212> TYPE: DNA
<213> ORGANISM: Homo sapiens

<400> SEQUENCE: 194
tcatttgcta aggtcggata gctcctaatt ggcaaagtca cgatgggatc ccagggattc      60
tgaggatgaa gcctgtgttt aataactatt atgccaagtg agcattttca aatatatgag     120
agaaatta                                                              128

<210> SEQ ID NO 195
<211> LENGTH: 19
<212> TYPE: DNA
<213> ORGANISM: Homo sapiens

<400> SEQUENCE: 195
catttgctaa ggtcggata                                                   19

<210> SEQ ID NO 196
<211> LENGTH: 20
<212> TYPE: DNA
<213> ORGANISM: Homo sapiens

<400> SEQUENCE: 196
tatttgaaaa tgctcacttg                                                  20

<210> SEQ ID NO 197
<211> LENGTH: 159
<212> TYPE: DNA
<213> ORGANISM: Homo sapiens

<400> SEQUENCE: 197
cattgcttca ggggtgttag ttttgtgttc acaactagat tataaactcc tcttgcattc      60
ctgatggcag tgacttgaag gcatttattt gaagaataat agacatacag aaagggggcac    120 atgtcataaa ggtacagctg gacgactttt cacaaagtg                            159

<210> SEQ ID NO 198
<211> LENGTH: 20
<212> TYPE: DNA
<213> ORGANISM: Homo sapiens

<400> SEQUENCE: 198
gcttcagggg tgttagtttt                                                  20

<210> SEQ ID NO 199
<211> LENGTH: 20
<212> TYPE: DNA
<213> ORGANISM: Homo sapiens

<400> SEQUENCE: 199
ctttgtgaaa agtcgtccag                                                  20

<210> SEQ ID NO 200
<211> LENGTH: 117
```

```
<212> TYPE: DNA
<213> ORGANISM: Homo sapiens

<400> SEQUENCE: 200
gagaggatgg tgccatcatg gaaagcatgg ggcagtcatg gagatgacgg agtagctcat    60
ggagaagata atgccatcat ggaaggcata gtgcagtcat ggagatgatg gtgcagc     117

<210> SEQ ID NO 201
<211> LENGTH: 18
<212> TYPE: DNA
<213> ORGANISM: Homo sapiens

<400> SEQUENCE: 201
ccatcatgga aagcatgg                                                  18

<210> SEQ ID NO 202
<211> LENGTH: 20
<212> TYPE: DNA
<213> ORGANISM: Homo sapiens

<400> SEQUENCE: 202
tcatctccat gactgcacta                                                20

<210> SEQ ID NO 203
<211> LENGTH: 167
<212> TYPE: DNA
<213> ORGANISM: Homo sapiens

<400> SEQUENCE: 203
atggggcagt catggagatg acggagtagc tcatggagaa aataatgcca tcatggaagg    60
catagtgcag tcatggagat gatggtgcag ctcatggaga agatggtgcc atcatggaag   120
gcatggtgca atcatggagt agacagtgca gctgggccaa gattctc                 167

<210> SEQ ID NO 204
<211> LENGTH: 20
<212> TYPE: DNA
<213> ORGANISM: Homo sapiens

<400> SEQUENCE: 204
gagatgacgg agtagctcat                                                20

<210> SEQ ID NO 205
<211> LENGTH: 18
<212> TYPE: DNA
<213> ORGANISM: Homo sapiens

<400> SEQUENCE: 205
cccagctgca ctgtctac                                                  18

<210> SEQ ID NO 206
<211> LENGTH: 128
<212> TYPE: DNA
<213> ORGANISM: Homo sapiens

<400> SEQUENCE: 206
gatgtgcctc tcttgttcca atcacaggac aggggtataa ctaggggcac tgtctatact    60
ggctgcactc tggccagtgc tgtcccaggt agattcatca gggtctagag cttcagctaa   120
cagcatga                                                            128

<210> SEQ ID NO 207
```

```
<211> LENGTH: 20
<212> TYPE: DNA
<213> ORGANISM: Homo sapiens

<400> SEQUENCE: 207
tcttgttcca atcacaggac                                              20

<210> SEQ ID NO 208
<211> LENGTH: 20
<212> TYPE: DNA
<213> ORGANISM: Homo sapiens

<400> SEQUENCE: 208
atgctgttag ctgaagctct                                              20

<210> SEQ ID NO 209
<211> LENGTH: 109
<212> TYPE: DNA
<213> ORGANISM: Homo sapiens

<400> SEQUENCE: 209
ttttattcat taagttgaaa gctcctaaag cagagggacc atattttat gtcccaactc    60 tccttaaggc cttgcctatg atagcacatc tcttcaatag aattgtcct              109

<210> SEQ ID NO 210
<211> LENGTH: 20
<212> TYPE: DNA
<213> ORGANISM: Homo sapiens

<400> SEQUENCE: 210
tgaaagctcc taaagcagag                                              20

<210> SEQ ID NO 211
<211> LENGTH: 20
<212> TYPE: DNA
<213> ORGANISM: Homo sapiens

<400> SEQUENCE: 211
ttgaagagat gtgctatcat                                              20

<210> SEQ ID NO 212
<211> LENGTH: 163
<212> TYPE: DNA
<213> ORGANISM: Homo sapiens

<400> SEQUENCE: 212
cacataacta ataaatttgt aagtatgtgc aacggctcac acttgcttcc agaatggcac  60
ctaaaaaaca gatttacctc tcccaaatt cagatatgga attaaatgta atgtcaggaa  120
aactgtctaa gagttggaaa tgggaaaaaa atgttctttt ggt                   163

<210> SEQ ID NO 213
<211> LENGTH: 21
<212> TYPE: DNA
<213> ORGANISM: Homo sapiens

<400> SEQUENCE: 213
aatttgtaag tatgtgcaac g                                            21

<210> SEQ ID NO 214
<211> LENGTH: 207
<212> TYPE: DNA
<213> ORGANISM: Homo sapiens
```

<400> SEQUENCE: 214
aaagaccagc ttttagctga acatcagggc tgccttcaga gtttaattac cgccctcccc       60
atggggccaa atgagccatc gactcctccc aagggggttc ggcttggtac tgatctttaa      120
gtaagtaaac gctaaaccag ctcatcttaa agcgcccaca tctgatttcc tgctctgctg      180
caagacagta ggtgactggt aatgacc                                          207

<210> SEQ ID NO 215
<211> LENGTH: 20
<212> TYPE: DNA
<213> ORGANISM: Homo sapiens

<400> SEQUENCE: 215
agggctgcct tcagagttta                                                   20

<210> SEQ ID NO 216
<211> LENGTH: 20
<212> TYPE: DNA
<213> ORGANISM: Homo sapiens

<400> SEQUENCE: 216
gcgctttaag atgagctggt                                                   20

<210> SEQ ID NO 217
<211> LENGTH: 192
<212> TYPE: DNA
<213> ORGANISM: Homo sapiens

<400> SEQUENCE: 217
actctgctcc cagtgtgaac atggggaaag ttgattaaac tctctgactt cagattcctc       60
atgtaaaatg tggggaaaca gctctgactt aatggtgtca ctgtgaggag taaatgaggt      120
agcatattta aaggattttg tatagtgctg gtgacagtaa ccagccaata gatgatatag      180
ctagtaatag ca                                                          192

<210> SEQ ID NO 218
<211> LENGTH: 20
<212> TYPE: DNA
<213> ORGANISM: Homo sapiens

<400> SEQUENCE: 218
tgaacatggg gaaagttgat                                                   20

<210> SEQ ID NO 219
<211> LENGTH: 22
<212> TYPE: DNA
<213> ORGANISM: Homo sapiens

<400> SEQUENCE: 219
tcaccagcac tatacaaaat cc                                                22

<210> SEQ ID NO 220
<211> LENGTH: 170
<212> TYPE: DNA
<213> ORGANISM: Homo sapiens

<400> SEQUENCE: 220
cttcactgac cacttcctta actgtccact ccgaaacacc ccttcttcct gttcttccaa       60
tacaccaaac tctttcttgc ctctgtgtgc ttgcccatgc tgttccttct ggcttcttcc      120
ttcacattca agtcttgact tagatgtcac ttgccaaggg agaccttgga 170

```
<210> SEQ ID NO 221
<211> LENGTH: 21
<212> TYPE: DNA
<213> ORGANISM: Homo sapiens

<400> SEQUENCE: 221
```
acttccttaa ctgtccactc c 21

```
<210> SEQ ID NO 222
<211> LENGTH: 19
<212> TYPE: DNA
<213> ORGANISM: Homo sapiens

<400> SEQUENCE: 222
```
ccttggcaag tgacatcta 19

```
<210> SEQ ID NO 223
<211> LENGTH: 181
<212> TYPE: DNA
<213> ORGANISM: Homo sapiens

<400> SEQUENCE: 223
```
aaacatccca atagacaaaa ctccaagaag agtcaaaaca agaataaagt acaggtcatc 60
ttttcttttg cactcctgac agcactttgt acatggtaat aataatctac caattaacta 120
cataagccac atggttttat catagtgtga agctttgtat ccagaaagga gagaaggctc 180
c 181

```
<210> SEQ ID NO 224
<211> LENGTH: 22
<212> TYPE: DNA
<213> ORGANISM: Homo sapiens

<400> SEQUENCE: 224
```
ccaagaagag tcaaaacaag aa 22

```
<210> SEQ ID NO 225
<211> LENGTH: 21
<212> TYPE: DNA
<213> ORGANISM: Homo sapiens

<400> SEQUENCE: 225
```
tctcctttct ggatacaaag c 21

```
<210> SEQ ID NO 226
<211> LENGTH: 149
<212> TYPE: DNA
<213> ORGANISM: Homo sapiens

<400> SEQUENCE: 226
```
ggcagaggca tggggtgcat agggatatgg ggtgggccag tttgctcctc agaccagaag 60
gggtgcagga ctcccccccga tcaggatcat ggagaaaggt gtggacagag gaagggaggg 120
agggagaaat ggcagctgcc ctgcagtgg 149

```
<210> SEQ ID NO 227
<211> LENGTH: 20
<212> TYPE: DNA
<213> ORGANISM: Homo sapiens

<400> SEQUENCE: 227
```

```
ttgctcctca gaccagaagg                                              20

<210> SEQ ID NO 228
<211> LENGTH: 20
<212> TYPE: DNA
<213> ORGANISM: Homo sapiens

<400> SEQUENCE: 228
ctcccttcct ctgtccacac                                              20

<210> SEQ ID NO 229
<211> LENGTH: 165
<212> TYPE: DNA
<213> ORGANISM: Homo sapiens

<400> SEQUENCE: 229
cagggactaa gtgtctctga caatacattc agccactact acagtatgaa gccagcccct   60
catccccacc ttcagagacc cctggtgcct cagattcctc ggccattctg gagctgctgt  120
gcccgaggct tgtgtagttg gagatcattt tggcagtcag tgctg                  165

<210> SEQ ID NO 230
<211> LENGTH: 22
<212> TYPE: DNA
<213> ORGANISM: Homo sapiens

<400> SEQUENCE: 230
tgtctctgac aatacattca gc                                           22

<210> SEQ ID NO 231
<211> LENGTH: 20
<212> TYPE: DNA
<213> ORGANISM: Homo sapiens

<400> SEQUENCE: 231
ctgactgcca aaatgatctc                                              20

<210> SEQ ID NO 232
<211> LENGTH: 181
<212> TYPE: DNA
<213> ORGANISM: Homo sapiens

<400> SEQUENCE: 232
cctgtctccg tgcgtgaaag ccggctccaa agtgccttct gtcctatctg ccttccgcac   60
ctggctttcc tgaaagaaag aaaacgcgtg gcttatcttt tcacggcacg ccaccttcac  120
tctcactttt tcttttctaa taaataccct tggatgggtt agtggtaatc tctcctcaaa  180
c                                                                  181

<210> SEQ ID NO 233
<211> LENGTH: 20
<212> TYPE: DNA
<213> ORGANISM: Homo sapiens

<400> SEQUENCE: 233
gctccaaagt gccttctgtc                                              20

<210> SEQ ID NO 234
<211> LENGTH: 20
<212> TYPE: DNA
<213> ORGANISM: Homo sapiens
```

```
<400> SEQUENCE: 234
ccactaaccc atccagaggt                                                 20

<210> SEQ ID NO 235
<211> LENGTH: 198
<212> TYPE: DNA
<213> ORGANISM: Homo sapiens

<400> SEQUENCE: 235
gggagcacaa cctaggcccc tcctggggag gtggtggagt cagaatcacg taagagacaa     60
agttccagtc cctcagtgcc ggctccattg tccctggac ttcccttaca aaccacagat    120
gcaaagagag cacttctcgg aatctccaca cagccacggt ggagcactca acccacgcga   180
ccctcgggcg caggtgct                                                 198

<210> SEQ ID NO 236
<211> LENGTH: 20
<212> TYPE: DNA
<213> ORGANISM: Homo sapiens

<400> SEQUENCE: 236
ctggggaggt ggtggagtca                                                20

<210> SEQ ID NO 237
<211> LENGTH: 20
<212> TYPE: DNA
<213> ORGANISM: Homo sapiens

<400> SEQUENCE: 237
gagtgctcca ccgtggctgt                                                20

<210> SEQ ID NO 238
<211> LENGTH: 161
<212> TYPE: DNA
<213> ORGANISM: Homo sapiens

<400> SEQUENCE: 238
cctgagaagc ttccagcaaa gcaccagcac gaaccgcccc acctccccac ctcccgcaa     60 gcgttgccgg gactgacaga ttacagagct ctggtccctc tgcactcctg ctctgccacc   120
cccagggtgt cagaatgtgc cccccacaca gtttccaaaa g                       161

<210> SEQ ID NO 239
<211> LENGTH: 18
<212> TYPE: DNA
<213> ORGANISM: Homo sapiens

<400> SEQUENCE: 239
aaagcaccag cacgaacc                                                  18

<210> SEQ ID NO 240
<211> LENGTH: 18
<212> TYPE: DNA
<213> ORGANISM: Homo sapiens

<400> SEQUENCE: 240
ggggcacatt ctgacacc                                                  18

<210> SEQ ID NO 241
<211> LENGTH: 162
<212> TYPE: DNA
<213> ORGANISM: Homo sapiens
```

<400> SEQUENCE: 241

```
atggagctgc tgcgccggcc tgagctctga tccctcctcc gacccagcct caccctgcaa      60
gcagcaccat gtggggctca gaatggggat cttaagggac cctccccaca acctcccgat     120
aagcctttcc acggagggcc aagcggaga caggagaaca ct                          162
```

<210> SEQ ID NO 242
<211> LENGTH: 19
<212> TYPE: DNA
<213> ORGANISM: Homo sapiens

<400> SEQUENCE: 242

```
ctgagctctg atccctcct                                                    19
```

<210> SEQ ID NO 243
<211> LENGTH: 18
<212> TYPE: DNA
<213> ORGANISM: Homo sapiens

<400> SEQUENCE: 243

```
ttctcctgtc tccgcttg                                                     18
```

<210> SEQ ID NO 244
<211> LENGTH: 194
<212> TYPE: DNA
<213> ORGANISM: Homo sapiens

<400> SEQUENCE: 244

```
actttcagaa tgtgctgcct tccacgtgtg aaccagactg agctcctttc tgccactgat       60
gttgaattgt ccatttgctc acatcagtgt ccacgtggca atccacagg gcgtgggtgg      120
gatcctgcag tctagacaaa gccaaggagc accgctggag ccacgttgg gcttcccaat      180
ccacatgcaa accc                                                        194
```

<210> SEQ ID NO 245
<211> LENGTH: 20
<212> TYPE: DNA
<213> ORGANISM: Homo sapiens

<400> SEQUENCE: 245

```
cctttctgcc actgatgttg                                                   20
```

<210> SEQ ID NO 246
<211> LENGTH: 19
<212> TYPE: DNA
<213> ORGANISM: Homo sapiens

<400> SEQUENCE: 246

```
ttgcatgtgg attgggaag                                                    19
```

<210> SEQ ID NO 247
<211> LENGTH: 213
<212> TYPE: DNA
<213> ORGANISM: Homo sapiens

<400> SEQUENCE: 247

```
tctccagcca gcgtgtcaca aagccgctca cctgctcgtg tgagtgtctg aatgcacgtg       60
tttgagtgtc agaggcgtgt gaaccacagc aactcaatct tgaatagggg ctgggtaaag     120
tgaggctgag acctcccggg gctgcattcc cagatggtta aggcattcta agtcacaaga     180
```

```
tgagatagga agttcgcaca agacactggt cat                                    213

<210> SEQ ID NO 248
<211> LENGTH: 20
<212> TYPE: DNA
<213> ORGANISM: Homo sapiens

<400> SEQUENCE: 248
tcacctgctc gtgtgagtgt                                                    20

<210> SEQ ID NO 249
<211> LENGTH: 20
<212> TYPE: DNA
<213> ORGANISM: Homo sapiens

<400> SEQUENCE: 249
ccttaaccat ctgggaatgc                                                    20

<210> SEQ ID NO 250
<211> LENGTH: 152
<212> TYPE: DNA
<213> ORGANISM: Homo sapiens

<400> SEQUENCE: 250
ttgagtcctc ttaagtagtt actatagtgg agaacttgag tcattctttg tagcgtgctt        60
cgtagagcag cgtgtttgtt agaaggattt gttaatcctg tatagggtct ttacgaaggc       120
tgttttcatg gaagcttctc tttgttgact cc                                     152

<210> SEQ ID NO 251
<211> LENGTH: 22
<212> TYPE: DNA
<213> ORGANISM: Homo sapiens

<400> SEQUENCE: 251
tggagaactt gagtcattct tt                                                 22

<210> SEQ ID NO 252
<211> LENGTH: 19
<212> TYPE: DNA
<213> ORGANISM: Homo sapiens

<400> SEQUENCE: 252
ggagtcaaca aagagaagc                                                     19

<210> SEQ ID NO 253
<211> LENGTH: 174
<212> TYPE: DNA
<213> ORGANISM: Homo sapiens

<400> SEQUENCE: 253
cattctctcc agctgcaaac tttcttcaac tttcctaaat tcttactaaa ttcagaggaa        60
taggataaag atcacttaga gaaagggtgc ttatggacat agcctgagtt tcctttaacc       120
tctctgcaat gggtgctttt aactagcttc tacatggcaa gctgtttcag tttg             174

<210> SEQ ID NO 254
<211> LENGTH: 21
<212> TYPE: DNA
<213> ORGANISM: Homo sapiens

<400> SEQUENCE: 254
ctttcttcaa ctttcctaaa t                                                  21
```

<210> SEQ ID NO 255
<211> LENGTH: 19
<212> TYPE: DNA
<213> ORGANISM: Homo sapiens

<400> SEQUENCE: 255
ttgccatgta gaagctagt                                                      19

<210> SEQ ID NO 256
<211> LENGTH: 175
<212> TYPE: DNA
<213> ORGANISM: Homo sapiens

<400> SEQUENCE: 256
ggacatctgg aactgcacca gcacagaacc gacacgttgt tactcatcgt cactcggcag         60
ggctgaagac caccagaact catgacaggc agacgtgcct ggcccagttg aggatgtagc        120
ttcagagcca agcgccagtc ctgttggcca cgtgggctgg gggcaggata gacca             175

<210> SEQ ID NO 257
<211> LENGTH: 19
<212> TYPE: DNA
<213> ORGANISM: Homo sapiens

<400> SEQUENCE: 257
accagcacag aaccgacac                                                      19

<210> SEQ ID NO 258
<211> LENGTH: 18
<212> TYPE: DNA
<213> ORGANISM: Homo sapiens

<400> SEQUENCE: 258
aacaggactg gcgcttgg                                                       18

<210> SEQ ID NO 259
<211> LENGTH: 182
<212> TYPE: DNA
<213> ORGANISM: Homo sapiens

<400> SEQUENCE: 259
ggctggttct gcccttggga ggtggttcct ttggctggac cagaatgtct gaagatgatc         60
aggagagggc caaggttggg gggtgcccc atgtgcaccc tgagaattgc accaggcaca        120
gtgagcaact tcagccctcc ttgtgcagag ctgcagcgta cagtgccagc cctcgctggc        180
cc                                                                       182

<210> SEQ ID NO 260
<211> LENGTH: 20
<212> TYPE: DNA
<213> ORGANISM: Homo sapiens

<400> SEQUENCE: 260
cttgggaggt ggttcctttg                                                     20

<210> SEQ ID NO 261
<211> LENGTH: 18
<212> TYPE: DNA
<213> ORGANISM: Homo sapiens

<400> SEQUENCE: 261

```
ctgcacaagg agggctga                                                  18

<210> SEQ ID NO 262
<211> LENGTH: 155
<212> TYPE: DNA
<213> ORGANISM: Homo sapiens

<400> SEQUENCE: 262
gttctcactt tactgagaaa cctggcagct tctcaggcca ccgcccaggt cacctgctca    60
ccagcaacgt gaaccacagg aactgaggct gtgcgggagg cggctctgct ctgtgctggg   120 ccccctcct cctcactcac cctcttcagt caaag                               155

<210> SEQ ID NO 263
<211> LENGTH: 20
<212> TYPE: DNA
<213> ORGANISM: Homo sapiens

<400> SEQUENCE: 263
tactgagaaa cctggcagct                                                20

<210> SEQ ID NO 264
<211> LENGTH: 20
<212> TYPE: DNA
<213> ORGANISM: Homo sapiens

<400> SEQUENCE: 264
ctttgactga agagggtgag                                                20

<210> SEQ ID NO 265
<211> LENGTH: 180
<212> TYPE: DNA
<213> ORGANISM: Homo sapiens

<400> SEQUENCE: 265
ttagtattat tattttcata tatattttt ataataatca tatattcaat tttatcatca    60 agaaaaagt tttaaaattc aaaatccttt catgtgcact gttttaaact taggtagaag   120
aaaaaaagtc actgaaaatc caagatgtaa taaacaggcc caacaaggc caacaaactt    180

<210> SEQ ID NO 266
<211> LENGTH: 20
<212> TYPE: DNA
<213> ORGANISM: Homo sapiens

<400> SEQUENCE: 266
ttcaatttta tcatcaagaa                                                20

<210> SEQ ID NO 267
<211> LENGTH: 20
<212> TYPE: DNA
<213> ORGANISM: Homo sapiens

<400> SEQUENCE: 267
ttgggcctgt ttattacatc                                                20

<210> SEQ ID NO 268
<211> LENGTH: 196
<212> TYPE: DNA
<213> ORGANISM: Homo sapiens

<400> SEQUENCE: 268
agggaacatg gccttgccca cacagatttc agacatctgg ctccagaact gtgggaggac    60
```

-continued acatttctgt tgtttagaac tgcatgttttt ttatactttg ttatggctgc cctaggcaac    120
taatacagat attattttcc acttctgaac ttagcaaaat attttttaaaa tgaaaattct    180 taaatgttgg cacagt    196

<210> SEQ ID NO 269
<211> LENGTH: 20
<212> TYPE: DNA
<213> ORGANISM: Homo sapiens

<400> SEQUENCE: 269
ttgcccacac agatttcaga    20

<210> SEQ ID NO 270
<211> LENGTH: 22
<212> TYPE: DNA
<213> ORGANISM: Homo sapiens

<400> SEQUENCE: 270
tgctaagttc agaagtggaa aa    22

<210> SEQ ID NO 271
<211> LENGTH: 120
<212> TYPE: DNA
<213> ORGANISM: Homo sapiens

<400> SEQUENCE: 271
ctggataaag gatgctacac gtccctggtg ggacagagca ggacggcagg ggatttcatt    60
acgccactca gaatggcagg caattgaaaa aacttataaa ttgtttattt ccagaatttt    120

<210> SEQ ID NO 272
<211> LENGTH: 20
<212> TYPE: DNA
<213> ORGANISM: Homo sapiens

<400> SEQUENCE: 272
ggataaagga tgctacacgt    20

<210> SEQ ID NO 273
<211> LENGTH: 20
<212> TYPE: DNA
<213> ORGANISM: Homo sapiens

<400> SEQUENCE: 273
aaaattctgg aaataaacaa    20

<210> SEQ ID NO 274
<211> LENGTH: 224
<212> TYPE: DNA
<213> ORGANISM: Homo sapiens

<400> SEQUENCE: 274
tgtcagtggt gtaatccgac tgtgaaagat cagtctaaca aaacagcggg gagagagagg    60
gctgaatcag agcaactagg tccaaagccg agggaaccac caacagatcc cctggtgacc    120
caacaagaaa tgctcacagt ctggacccag tcagagtctg caggacacag cagacattct    180
ggaagttaca acagccagga gcaagaggac gcatggcctg actg    224

<210> SEQ ID NO 275
<211> LENGTH: 20
<212> TYPE: DNA

<213> ORGANISM: Homo sapiens

<400> SEQUENCE: 275
gggagagaga gggctgaatc                                                    20

<210> SEQ ID NO 276
<211> LENGTH: 21
<212> TYPE: DNA
<213> ORGANISM: Homo sapiens

<400> SEQUENCE: 276
gctcctggct gttgtaactt c                                                  21

<210> SEQ ID NO 277
<211> LENGTH: 174
<212> TYPE: DNA
<213> ORGANISM: Homo sapiens

<400> SEQUENCE: 277
cgccagagca ccccttctca gaacagaaag cgtctctaca aagtgatccg gaagtgagtg        60
tgtgagggcg ctgcgtcctc cctgctcccc ttggagttgc cctttcttgc tcagatctgg       120
gtgccttggc cttgtcctgg gcccttccgc agccccgggg gtgatccccg ctag             174

<210> SEQ ID NO 278
<211> LENGTH: 19
<212> TYPE: DNA
<213> ORGANISM: Homo sapiens

<400> SEQUENCE: 278
ccagagcacc ccttctcag                                                     19

<210> SEQ ID NO 279
<211> LENGTH: 18
<212> TYPE: DNA
<213> ORGANISM: Homo sapiens

<400> SEQUENCE: 279
ggaagggccc aggacaag                                                      18

<210> SEQ ID NO 280
<211> LENGTH: 201
<212> TYPE: DNA
<213> ORGANISM: Homo sapiens

<400> SEQUENCE: 280
tatcttacgg atttgtcaac atcatttgag aagaagtcca taggctcagc agattttat         60 gccaggtggg ccatggcata aaaatgtgaa gaatgtgctc acttagacaa tacctgtgct       120
aaaattggaa caatacagag aagattagca aattaaaaca atgttaggaa gtcagtgtgg       180
tgaggtacgg tgcctcatgc c                                                 201

<210> SEQ ID NO 281
<211> LENGTH: 21
<212> TYPE: DNA
<213> ORGANISM: Homo sapiens

<400> SEQUENCE: 281
cagcagattt ttatgccagg t                                                  21

<210> SEQ ID NO 282
<211> LENGTH: 20

<212> TYPE: DNA
<213> ORGANISM: Homo sapiens

<400> SEQUENCE: 282
caccgtacct caccacactg                                                      20

<210> SEQ ID NO 283
<211> LENGTH: 275
<212> TYPE: DNA
<213> ORGANISM: Homo sapiens

<400> SEQUENCE: 283
aggcagggcc ctccttgcca catgtaaagc tgcacagagc ggtcactata tgtgtttcca          60
tatttgcaat ccaaccacca ccaactgagt gtgcgtcctg atcagccgag cctgcccacg         120
gtggccacag gccctctaca ttctaatctc gagagcctga gcatgtacaa attaaacgaa         180
gcaaaacgac accaccagt tctggccgta ctataggagg tttccaggaa gggtttgtga          240
acataaacat aagctaggta acactccttt ctgaa                                    275

<210> SEQ ID NO 284
<211> LENGTH: 20
<212> TYPE: DNA
<213> ORGANISM: Homo sapiens

<400> SEQUENCE: 284
aaccaccacc aactgagtgt                                                      20

<210> SEQ ID NO 285
<211> LENGTH: 20
<212> TYPE: DNA
<213> ORGANISM: Homo sapiens

<400> SEQUENCE: 285
cctcctatag tacggccaga                                                      20

<210> SEQ ID NO 286
<211> LENGTH: 230
<212> TYPE: DNA
<213> ORGANISM: Homo sapiens

<400> SEQUENCE: 286
tcagagcatc gcctcagtgg ccatcaatag ctcgggggac tggattgctt ttggctgttc          60
aggtttgtcc ccagcctggg tggtagagat ggactcccca ttagggacca gtgctgcccg         120
gctacaggct tacttgacag ccacccactg ggggtgccct cccctccccc agttgtcttc         180
catggggtgc cctctccccc agccgccttt cagaagggc cctcccctcc                    230

<210> SEQ ID NO 287
<211> LENGTH: 20
<212> TYPE: DNA
<213> ORGANISM: Homo sapiens

<400> SEQUENCE: 287
tggattgctt ttggctgttc                                                      20

<210> SEQ ID NO 288
<211> LENGTH: 20
<212> TYPE: DNA
<213> ORGANISM: Homo sapiens

<400> SEQUENCE: 288

-continued

| | |
|---|---|
| caccccatgg aagacaactg | 20 |

<210> SEQ ID NO 289
<211> LENGTH: 199
<212> TYPE: DNA
<213> ORGANISM: Homo sapiens

<400> SEQUENCE: 289

| | |
|---|---|
| ctcatgctta catccttagc tgatcattaa actttgtgac catttcatgc tcactgcttt | 60 |
| cttgcccggg agctaatggt gaggaaaggt cactgggaac cagcgcacca acctcagaca | 120 |
| tcgattttgt tccagccttt tttcctgggc aggggtggct atcacctgct ggtaggcagc | 180 |
| ggcaggccca ctgtcctgc | 199 |

<210> SEQ ID NO 290
<211> LENGTH: 21
<212> TYPE: DNA
<213> ORGANISM: Homo sapiens

<400> SEQUENCE: 290

| | |
|---|---|
| ttaaactttg tgaccatttc a | 21 |

<210> SEQ ID NO 291
<211> LENGTH: 18
<212> TYPE: DNA
<213> ORGANISM: Homo sapiens

<400> SEQUENCE: 291

| | |
|---|---|
| taccagcagg tgatagcc | 18 |

<210> SEQ ID NO 292
<211> LENGTH: 181
<212> TYPE: DNA
<213> ORGANISM: Homo sapiens

<400> SEQUENCE: 292

| | |
|---|---|
| tgacagaaaa gtctcagagc agtgccttct gagctcttct acaccaagca ggcagaatgt | 60 |
| tcactgctaa tgaggctgga gctggtcccc agcagtggta ggaagcttcc aacaggctca | 120 |
| ggctgtgggt gcttgcaggg gcacagtgtg acggccacgg gcctcagagc tctggtgggc | 180 |
| t | 181 |

<210> SEQ ID NO 293
<211> LENGTH: 20
<212> TYPE: DNA
<213> ORGANISM: Homo sapiens

<400> SEQUENCE: 293

| | |
|---|---|
| gacagaaaag tctcagagca | 20 |

<210> SEQ ID NO 294
<211> LENGTH: 18
<212> TYPE: DNA
<213> ORGANISM: Homo sapiens

<400> SEQUENCE: 294

| | |
|---|---|
| caagcaccca cagcctga | 18 |

<210> SEQ ID NO 295
<211> LENGTH: 187
<212> TYPE: DNA
<213> ORGANISM: Homo sapiens

<400> SEQUENCE: 295
acatctttct caaataaaga taacagcgat gtattttcac aaaagcaaga gcttagaaag    60
tactccaccc aggtatccct cttggaaaaa atacttaagg aaatatgaca aatggcaaag   120
tgattgttat ggatggaatg tttgtatcct cccaaaattc acatgttgag accctaattc   180
caatatg                                                              187

<210> SEQ ID NO 296
<211> LENGTH: 20
<212> TYPE: DNA
<213> ORGANISM: Homo sapiens

<400> SEQUENCE: 296
attttcacaa aagcaagagc                                                 20

<210> SEQ ID NO 297
<211> LENGTH: 20
<212> TYPE: DNA
<213> ORGANISM: Homo sapiens

<400> SEQUENCE: 297
ttgggaggat acaaacattc                                                 20

<210> SEQ ID NO 298
<211> LENGTH: 180
<212> TYPE: DNA
<213> ORGANISM: Homo sapiens

<400> SEQUENCE: 298
aggggcattc tacaaaacac ccaaccggtc aaggtcgctg aggccaagga gagattgggc    60
aaccgtcaca aaccagagaa gccgaggaga cctttcagcc aacgccatgt ggggtcctga   120
gcaggaccca ccggaagttg gtgcagctgc ctaaagaccg tcctggctga aagaaacag    180

<210> SEQ ID NO 299
<211> LENGTH: 18
<212> TYPE: DNA
<213> ORGANISM: Homo sapiens

<400> SEQUENCE: 299
aaggagagat tgggcaac                                                   18

<210> SEQ ID NO 300
<211> LENGTH: 19
<212> TYPE: DNA
<213> ORGANISM: Homo sapiens

<400> SEQUENCE: 300
gtttcttctc agccaggac                                                  19

<210> SEQ ID NO 301
<211> LENGTH: 228
<212> TYPE: DNA
<213> ORGANISM: Homo sapiens

<400> SEQUENCE: 301
tggccctgac ctgccagagc tgttggcctc cagctggcgg gtaaaaccca cggccttctc    60
agaacaggtt tctcaacaca tgagacagaa cacaccagac ttccaagggg aacacctgga   120
tggagctggt tacccagatc gttcaacacc gaggggcagc ggcttgaggg tctttccacg   180

```
aaggcttgga ttaacaagag gagcasrggt ctctccagga tgggccca          228
```

```
<210> SEQ ID NO 302
<211> LENGTH: 20
<212> TYPE: DNA
<213> ORGANISM: Homo sapiens

<400> SEQUENCE: 302
catgagacag aacacaccag                                          20

<210> SEQ ID NO 303
<211> LENGTH: 20
<212> TYPE: DNA
<213> ORGANISM: Homo sapiens

<400> SEQUENCE: 303
tcttgttaat ccaagccttc                                          20

<210> SEQ ID NO 304
<211> LENGTH: 223
<212> TYPE: DNA
<213> ORGANISM: Homo sapiens

<400> SEQUENCE: 304
ccacccagtg tcacgtcacg gccccggcac gccatccacg gaccctggat ggagcccagc   60
tgcctccagg agcgcagttt aactacaaag gagccctggc tgcccgcccc gcccagacgc  120
actgacctgt tgttctctgt ggctgctgat ggcccatccc caaccactgg tgactcttcc  180
ctggggcccc aagctcagcc cctaaccccc tgttgctgga agt                    223

<210> SEQ ID NO 305
<211> LENGTH: 18
<212> TYPE: DNA
<213> ORGANISM: Homo sapiens

<400> SEQUENCE: 305
cacggaccct ggatggag                                            18

<210> SEQ ID NO 306
<211> LENGTH: 18
<212> TYPE: DNA
<213> ORGANISM: Homo sapiens

<400> SEQUENCE: 306
cagggaagag tcaccagt                                            18

<210> SEQ ID NO 307
<211> LENGTH: 186
<212> TYPE: DNA
<213> ORGANISM: Homo sapiens

<400> SEQUENCE: 307
cagaggactg ggctgcgggg tcaggaatgg gcacacttcc taactgcagg acactctaag   60
ggctttggtc atgcacacgc agccaagaga aggtgtcgct gacacacagc cttccaggag  120
cggacttgga gacctcgcca aggaccagga ctccccagca ctcacactcc cttaggcgct  180
gaagtc                                                             186

<210> SEQ ID NO 308
<211> LENGTH: 20
<212> TYPE: DNA
<213> ORGANISM: Homo sapiens
```

```
<400> SEQUENCE: 308
actctaaggg ctttggtcat                                                  20

<210> SEQ ID NO 309
<211> LENGTH: 20
<212> TYPE: DNA
<213> ORGANISM: Homo sapiens

<400> SEQUENCE: 309
ctaagggagt gtgagtgctg                                                  20

<210> SEQ ID NO 310
<211> LENGTH: 185
<212> TYPE: DNA
<213> ORGANISM: Homo sapiens

<400> SEQUENCE: 310
gaagaggaca acacggggct gtctgcagag cacctgccac gcgccaggct ctgtgtccac      60
aagcacggcg gctgctccca catgacagag ctcgtgcggc agctccagga ctgtctggtg     120
ccagagcccc agctctccgc cagccccagg ccactgtgcg aggccctcag tgaagagggg     180
gccgt                                                                 185

<210> SEQ ID NO 311
<211> LENGTH: 18
<212> TYPE: DNA
<213> ORGANISM: Homo sapiens

<400> SEQUENCE: 311
cgccaggctc tgtgtcca                                                    18

<210> SEQ ID NO 312
<211> LENGTH: 18
<212> TYPE: DNA
<213> ORGANISM: Homo sapiens

<400> SEQUENCE: 312
ggccccctct tcactgag                                                    18

<210> SEQ ID NO 313
<211> LENGTH: 173
<212> TYPE: DNA
<213> ORGANISM: Homo sapiens

<400> SEQUENCE: 313
tctaaataat gttaatgatc aaatttagtc agatctcaat cttcatatgt tagttgcctt      60
cttaataaat attctgtttt ctttatcgtt ctttatttgt atctccacct tcatttctga     120
ttaaattaag aagttttgtc tcttccattt aataattaat gtatttaata acc            173

<210> SEQ ID NO 314
<211> LENGTH: 22
<212> TYPE: DNA
<213> ORGANISM: Homo sapiens

<400> SEQUENCE: 314
tttagtcaga tctcaatctt ca                                               22

<210> SEQ ID NO 315
<211> LENGTH: 22
<212> TYPE: DNA
```

<210> SEQ ID NO 315
<211> LENGTH: 22
<212> TYPE: DNA
<213> ORGANISM: Homo sapiens

<400> SEQUENCE: 315
aatggaagag acaaaacttc tt                                              22

<210> SEQ ID NO 316
<211> LENGTH: 194
<212> TYPE: DNA
<213> ORGANISM: Homo sapiens

<400> SEQUENCE: 316
cacactccac actggcccca cgcgggtggc gaaggactca gccagagcct ggcaggatcc     60
tggggtgtct atttccaagg aatgttctgg aagaaacata cacacatact tgtttgccag    120
atttacctgt gtggtcttcc agatgagaag cagcctgtgt cactccataa gggagagtgc    180
gtgcagcatt gaga                                                      194

<210> SEQ ID NO 317
<211> LENGTH: 18
<212> TYPE: DNA
<213> ORGANISM: Homo sapiens

<400> SEQUENCE: 317
gaaggactca gccagagc                                                   18

<210> SEQ ID NO 318
<211> LENGTH: 20
<212> TYPE: DNA
<213> ORGANISM: Homo sapiens

<400> SEQUENCE: 318
ctctccctta tggagtgaca                                                 20

<210> SEQ ID NO 319
<211> LENGTH: 225
<212> TYPE: DNA
<213> ORGANISM: Homo sapiens

<400> SEQUENCE: 319
aagaaactcc caaggaacgc attgtcccaa gttgctgcac cagtcagtgt acattcccac     60
aaacagtgca tgagagttcc tgttgcttgt gaaataaatg gtcagcattc agtgttgtca    120
gcttttaaaa ttttctcctt tctagtgggc atgtaatggt ctcacattat agttttaatt    180
tgcattttcc tggtgacatg tgatacggaa ccttcctccc atgct                    225

<210> SEQ ID NO 320
<211> LENGTH: 19
<212> TYPE: DNA
<213> ORGANISM: Homo sapiens

<400> SEQUENCE: 320
accagtcagt gtacattcc                                                  19

<210> SEQ ID NO 321
<211> LENGTH: 19
<212> TYPE: DNA
<213> ORGANISM: Homo sapiens

<400> SEQUENCE: 321
ggaaaatgca aattaaaac                                                  19

```
<210> SEQ ID NO 322
<211> LENGTH: 170
<212> TYPE: DNA
<213> ORGANISM: Homo sapiens

<400> SEQUENCE: 322
gtgcaattta attacaaacg cttaaatggg gaggtcaggg gcagagggat gatgtcacaa      60
acacacccac gtgtgcttgg tgcaaaacag taaaacaaac agcaagaagg tccatgaagg     120
aaagatcgcc tctgtcagtg ggagtaatga gagtggctga tggacaggtg                170

<210> SEQ ID NO 323
<211> LENGTH: 20
<212> TYPE: DNA
<213> ORGANISM: Homo sapiens

<400> SEQUENCE: 323
cgcttaaatg gggaggtcag                                                  20

<210> SEQ ID NO 324
<211> LENGTH: 20
<212> TYPE: DNA
<213> ORGANISM: Homo sapiens

<400> SEQUENCE: 324
cctgtccatc agccactctc                                                  20

<210> SEQ ID NO 325
<211> LENGTH: 189
<212> TYPE: DNA
<213> ORGANISM: Homo sapiens

<400> SEQUENCE: 325
acgccaagca ggagatgcca gacacagagt ccatcctgag agagtctgtt cctgtccaag      60
ctcagaaaca caggaagcca cctgtgctgt agcagcacac ggagatgcat cctttctggt     120 ccacccacg gccctcattg cagtcaggga tcctctccca gaaagtccct gctgccagcc     180
cctgcccctt                                                             189

<210> SEQ ID NO 326
<211> LENGTH: 20
<212> TYPE: DNA
<213> ORGANISM: Homo sapiens

<400> SEQUENCE: 326
agcaggagat gccagacaca                                                  20

<210> SEQ ID NO 327
<211> LENGTH: 20
<212> TYPE: DNA
<213> ORGANISM: Homo sapiens

<400> SEQUENCE: 327
ggtggaccag aaaggatgca                                                  20

<210> SEQ ID NO 328
<211> LENGTH: 170
<212> TYPE: DNA
<213> ORGANISM: Homo sapiens

<400> SEQUENCE: 328
catgagaaag actttgttcc catgagaaca acaagagaaa ctcaaacaaa attaaaattg      60
```

```
tactttcta  aaagaccggg  gtgggggtcg  tggtcaggca  gcagcatgaa  gaaagccttg      120
agaactgaat  tccagaaaga  aacaagcata  ggcaagaaag  agagatgaca                170

<210> SEQ ID NO 329
<211> LENGTH: 22
<212> TYPE: DNA
<213> ORGANISM: Homo sapiens

<400> SEQUENCE: 329
cccatgagaa  caacaagaga  aa                                                 22

<210> SEQ ID NO 330
<211> LENGTH: 20
<212> TYPE: DNA
<213> ORGANISM: Homo sapiens

<400> SEQUENCE: 330
ctctttcttg  cctatgcttg                                                     20

<210> SEQ ID NO 331
<211> LENGTH: 167
<212> TYPE: DNA
<213> ORGANISM: Homo sapiens

<400> SEQUENCE: 331
aagatttaga  acagctgaag  cagcgagaaa  aacccagca  tgagtcagaa  ctggagcaac      60
tgaggattta  ttttgaaaag  aagttaaggg  atgctgagaa  aacttaccaa  gaagacctaa    120
ccctgttaca  gcagaggctg  caggggggcga  gggaagatgc  tcttctg                  167

<210> SEQ ID NO 332
<211> LENGTH: 21
<212> TYPE: DNA
<213> ORGANISM: Homo sapiens

<400> SEQUENCE: 332
cagctgaagc  agcgagaaaa  a                                                  21

<210> SEQ ID NO 333
<211> LENGTH: 19
<212> TYPE: DNA
<213> ORGANISM: Homo sapiens

<400> SEQUENCE: 333
cccctgcagc  ctctgctgt                                                      19

<210> SEQ ID NO 334
<211> LENGTH: 174
<212> TYPE: DNA
<213> ORGANISM: Homo sapiens

<400> SEQUENCE: 334
gggaaactga  cttggctttt  gcaagggtca  ttgcttcctg  atgcatgttt  aactgtcctg      60
tgttcacttt  gttgccgcag  ttttttagag  gaacgtaaag  agatcaccga  gaaattcagt    120
gcggaacaag  atgccttcct  gcaggaggcc  caggagcagc  atgcccgtga  gctg           174

<210> SEQ ID NO 335
<211> LENGTH: 22
<212> TYPE: DNA
<213> ORGANISM: Homo sapiens

<400> SEQUENCE: 335
```

-continued

```
gggaaactga cttggctttt gc                                               22

<210> SEQ ID NO 336
<211> LENGTH: 20
<212> TYPE: DNA
<213> ORGANISM: Homo sapiens

<400> SEQUENCE: 336
ggcatcttgt tccgcactga                                                  20

<210> SEQ ID NO 337
<211> LENGTH: 175
<212> TYPE: DNA
<213> ORGANISM: Homo sapiens

<400> SEQUENCE: 337
ccctgcacac tgacctgcat gccctcgtca cctgcactct gcatgctcac catctgacgg      60
actcctgcga cgggcatggg aaggtcgccg ccgccggcag ccttgcgagc actttggatg     120
tgtgcacccg gcatgccagg cccgagtcaa cagactggcc gaccttggcg tcctg         175

<210> SEQ ID NO 338
<211> LENGTH: 20
<212> TYPE: DNA
<213> ORGANISM: Homo sapiens

<400> SEQUENCE: 338
gccctcgtca cctgcactct                                                  20

<210> SEQ ID NO 339
<211> LENGTH: 20
<212> TYPE: DNA
<213> ORGANISM: Homo sapiens

<400> SEQUENCE: 339
ccaaggtcgg ccagtctgtt                                                  20

<210> SEQ ID NO 340
<211> LENGTH: 155
<212> TYPE: DNA
<213> ORGANISM: Homo sapiens

<400> SEQUENCE: 340
tttattgctg agtggtattc catttatgg gtccattata gtttatttgt ccagacactt       60
catggaaaga catcagtgtt tcctgttttt caatcataaa ttgatgttta attttaaaat     120
tttggaattg tagaagaaat gcaattcttt tttcc                                155

<210> SEQ ID NO 341
<211> LENGTH: 22
<212> TYPE: DNA
<213> ORGANISM: Homo sapiens

<400> SEQUENCE: 341
tgggtccatt atagtttatt tg                                               22

<210> SEQ ID NO 342
<211> LENGTH: 22
<212> TYPE: DNA
<213> ORGANISM: Homo sapiens

<400> SEQUENCE: 342
```

```
tgcatttctt ctacaattcc aa                                             22

<210> SEQ ID NO 343
<211> LENGTH: 208
<212> TYPE: DNA
<213> ORGANISM: Homo sapiens

<400> SEQUENCE: 343
ctttggtgca gaatcatgct gcaggcaagg tgggcccacc tccctggaat ttcatccccc    60
ccgtcagtta aacccatggt ggttttattt tctaggccac ctgatctggg aggaccacct   120
ccaagaaaag cagtcctatc gatgaacggt ctaagttatg gtgttatcag agtggatact   180
gaagaaaagt tgtcagtcct tactgttc                                      208

<210> SEQ ID NO 344
<211> LENGTH: 20
<212> TYPE: DNA
<213> ORGANISM: Homo sapiens

<400> SEQUENCE: 344
ggcccacctc cctggaattt                                                20

<210> SEQ ID NO 345
<211> LENGTH: 22
<212> TYPE: DNA
<213> ORGANISM: Homo sapiens

<400> SEQUENCE: 345
tccactctga taacaccata ac                                             22

<210> SEQ ID NO 346
<211> LENGTH: 232
<212> TYPE: DNA
<213> ORGANISM: Homo sapiens

<400> SEQUENCE: 346
atcacctggt ttggtgcatc ctcgcagaaa gagagccata cagtgaagtg gaaacacacc    60
caaaagctct gcaatattcc tagaagttct cgaatctcct ccttaacaga gctgcagaag   120
ggaaacacag acaggaagca cctgtttgac tcagacagca gccctaatgc agtgccactc   180
aggagcattc cctcatttga agaccccccca attacatgaa attatcaacc cc           232

<210> SEQ ID NO 347
<211> LENGTH: 20
<212> TYPE: DNA
<213> ORGANISM: Homo sapiens

<400> SEQUENCE: 347
acacccaaaa gctctgcaat                                                20

<210> SEQ ID NO 348
<211> LENGTH: 20
<212> TYPE: DNA
<213> ORGANISM: Homo sapiens

<400> SEQUENCE: 348
caaatgaggg aatgctcctg                                                20

<210> SEQ ID NO 349
<211> LENGTH: 240
<212> TYPE: DNA
<213> ORGANISM: Homo sapiens
```

<400> SEQUENCE: 349

```
ggaactgcag gagatccctg ctgccttcca gttcatggga tgatggcctc cacttctgcc      60
cctgtttgct tctcctttca aatcttacat gaaggtatac agtttgaaga agccagtttg     120
actccaatat ctgtgcaatg gaatactgct cattaaaaag gaattaaaact attgatacac    180
acaacatggg tgaagatcaa actgtctcct tcccttttgat tcaagggaat ctgagaaatg    240
```

<210> SEQ ID NO 350
<211> LENGTH: 19
<212> TYPE: DNA
<213> ORGANISM: Homo sapiens

<400> SEQUENCE: 350

```
acttctgccc ctgtttgct                                                   19
```

<210> SEQ ID NO 351
<211> LENGTH: 21
<212> TYPE: DNA
<213> ORGANISM: Homo sapiens

<400> SEQUENCE: 351

```
tgatcttcac ccatgttgtg t                                                21
```

<210> SEQ ID NO 352
<211> LENGTH: 187
<212> TYPE: DNA
<213> ORGANISM: Homo sapiens

<400> SEQUENCE: 352

```
tggagaaagt tgttgcaaac tgcccagaga ccctgggagt cactccagtt ttctgaaacc      60
cagatatttc agtgcctcag gagagacaag tcctgaccttt ctctcctcca gctctcccag    120
gagataggca agccccctaac tccctaacta agcccttcag acctgaaatc cattgagtgg    180
cttcttt                                                              187
```

<210> SEQ ID NO 353
<211> LENGTH: 18
<212> TYPE: DNA
<213> ORGANISM: Homo sapiens

<400> SEQUENCE: 353

```
gcaaactgcc cagagacc                                                   18
```

<210> SEQ ID NO 354
<211> LENGTH: 20
<212> TYPE: DNA
<213> ORGANISM: Homo sapiens

<400> SEQUENCE: 354

```
ttagggagtt aggggcttgc                                                  20
```

<210> SEQ ID NO 355
<211> LENGTH: 184
<212> TYPE: DNA
<213> ORGANISM: Homo sapiens

<400> SEQUENCE: 355

```
agggccatgg gatgatgcag gtggagactg gagtgctaca gctgcaagca aatacatttc      60
tgtgctgtga agccacccat ttggtggtac tacgttaaaa cagctctagg aaattaatac     120
```

```
                                    -continued
agatgttgcc tgtatttttg tttctcatat tactactcat tgttttaatg atgactgttt    180
tatt                                                                 184

<210> SEQ ID NO 356
<211> LENGTH: 20
<212> TYPE: DNA
<213> ORGANISM: Homo sapiens

<400> SEQUENCE: 356
aggtggagac tggagtgcta                                                 20

<210> SEQ ID NO 357
<211> LENGTH: 22
<212> TYPE: DNA
<213> ORGANISM: Homo sapiens

<400> SEQUENCE: 357
agaaacaaaa atacaggcaa ca                                              22
```